(12) United States Patent
Ha et al.

(10) Patent No.: US 10,244,935 B2
(45) Date of Patent: Apr. 2, 2019

(54) HANDLE WITH FEATURES TO SECURE A CATHETER ASSEMBLY TO AN ENDOSCOPE

(71) Applicant: Acclarent, Inc., Menlo Park, CA (US)

(72) Inventors: Hung V. Ha, San Jose, CA (US);
Ketan P. Muni, San Jose, CA (US);
Darius D. Eghbal, Oakland, CA (US);
James G. Lee, Cincinnati, OH (US);
Gregory W. Johnson, Milford, OH (US); Lawrence D. Wasicek, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 353 days.

(21) Appl. No.: 14/827,848

(22) Filed: Aug. 17, 2015

(65) Prior Publication Data

US 2016/0287065 A1 Oct. 6, 2016

Related U.S. Application Data

(60) Provisional application No. 62/139,941, filed on Mar. 30, 2015.

(51) Int. Cl.
*A61B 1/00* (2006.01)
*A61M 25/01* (2006.01)
(Continued)

(52) U.S. Cl.
CPC .............. *A61B 1/32* (2013.01); *A61B 1/0014* (2013.01); *A61B 1/00066* (2013.01);
(Continued)

(58) Field of Classification Search
CPC ............ A61B 1/00064; A61B 1/00066; A61B 1/00087; A61B 1/00121; A61B 1/00128;
(Continued)

(56) References Cited

U.S. PATENT DOCUMENTS 6,716,813 B2   4/2004   Lim et al.
9,155,492 B2   10/2015  Jenkins et al.
(Continued)

OTHER PUBLICATIONS

St. Croix, B., et al., "Genes Expressed in Human Tumor Endothelium," Science, Aug. 18, 2000, 289:1197-1202, 6 pgs.
U.S. Appl. No. 62/139,941, filed Mar. 30, 2015.

*Primary Examiner* — Ryan Henderson
(74) *Attorney, Agent, or Firm* — Frost Brown Todd LLC

(57) ABSTRACT

A dilation system includes a handle, guide member, balloon dilation member, balloon, dilation member movement actuator, and endoscope. The handle is configured to provide single-handed use to a user. The handle includes a first and second body member pivotably coupled together such that the first body member and the second body member are configured to pivot toward and away from one another. The handle includes a rotation mechanism configured to impart rotation upon the guide member. The handle further includes a locking feature configured to lock endoscope in position relative to the handle. The handle may further include a rotation limiting feature configured to limit rotation of the guide member and or the body members. The dilation member movement actuator is configured to translate to thereby cause translation of the balloon dilation member. One or more components of the dilation system may include a plurality of measure markings.

6 Claims, 73 Drawing Sheets

(51) Int. Cl.
*A61B 1/32* (2006.01)
*A61M 29/00* (2006.01)

(52) U.S. Cl.
CPC ...... *A61B 1/00082* (2013.01); *A61B 1/00131* (2013.01); *A61B 1/00133* (2013.01); *A61B 1/00154* (2013.01); *A61M 25/01* (2013.01); *A61M 29/00* (2013.01); *A61B 1/00183* (2013.01); *A61B 1/00195* (2013.01); *A61M 2210/0681* (2013.01)

(58) Field of Classification Search
CPC .............. A61B 1/00133; A61B 1/0014; A61B 1/00154; A61B 1/00135; A61B 1/00137; A61B 1/233; A61B 17/00234; A61B 2017/00292; A61B 2017/00296; A61B 2017/0034
USPC ......... 600/104, 106, 107, 114–116, 121–125
See application file for complete search history.

(56) References Cited

U.S. PATENT DOCUMENTS

| | | | |
|---|---|---|---|
| 2008/0183128 A1 | 7/2008 | Morriss et al. | |
| 2008/0275483 A1* | 11/2008 | Makower | A61B 17/24 606/192 |
| 2010/0030031 A1 | 2/2010 | Goldfarb et al. | |
| 2010/0099946 A1* | 4/2010 | Jenkins | A61B 1/0014 600/104 |
| 2010/0274188 A1 | 10/2010 | Chang et al. | |
| 2011/0004057 A1 | 1/2011 | Goldfarb et al. | |
| 2012/0123208 A1* | 5/2012 | Remmerswaal | A61B 1/018 600/116 |
| 2013/0096378 A1* | 4/2013 | Alexander | A61B 1/00016 600/106 |
| 2015/0351613 A1* | 12/2015 | Knight | A61B 1/00128 600/104 |
| 2016/0081537 A1* | 3/2016 | Farhadi | A61B 1/00135 600/462 |

* cited by examiner

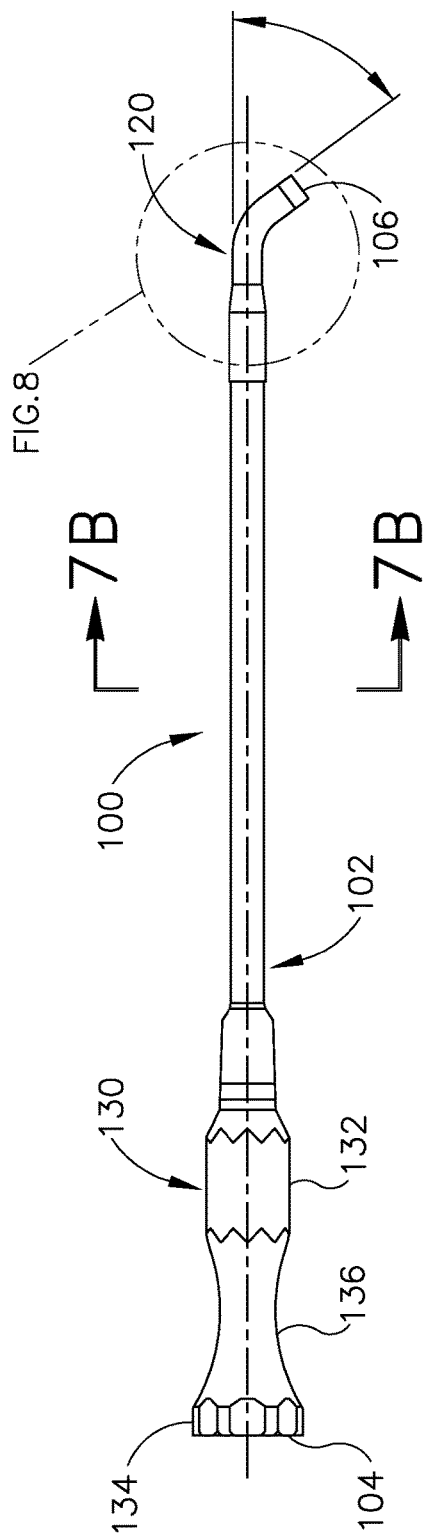
Fig.7A
Fig.7B
Fig.8

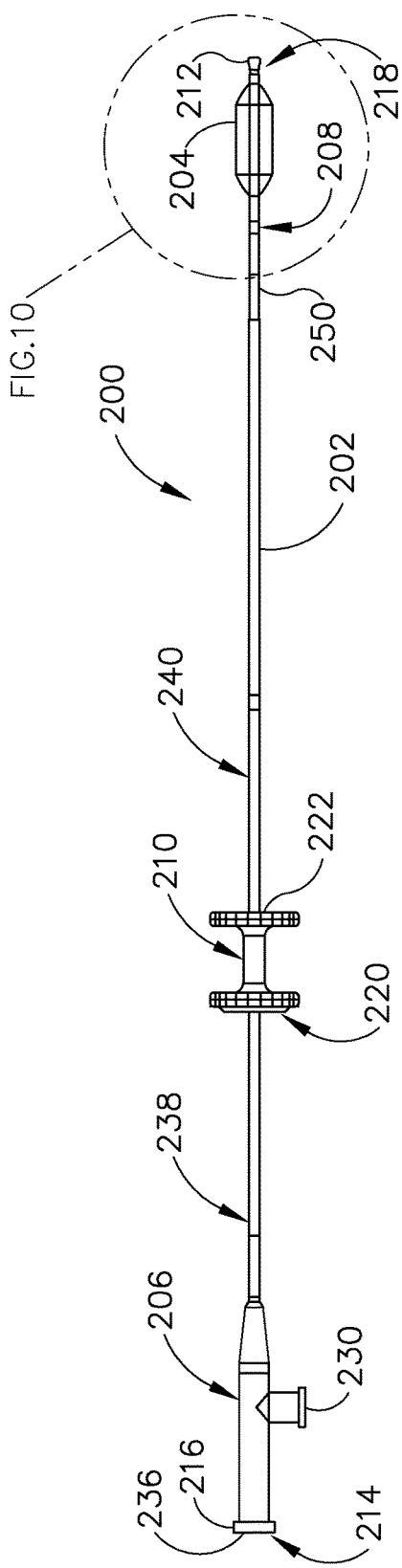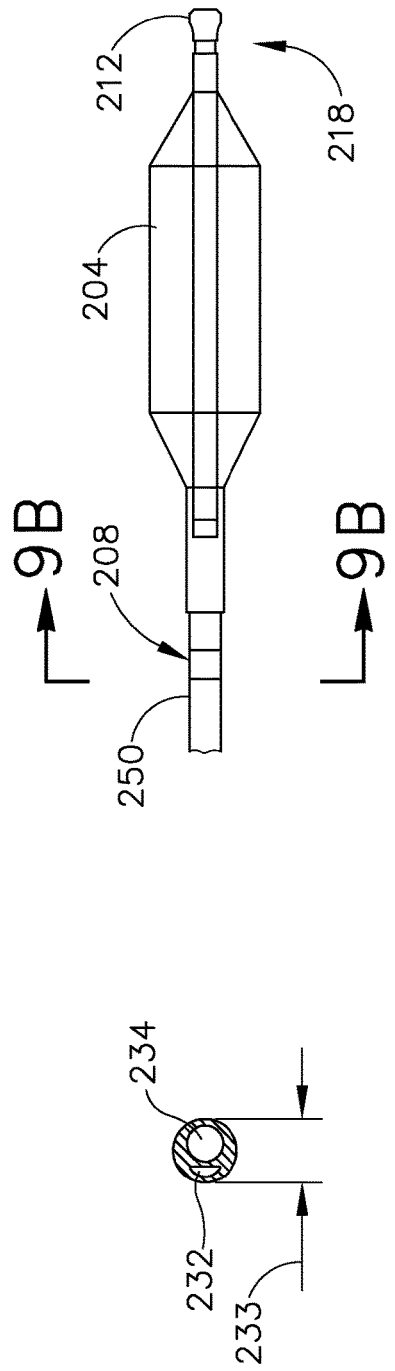

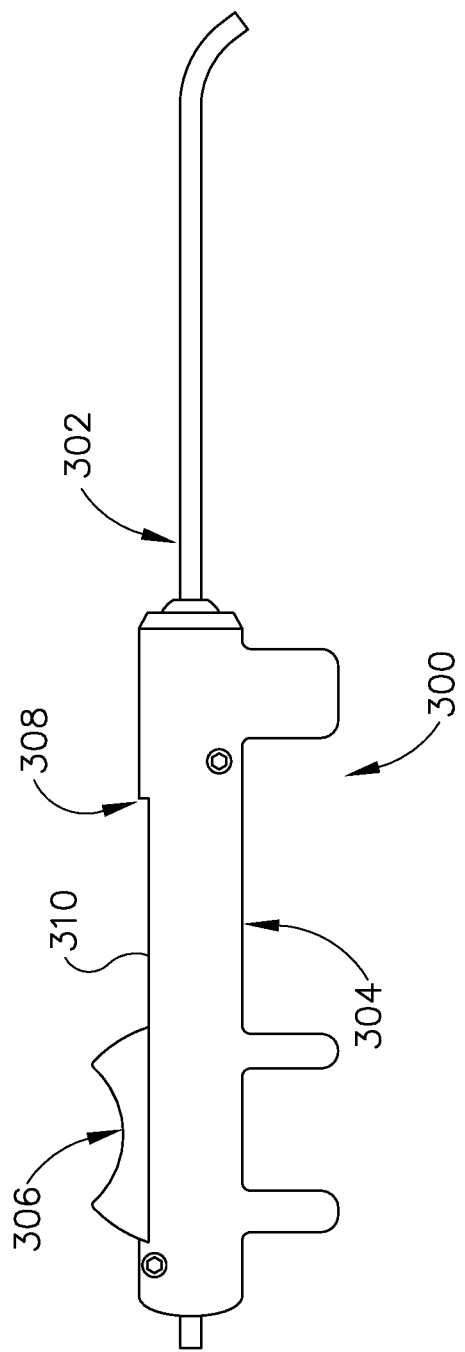

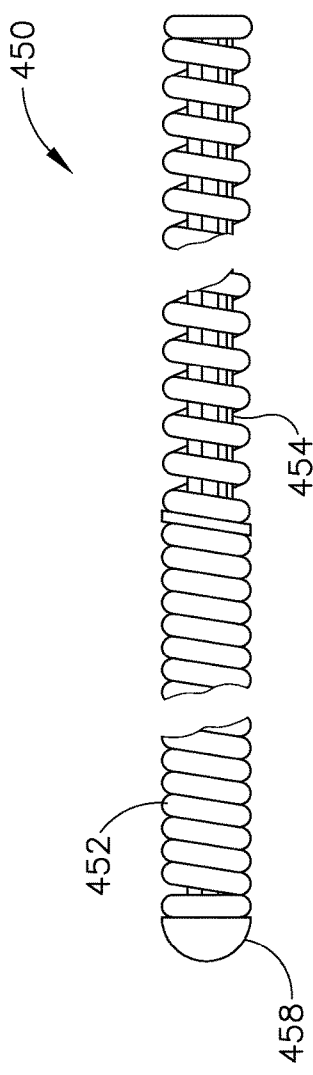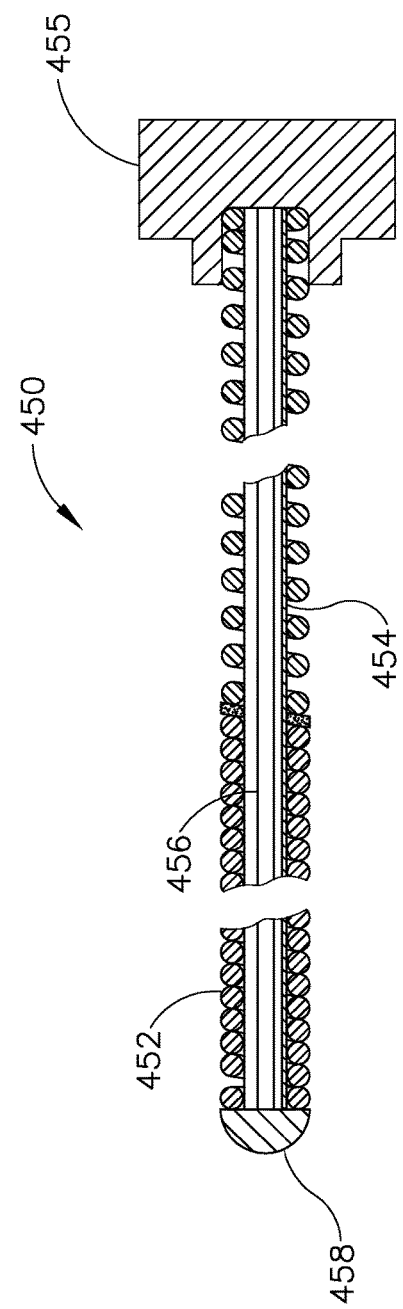

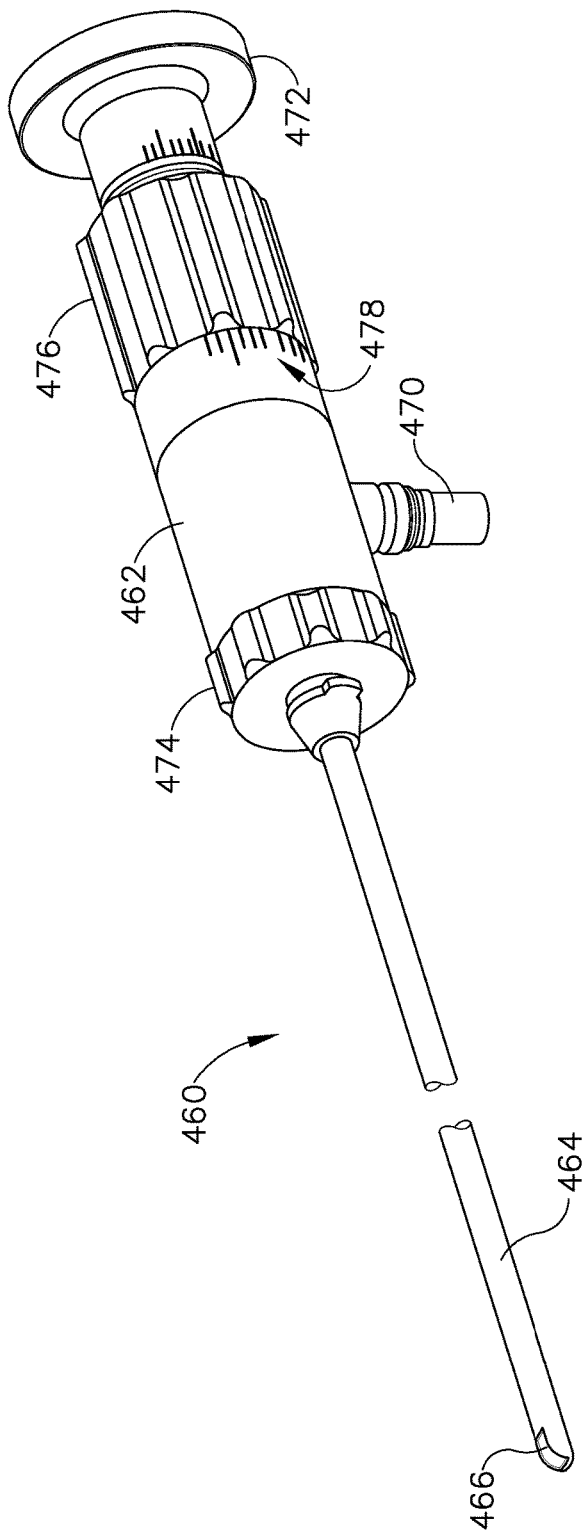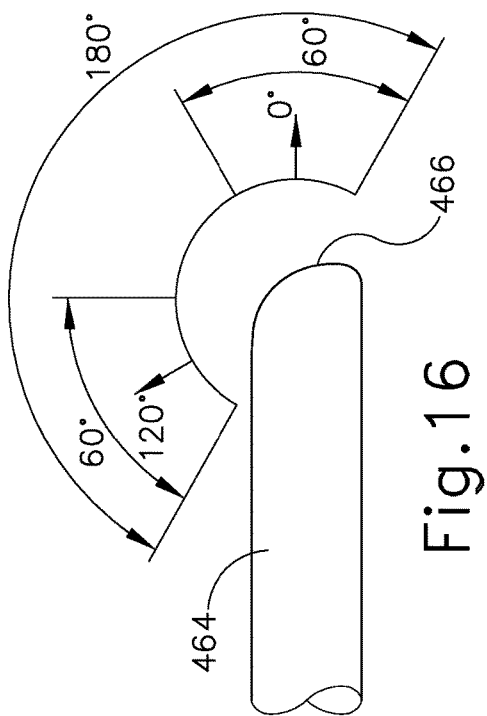

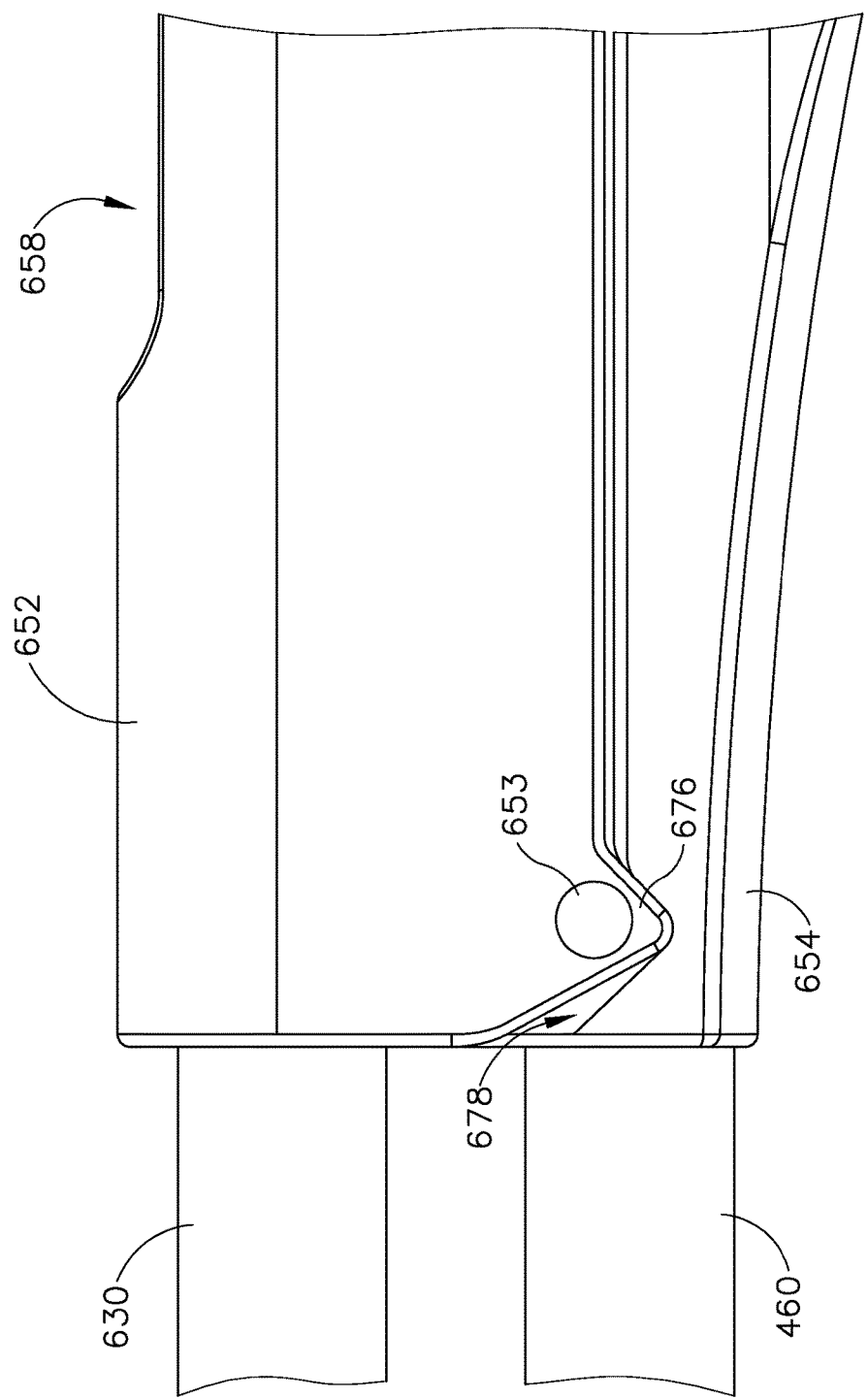

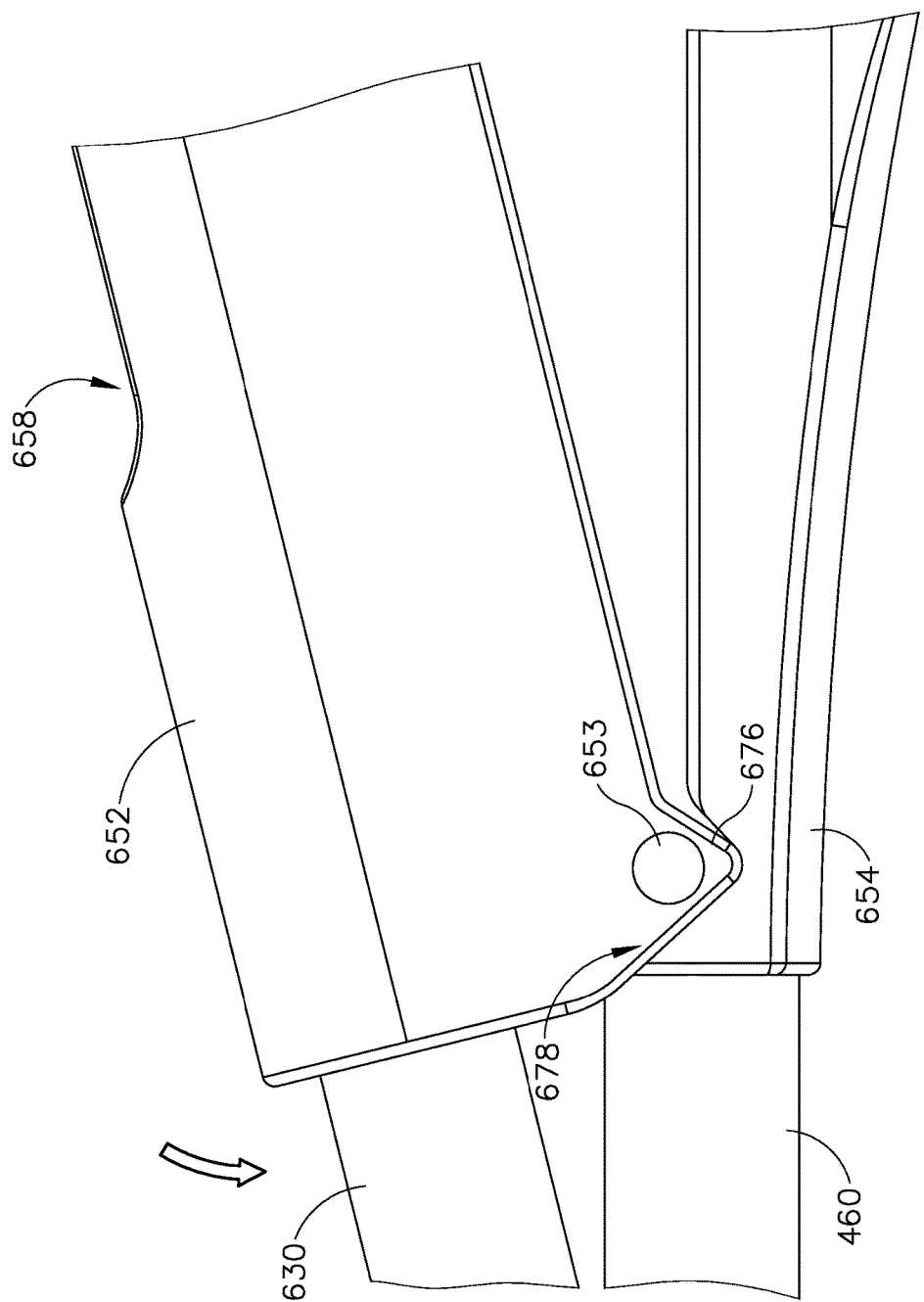

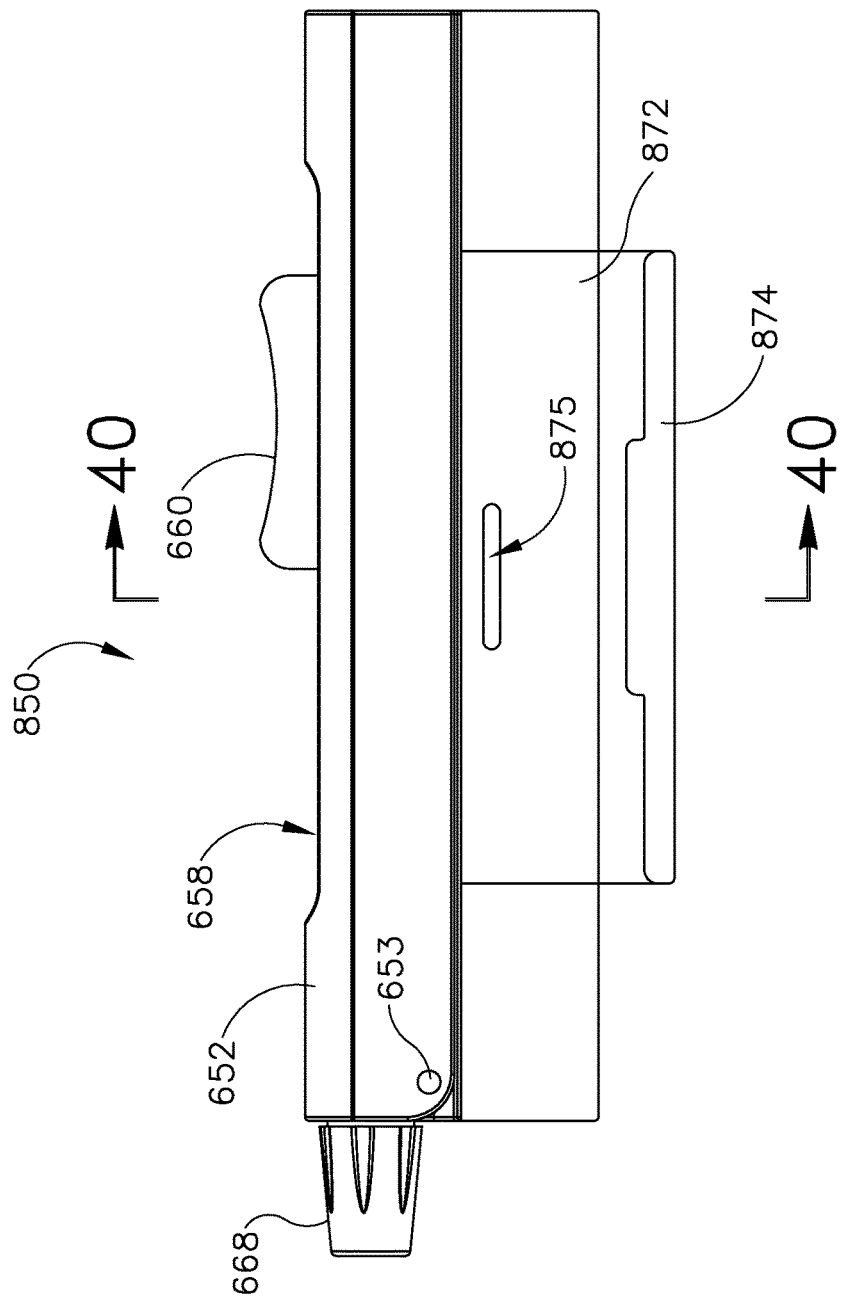

HANDLE WITH FEATURES TO SECURE A CATHETER ASSEMBLY TO AN ENDOSCOPE

PRIORITY

This application claims priority to U.S. Provisional Patent App. No. 62/139,941, entitled "Handle with Features to Secure a Catheter Assembly to an Endoscope," filed Mar. 30, 2015, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pat. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

It may be desirable to provide easily controlled inflation/deflation of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 7A depicts a side elevational view of an exemplary guide catheter;

FIG. 7B depicts a cross-sectional front view of the guide catheter of FIG. 7A taken through line 7B-7B of FIG. 7A;

FIG. 8 depicts a detailed side elevational view of a distal end of the guide catheter of FIG. 7A;

FIG. 9A depicts a side elevational view of an exemplary balloon dilation catheter;

FIG. 9B depicts a cross-sectional front view of the balloon dilation catheter of FIG. 9A taken through line 9B-9B of FIG. 10;

FIG. 10 depicts a detailed side elevational view of a distal end of the balloon dilation catheter of FIG. 9A;

FIG. 11 depicts a side elevational view of another exemplary guide catheter;

FIG. 13 depicts a side elevational view of an exemplary illuminating guidewire suitable for use with the dilation catheter system of FIG. 12;

FIG. 14 depicts a cross-sectional side view of the illuminating guidewire of FIG. 13;

FIG. 15 depicts a perspective view of an exemplary endoscope suitable for use with the dilation catheter system of FIG. 12;

FIG. 16 depicts a side elevational view of the distal end of the endoscope of FIG. 15, showing an exemplary range of viewing angles;

FIG. 28A depicts a side elevational view of an exemplary rotation limiting feature of the handle of FIG. 24;

FIG. 28B depicts a side elevational view of the rotation limiting feature of FIG. 28A, with the guide catheter of FIG. 7A pivoted toward the endoscope of FIG. 15 as shown in FIG. 27E;

FIG. 39 depicts a side elevation view of the handle of FIG. 38;

Figure 1:
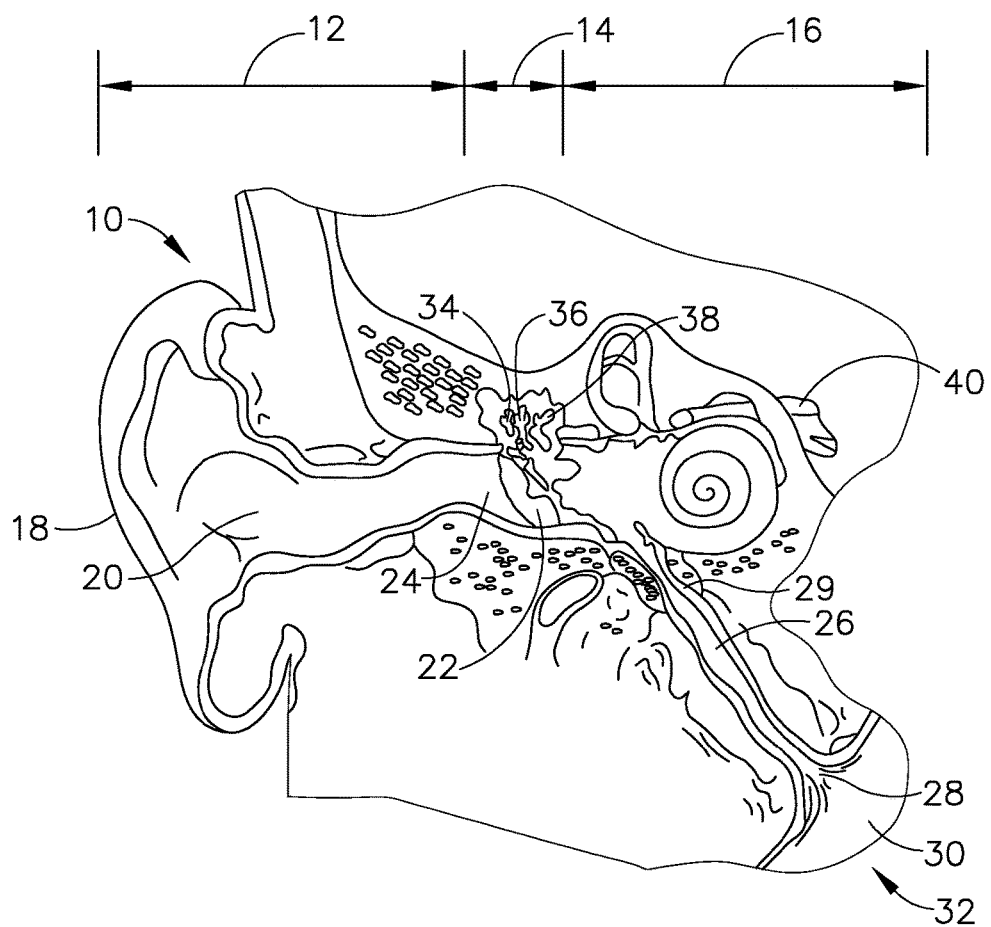
FIG. 1 depicts a cross-sectional front view of a human ear showing the inner, middle, and outer ear portions and the Eustachian tube connecting the middle ear with the nasopharynx region of the throat via a pharyngeal ostium thereof.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Methods of Treating the Middle Ear and Eustachian Tube

Figure 2:
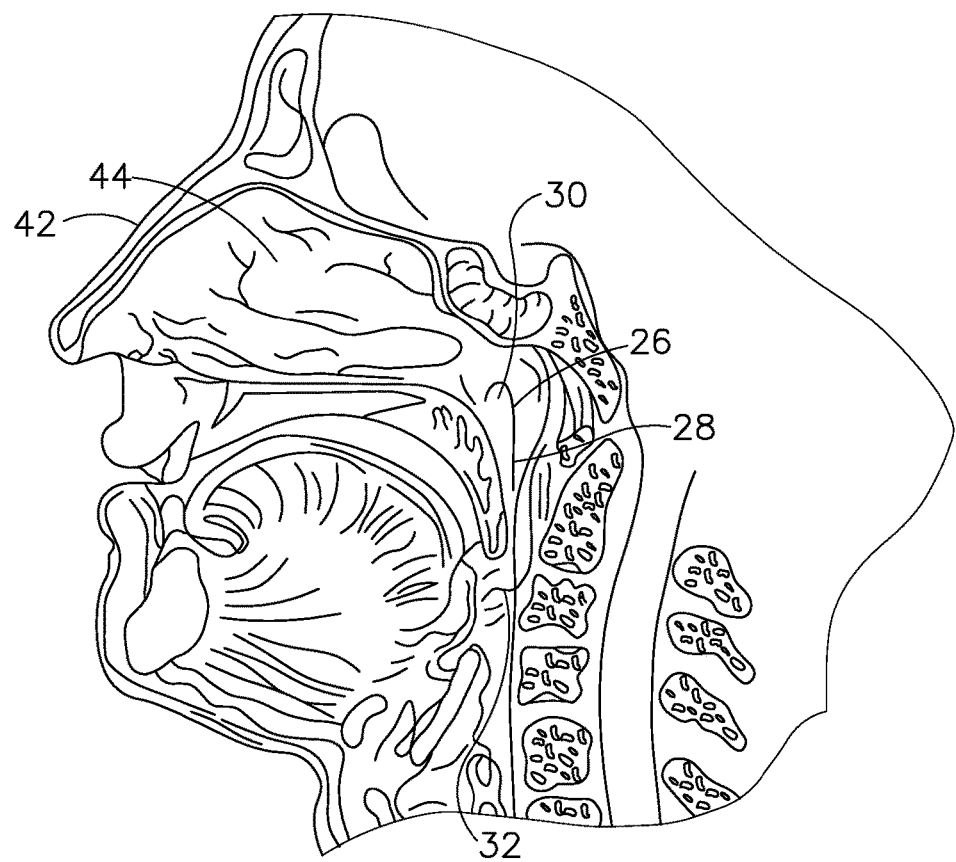
FIG. 2 depicts a cross-sectional side view of a human head showing the nasopharynx region of the throat illustrated in FIG. 1 containing the pharyngeal ostium of the Eustachian tube illustrated in FIG. 1.

Referring to FIGS. 1 and 2, an ear (10) is divided into three parts: an external ear (12), a middle ear (14), and an inner ear (16). The external ear (12) consists of an auricle (18) and ear canal (20) that gather sound and direct it toward a tympanic membrane (22) (also referred to as the eardrum) located at an inner end (24) of the ear canal (20). The middle ear (14) lies between the external ear (12) and the inner ear (16) and is connected to the back of the throat (32) by a Eustachian tube (26), which serves as a pressure equalizing valve between the ear (10) and the sinuses. The Eustachian tube (26) terminates in a pharyngeal ostium or ostium (28) in the nasopharynx region (30) of the throat (32). In addition to the tympanic membrane (22), the middle ear (14) also consists of three small ear bones (also referred to as the ossicles or auditory ossicles): the malleus (34) (also referred to as the hammer), the incus (36) (also referred to as the anvil), and the stapes (38) (also referred to as the stirrup). These middle ear bones (34, 36, 38) transmit sound vibrations to the inner ear (16) and thereby act as a transformer, converting sound vibrations in the ear canal (20) of the external ear (12) into fluid waves in the inner ear (16). These fluid waves stimulate several nerve endings (40) that, in turn, transmit sound energy to the brain where it is interpreted.

The Eustachian tube (26) is a narrow, two to two-and-a-half centimeter long channel, measured from the ostium (28)

to the bony isthmus (29), connecting the middle ear (14) with the nasopharynx region (30), the upper throat area just above the palate, in back of the nose (42). The Eustachian tube (26) functions as a pressure equalizing valve for the middle ear (14), which is normally filled with air. When functioning properly, the Eustachian tube (26) opens for a fraction of a second periodically (about once every three minutes) in response to swallowing or yawning. In so doing, it allows air into the middle ear (14) to replace air that has been absorbed by the middle ear lining (mucous membrane) or to equalize pressure changes occurring on altitude changes. Anything that interferes with this periodic opening and closing of the Eustachian tube (26) may result in hearing impairment or other ear symptoms.

Obstruction or blockage of the Eustachian tube (26) results in a negative middle ear pressure (14), with retraction, or sucking in, of the tympanic membrane (22). In adults, this is usually accompanied by some ear discomfort, a fullness or pressure feeling, and may result in a mild hearing impairment and head noise (commonly referred to as tinnitus). There may be no symptoms in children. If the obstruction is prolonged, fluid may be drawn from the mucous membrane of the middle ear (14), creating a condition referred to as serous otitis media—i.e., fluid in the middle ear (14). This may occur frequently in children in connection with an upper respiratory infection and account for the hearing impairment associated with this condition.

A lining membrane (mucous membrane) of the middle ear (14) and the Eustachian tube (26) is connected with, and is the same as, the membrane of the nose (42), the sinuses (44), and the throat (32). Infection of these areas results in mucous membrane swelling, which in turn may result in obstruction of the Eustachian tube (26). This is referred to as serous otitis media, i.e., essentially a collection of fluid in the middle ear (14) that can be acute or chronic, and may be the result of blockage of the ostium (28) of the Eustachian tube (26), which allows fluid to accumulate in the middle ear (14). In the presence of bacteria, this fluid may become infected, leading to an acute suppurative otitis media—i.e., an infected or abscessed middle ear (14). When infection does not develop, the fluid remains until the Eustachian tube (26) again begins to function normally, at which time the fluid is absorbed or drains down the Eustachian tube (26) into the throat (32) through the ostium (28) of the Eustachian tube (26).

Chronic serous otitis media may result from longstanding blockage of the Eustachian tube (26), or from thickening of the fluid so that it cannot be absorbed or drained down the Eustachian tube (26). This chronic condition may be associated with hearing impairment. There may be recurrent ear pain, especially when the individual catches a cold. Fortunately, serous otitis media may persist for many years without producing any permanent damage to the middle ear (14). The presence of fluid in the middle ear (14), however, may make it very susceptible to recurrent acute infections. These recurrent infections may result in damage to the middle ear (14).

When the Eustachian tube (26) contains a build-up of fluid, a number of things may occur. First, the body absorbs the air from the middle ear (14), causing a vacuum to form, which tends to pull the lining membrane and tympanic membrane (22) inwardly, causing pain. Next, the body replaces the vacuum with more fluid, which tends to relieve the pain, but the patient can experience a fullness sensation in the ear (10). Treatment of this condition with antihistamines and decongestants can take many weeks to be fully effective. Finally, the fluid can become infected, which is painful and makes the patient feel ill and which may cause the patient not to be able to hear well. If the inner ear (14) is affected, the patient may feel a spinning or turning sensation (e.g., vertigo). The infection may be treated with antibiotics.

However, even if antihistamines, decongestants, and antibiotics are used to treat an infection or other cause of fluid build-up in the middle ear (14), these treatments might not immediately resolve the pain and discomfort caused by the buildup of fluid in the middle ear (14). In some instances, the most immediate relief will be felt by the patient if the fluid can be removed from the Eustachian tube (26).

Antibiotic treatment of middle ear infections may results in normal middle ear function within three to four weeks. During the healing period, the patient can experience varying degrees of ear pressure, popping, clicking, and fluctuation of hearing, occasionally with shooting pain in the ear (10). Resolution of the infection may leave the patient with uninfected fluid in the middle ear (14), localized in the Eustachian tube (26).

Fluid build-up caused by these types of infections may be treated surgically. The primary objective of surgical treatment of chronic serous otitis media is to reestablish ventilation of the middle ear (14), keeping the hearing at a normal level, and preventing recurrent infection that might damage the tympanic membrane (22) the and middle ear bones (34, 36, 38).

Figure 3:
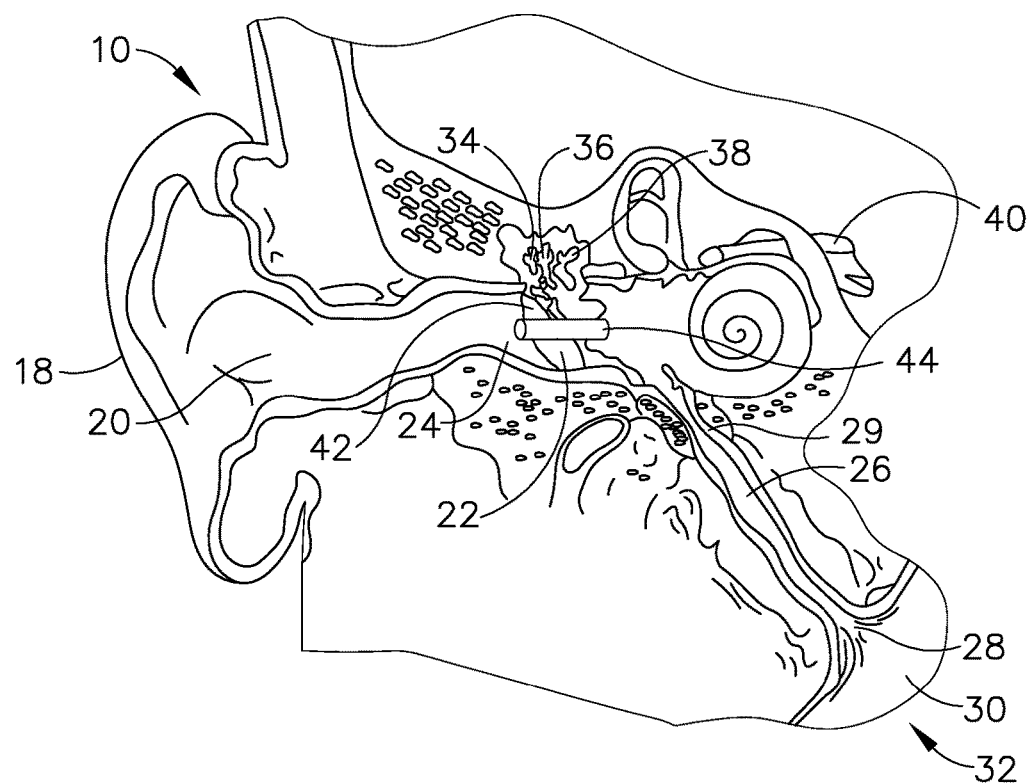
FIG. 3 depicts a cross-sectional front view of a human ear showing a surgical method for relieving fluid in the middle ear in which a ventilation tube is placed within an incision in the tympanic membrane.

For example, as shown in FIG. 3, a myringotomy can be performed to relieve fluid in the middle ear (14). A myringotomy is an incision (42) in the tympanic membrane (22) performed to remove fluid in the middle ear (14). A hollow plastic tube (44), referred to as a ventilation tube, is inserted and lodged in the incision (42) to prevent the incision (42) from healing and to ensure ventilation of the middle ear (14). The ventilation tube (44) temporarily takes the place of the Eustachian tube (26) in equalizing the pressure in the middle ear (14). The ventilation tube (44) may remain in place for three to nine months during which time the Eustachian tube (26) blockage subsides. When the ventilation tube (44) dislodges, the tympanic membrane (22) heals. The Eustachian tube (26) then resumes its normal pressure equalizing function.

Figure 4:
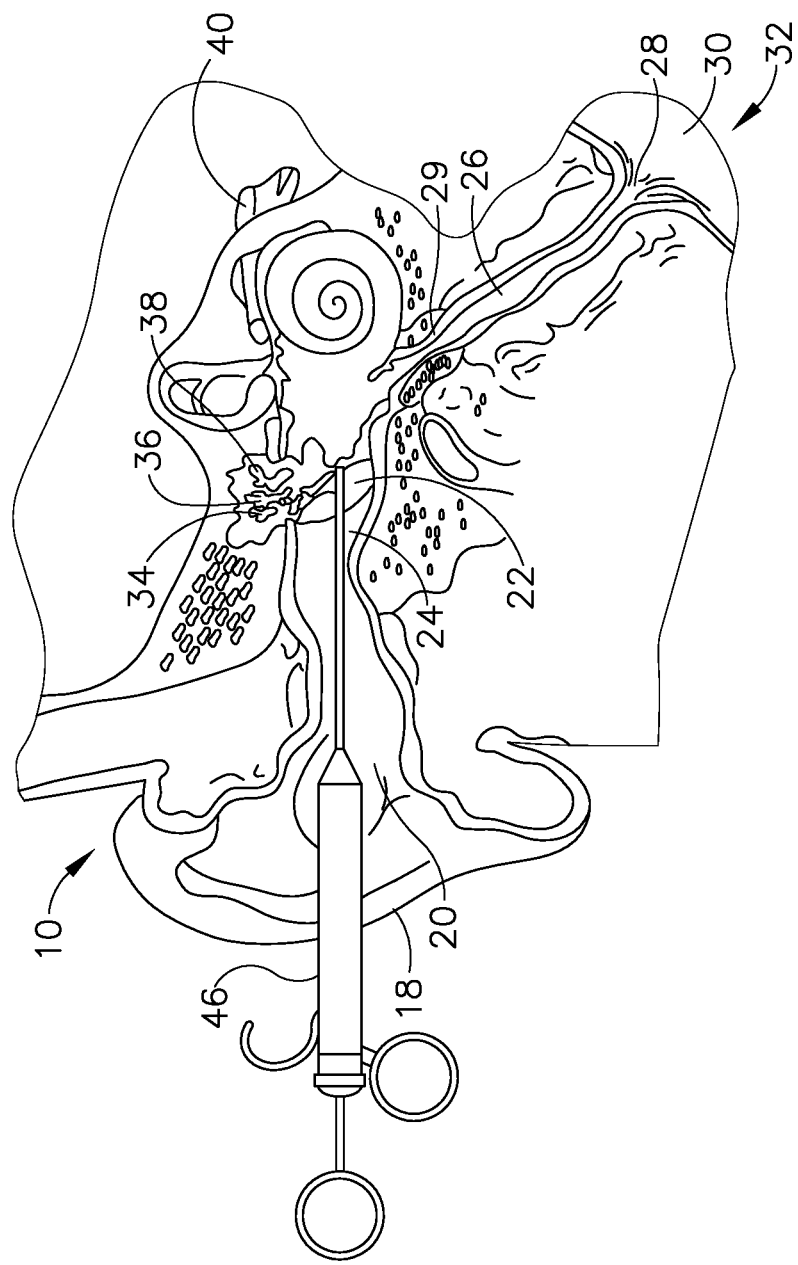
FIG. 4 depicts a cross-sectional front view of a human ear showing another surgical method for relieving fluid in the middle ear in which a syringe is shown having a needle perforating the tympanic membrane.

Another method of relieving the pressure in the middle ear (14) is shown in FIG. 4 in which a hypodermic needle (46) is driven through the tympanic membrane (22) through which any accumulated fluid can be withdrawn (e.g., from the upper portion of the Eustachian tube (26)).

The methods of FIGS. 3 and 4 involve rupturing the tympanic membrane (22) to relieve the fluid accumulation and pressure increase in the middle ear (14). Neither of these methods, in addition to the sometimes permanent puncture created in the tympanic membrane (22), is especially effective in removing all of the fluid in the Eustachian tube (26) since often the ostium (28) of the Eustachian tube (26) is blocked and dammed with fluid.

Figure 5:
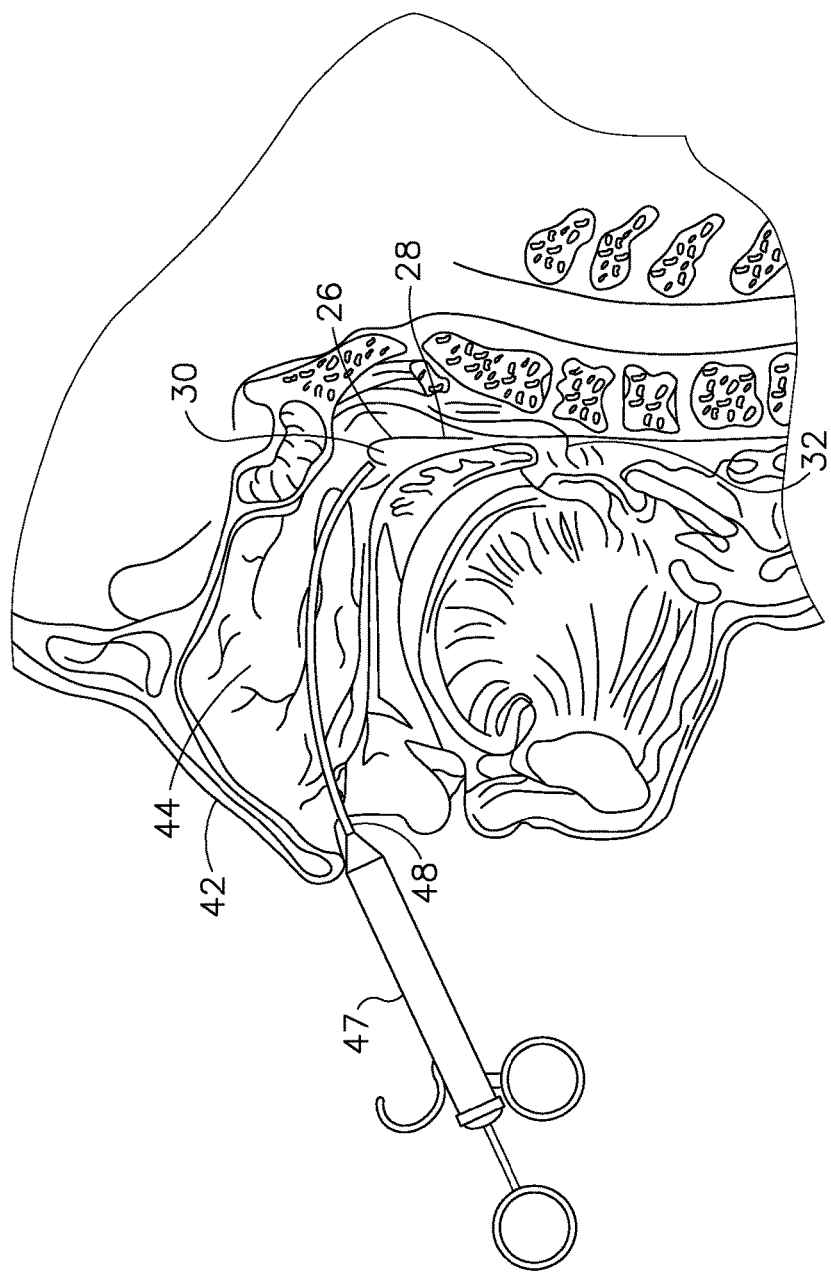
FIG. 5 depicts a cross-sectional side view of a human head showing a politzerization method for relieving fluid in the middle ear in which a syringe is shown having a flexible tip extending into the nose and/or throat area so that the tip abuts the pharyngeal ostium of the Eustachian tube while the nose is plugged.
Figure 6:
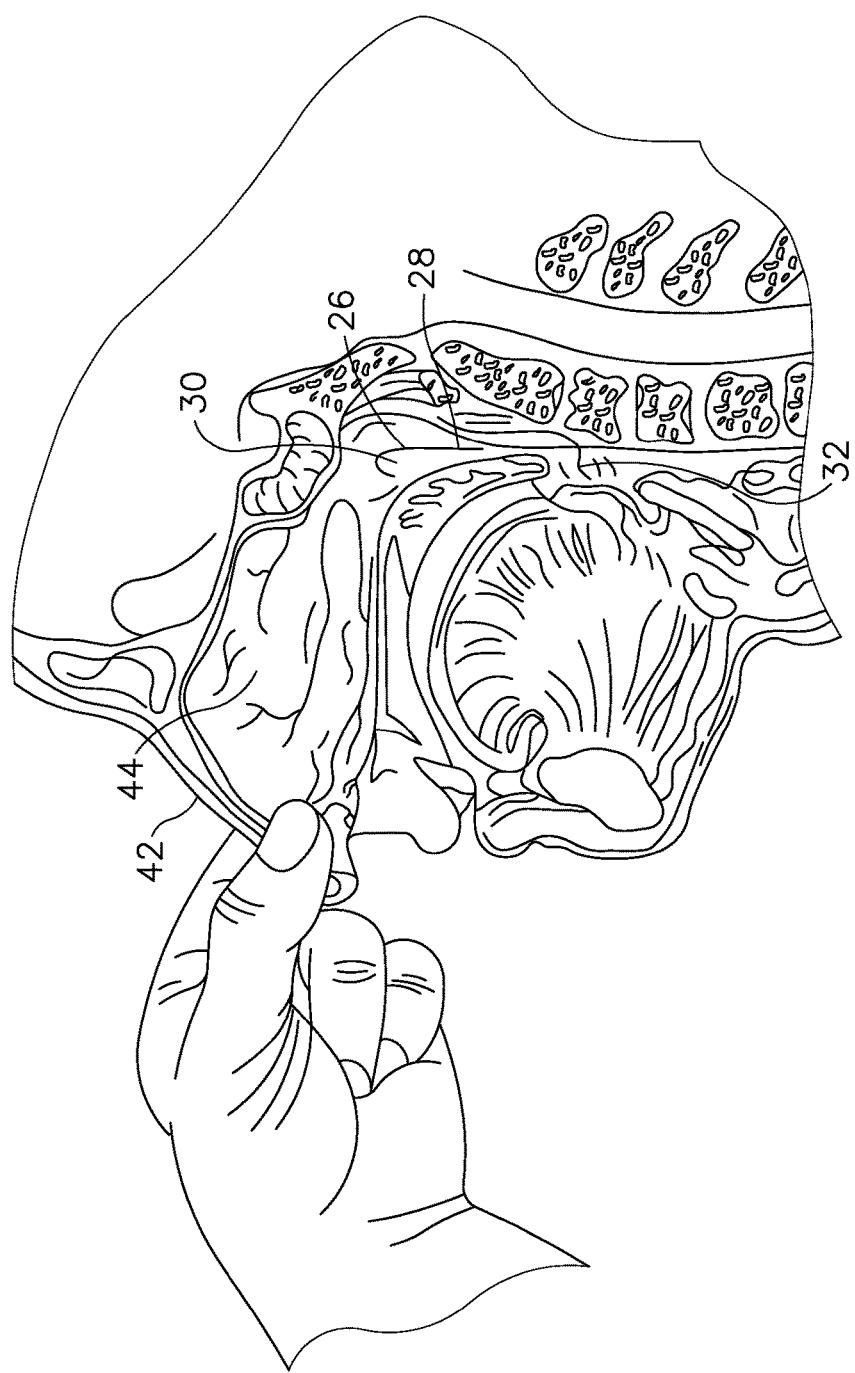
FIG. 6 depicts a cross-sectional side view of a human head showing the politzerization method of FIG. 5 while the nose is plugged.

In connection with the above surgical treatments of FIGS. 3 and 4, Eustachian tube (26) inflation is also employed to relieve the pressure build-up and fluid accumulation as shown in FIG. 5. The hypodermic syringe (47), shown with a flexible tip (48), is inserted into a nostril or into the mouth until the flexible tip (48) is positioned adjacent the ostium (28) of the Eustachian tube (26) in the nasopharynx region (30) of the throat (32). Air is blown through the flexible tip (48) via the syringe (47) into the obstructed Eustachian tube (26) and, thus, into the middle ear (14) to help relieve the congestion and reestablish middle ear ventilation. This procedure is often referred to as politzerization. Politzerization may be most effective when one of the nostrils is pinched shut (as shown in FIG. 6), while the patient simultaneously swallows. This procedure forces air into the Eustachian tube (26) and the middle ear (14). This technique may be good for opening the Eustachian tube (26) but it does not necessarily clear accumulated fluid away.

Another method for clearing the middle ear (14) (at least temporarily) is referred to as the "valsalva" maneuver, accomplished by forcibly blowing air into the middle ear (14) while holding the nose (42), often called "popping the ear." This method may also be good for opening the Eustachian tube (26) but it does not necessarily clear the accumulated fluid away either.

Typical disorders associated with the middle ear (14) and the Eustachian tube (26) may include perforated ear drums, tympanosclerosis, incus erosion, otitis media, cholesteotoma, mastoiditis, patulous Eustachian tube, and conductive hearing loss. To treat some of these disorders, ear surgery may be performed. Most ear surgery is microsurgery, performed with an operating microscope. Types of ear surgery include stapedectomy, tympanoplasty, myringotomy and ear tube surgery.

One of the simplest ear surgeries is the myringotomy or the incision of the tympanic membrane (22). However, ear surgery can also require the removal of the tympanic membrane (22) for the visualization of the middle ear (14). A surgeon may try to preserve the integrity of the tympanic membrane (22) by making incisions in the skin of the ear canal (20) and removing the tympanic membrane (22) as a complete unit. Alternatively, middle ear access may be achieved via the mastoids. This method approaches the middle ear (14) from behind the ear (10) and drills through the mastoid air cells to the middle ear (14). Whether the bony partition between the external ear (12) and the mastoid is removed or not depends on the extent of the disease. "Canal-wall-down" refers to the removal of this bony partition. "Canal-wall-up" refers to keeping this bony partition intact. The term "modified radical mastoidectomy" refers to an operation where this bony partition is removed and the tympanic membrane (22) and the middle ear bones (34, 36, 38) are reconstructed. A radical mastoidectomy is an operation where this bony partition is removed and the tympanic membrane (22), the malleus and the incus bones are permanently removed so that the inner lining of the large cholesteotoma sac can be safely cleaned. This operation is done when an extensive cholesteotoma is encountered or one that is adherent to the inner ear (16) or facial nerve.

Afflictions of the middle ear (14) and the Eustachian tube (26) may cause pain, discomfort and even hearing loss or permanent ear damage. Although a number of treatments have been developed, as described above each of them have shortcomings. Therefore, a need exists for improved methods and systems for accessing, diagnosing and treating target tissue regions within the middle ear (14) and the Eustachian tube (26). Ideally, such methods and systems would be minimally invasive and pose very little risk of damage to healthy ear tissue.

US Pat. Pub. No. 2010/0274188, entitled "Method and System for Treating Target Tissue Within the Eustachian Tube," published Oct. 28, 2010, now abandoned, the disclosure of which is incorporated by reference herein, is directed toward methods and systems for accessing, diagnosing, and treating target tissue regions within the middle ear (14) and the Eustachian tube (26). One particular method described in the publication is for dilating the Eustachian tube (26) of a patient. A guide catheter may be advanced through a nasal passage of the patient to position a distal end of the guide catheter at or near the ostium (28) of the Eustachian tube (26) of the patient. A distal portion of the guide catheter may include a bend having an angle between 30 degrees and 90 degrees. The distal portion may be more flexible than a proximal portion of the guide catheter. A guidewire may be advanced through the guide catheter such that a distal end of the guidewire enters the Eustachian tube (26). A dilation catheter may be advanced over the guidewire to position a dilator of the dilation catheter within the Eustachian tube (26). The dilator may be expanded to dilate the Eustachian tube (26). The dilation catheter and guidewire may then be removed from the patient.

II. Overview of Exemplary Dilation Catheter System

Improvement in the methods devices described above would provide a system for dilation of the Eustachian tube (26) that would be ergonomic and easy to use and would safely and effectively access the Eustachian tube (26). For instance, as shown in FIGS. 7A-10, a guide catheter (100) and a balloon dilation catheter (200), which are together operable by a single hand, may be used to safely and effectively access the Eustachian tube (26).

As shown in FIG. 7A, guide catheter (100) of the present example includes an elongate tubular shaft (102) that has a proximal end (104), a distal end (106), and a lumen (108) therebetween. Guide catheter (100) may have any suitable length, diameter, angle of bend, and location of the bend along the length of guide catheter (100), to facilitate accessing the Eustachian tube (26). In some embodiments, for example, guide catheter (100) may have a length between about 8 cm and about 20 cm, and more preferably between about 10 cm and about 15 cm, and in particular about 11 cm.

FIG. 7B is a cross-sectional view of elongate tubular shaft (102) of guide catheter (100). As can be seen, elongate tubular shaft (102) has an outer shaft tube (110), an inner shaft tube (112), and a lumen (108). Outer shaft tube (110) may be constructed of a stiff material such as stainless steel and inner shaft tube (112) may be constructed of a more flexible material such as a polymeric material including but not limited to nylon and further including a PTFE liner. Lumen (108) has a diameter of between about 2 mm and 3 mm, and preferably between about 2.5 mm and 2.6 mm such that balloon dilation catheter (200) can be easily inserted into lumen (108) for dilation of the Eustachian tube (26). The combination guide catheter (100) and balloon dilation catheter (200) make a compact system that is designed for a one-handed procedure. By compact, it is intended that the length of guide catheter (100) that is distal of a bend (122) in guide catheter (100) is between about 0.5 cm and 2.0 cm, often between about 1 and 2 cm, and in particular about 1 cm. The compactness may help reduce interference with other instruments, such as an endoscope that may be used to help in visualizing the positioning of the system.

A distal portion (120) of guide catheter (100) is shown in an enlarged view in FIG. 8. Distal portion (120) of guide catheter (100) may have a bend (122) with an angle between about 45 degrees and about 65 degrees, and more preferably between about 50 degrees and about 60 degrees, and in particular about 55 degrees to facilitate access into the Eustachian tube (26). Distal portion (120) of guide catheter (100) is made of a transparent material such as a polymer including but not limited to nylon and PTFE such that balloon dilation catheter (200) is visible within distal portion (120) and is more flexible than elongate shaft (102). A distal tip (124) of distal portion (120) of guide catheter (100) is made of polyether block amides (e.g., PEBAX® by Arkema) such that it provides for atraumatic access to the Eustachian tube (26), and may contain 20% barium sulfate or other similar radiopaque materials for visualizable access.

Referring again to FIG. 7A, a proximal portion (130) of guide catheter (100) includes a proximal hub (132) to aid in insertion of balloon dilation catheter (200) into the Eustachian Tube (26). Hub (132) has a larger diameter proximal end (134) and a smaller diameter middle section (136) to facilitate stabilization of guide catheter (100) in the nose (42), rotation of guide catheter (100) and insertion of balloon dilation catheter (200) as will be described in further detail below. Hub (132) is ergonomically designed for insertion, location and rotation with slight manipulations with one hand.

Another example of a guide catheter (300) is shown in FIG. 11. In this example, the proximal hub is a handle. Guide catheter (300) comprises an elongate shaft (302) and a handle (304) to aid in insertion of a balloon catheter (not shown) into the Eustachian Tube (26) in a manner similar to that described below with regard to guide catheter (100). In the example shown in FIG. 11, an actuator (306) comprises a slider that is attached to the balloon catheter that is contained within handle (304) and is slidably contained within elongate shaft (302) of guide catheter (300). In use, guide catheter (300) is inserted into the sinus of the patient and the balloon catheter is advanced into the Eustachian tube (26) via thumb or single finger advancement of actuator (306) along the length of a slot (310) formed in the handle (304). The advancement of the balloon catheter is continued until a visual marker indicates that advancement is complete, or until the enlarged tip of the balloon catheter abuts the isthmus of the Eustachian tube (26) or the actuator (306) abuts a distal end (308) of the slot (310) in the handle (304) and is therefore fully deployed.

Balloon dilation catheter (200) is shown in FIG. 9A. Balloon dilation catheter (200) generally includes an elongate shaft (202) having a proximal end (214) and a distal end (218). Balloon dilation catheter (200) further includes a balloon (204) on distal end (218) of elongate shaft (202). Balloon (204) may be a polymer balloon (compliant, semi-compliant or non-compliant). In some versions, balloon (204) may be a suitable non-compliant material such as but not limited to polyethylene terepthalate (PET), PEBAX®, nylon or the like. Balloon dilation catheter (200) may include any size of balloon (204) including but not limited to balloons of 2 mm to 8 mm in diameter, or of between about 5 mm and 6 mm (when inflated) and 12 mm to 24 mm in working length (for example 2 mm×12 mm, 3.5 mm×12 mm, 5 mm×16 mm, 5 mm×24 mm, 6 mm×16 mm, 6 mm×20 mm, 6 mm×24 mm, 7 mm×16 mm and 7 mm×24 mm). Balloon dilation catheter (200) generally includes a proximally located connection (230) for inflating/activating balloon (204).

Balloon (204) may be expanded to dilate the Eustachian tube (26) after it is placed in a desired location therein. For example, the Eustachian tube (26) includes a pharyngeal ostium (28), and balloon dilation catheter (200) may be advanced to position balloon (204) in the pharyngeal ostium (28). An endoscope may be used to assist in positioning balloon dilation catheter (200). The endoscope may be advanced through the nasal passage to view balloon dilation catheter (200). A marker (208) on elongate shaft (202) of balloon dilation catheter (200) can be viewed from the endoscope to approximate a location of balloon (204) relative to the opening of the Eustachian tube (26) based on a distance of marker (208) from a proximal end of balloon (204). Accordingly, balloon dilation catheter (200) can be moved to place marker (208) in a desired location before expansion of balloon (204) in the Eustachian tube (26).

Balloon dilation catheter (200) further includes an actuator (210). Actuator (210) has a proximal side (220) and a distal side (222). In the embodiment shown in FIG. 9A, actuator (210) is secured by an adhesive to elongate shaft (202). A portion (240) of elongate shaft (202) that is distal of actuator (210) is sufficiently stiff to be guided through the nasal cavity and into the Eustachian Tube (26) and is constructed of stainless steel and preferably includes a stainless steel hypotube. A portion (238) of elongate shaft (202) that is proximal of actuator (210) and a portion (250) that is distal of portion (240) is more flexible than portion (240) and is constructed of a polymeric material including but not limited to PEBAX®. In this way, proximal portion (238) of elongate shaft (202) will not interfere with the endoscope described above as it is advanced through the nasal passage such that balloon dilation catheter (200) can be easily viewed. Actuator (210) allows for easy, ergonomic one-handed advancement of balloon dilation catheter (200) through guide catheter (100) and into the Eustachian Tube (26). Actuator (210) may be used to advance or retract in alternative ways including but not limited to use of the thumb, the index finger, or a combination of fingers (i.e. the index and middle fingers) or the thumb and the index or middle finger.

Distal end (218) of balloon dilation catheter (200) further includes a tip (212) and a flexible shaft portion (250) that is constructed of a polymeric material including but not limited to PEBAX® that extends from the distal end of elongate shaft (202) to the proximal end of balloon (204). In the embodiment shown in FIG. 9A, tip (212) is a bulbous polymeric blueberry shaped tip that is atraumatic and is about 1.5 mm to 2 mm in length with an outer diameter of between about 2 mm and 3 mm. The smoothness and roundness of tip (212) facilitates advancement of balloon dilation catheter (200) by helping it glide smoothly through the Eustachian Tube (26). Tip (212) further acts as a safety stop. The isthmus (29) of the Eustachian tube (26), shown in FIG. 1 is approximately 1 mm in diameter. The diameter of tip (212) is larger than an outer diameter (233) of elongate shaft (202) shown in cross-section in FIG. 9B such that the size of tip (212) will prevent balloon dilation catheter (200) from passing through the isthmus (29) into the middle ear (14).

Balloon (204) may be held in location while in an expanded state for an extended period of time (e.g. several seconds or minutes). Balloon dilation catheter (200) may also deliver a substance to the Eustachian tube (26), such as one or more of the therapeutic or diagnostic agents described herein. Balloon (204) may also carry an expandable stent for delivery into the Eustachian tube (26) upon expansion of balloon (204). Balloon dilation catheter (200) and guide catheter (100) may be removed from the patient after balloon (204) has been deflated/unexpanded. The Eustachian tube (26) may then resume functioning, normally opening and closing to equalize atmospheric pressure in the middle ear (14) and protect the middle ear (14) from unwanted pressure fluctuations and loud sounds.

In use, guide catheter (100) may be advanced into a nostril and through a nasal cavity to position a distal end of guide catheter (100) at, in or near the ostium (28) of the Eustachian tube (26). In some versions, guide catheter (100) may be passed through a nostril to the Eustachian tube (26) on the ipsilateral (same side) of the head. In some other versions, guide catheter (100) may be passed through a nostril to the Eustachian tube (26) on the contralateral (opposite side) of the head. A guiding element such as a guidewire or illuminating fiber may be used to aid in accessing the Eustachian tube (26).

After guide catheter (100) is in a desired position, balloon catheter (200) is advanced through guide catheter (100) to position balloon (204) of balloon dilation catheter (200) within the Eustachian tube (26). The physician/user may place the index and middle fingers on either side of the smaller diameter middle section (136) of proximal hub (132) of guide catheter (100). The physician/user will then place the thumb on proximal side (220) of actuator (210) or within both sides of actuator (210) and will use the thumb to slide balloon dilation catheter (200) through guide catheter (100) to position balloon (204) within the Eustachian tube (26). Alternatively, the user may grasp proximal hub (132) of guide catheter (100) and use the index finger placed on proximal side (220) of the actuator (210) or in between distal side (222) and proximal side (220) of actuator (210) to advance balloon dilation catheter (200). The larger diameter tip (212) prevents balloon dilation catheter (200) from advancing too far into the middle ear (14). Further, distal side (222) of actuator (210) will bottom out against proximal end (104) of guide catheter (100), such that balloon dilation catheter (200) cannot advance any further. Actuator (210) prevents balloon dilation catheter (200) from reaching too far into the middle ear (14), which can cause damage to structures in the middle ear (14). Further actuator (210) can be positioned at the appropriate distance along elongate shaft (202) such that access to the Eustachian tube (26) may be from the contralateral or the ipsilateral side.

In some other instances, balloon catheter (200) is advanced into a nostril of a patient without the use of guide catheter (100). Balloon (204) of balloon dilation catheter (200) is placed within the Eustachian tube (26). The physician/user will advance balloon dilation catheter (200) until proximal side (220) of actuator (210) is adjacent the patient's nostril. Distal side (222) of actuator (210) will bottom out against the patient's nostril, such that balloon dilation catheter (200) cannot advance any further. Actuator (210) prevents balloon dilation catheter (210) from reaching too far into the middle ear (14), which can cause damage to structures in the middle ear (14). Further, actuator (210) can be positioned at the appropriate distance along elongate shaft (202) such that access to the Eustachian tube (26) may be from the contralateral or the ipsilateral side.

Following placement of balloon dilation catheter (200) into the desired position, any number of procedures may be carried out. Elongate shaft (202) contains adjacent dual lumen tubing (see FIG. 9B). By adjacent dual lumen tubing, it is intended that the lumens are next to each other but are spaced apart, one from one another. Inflation lumen (232) is used for inflation of balloon (204) with water, contrast medium, or saline through inflation port (230) to a pressure of between about 3 and 15 atmospheres, or of between about 6 and 12 atmospheres. Injection lumen (234) permits the optional injection of water, medicament, or even the introduction of a guidewire through injection port (236) at proximal end (216) of proximal connector (206). In order to ensure that inflation port (230) is used for balloon inflation only, inflation port (230) and injection port (236) may optionally comprise different type connectors. For example, inflation port (230) may comprise a female connector whereas injection port (236) comprises a male connector or vice versa. Alternatively, injection port (236) may comprise a right-handed thread connected and inflation port (230) may comprise a left-handed thread connector or vice versa. It may be desirable to inject solutions containing contrast agents, pharmaceutically acceptable salt or dosage form of an antimicrobial agent (e.g. antibiotic, antiviral, anti-parasitic, antifungal, etc.), an anesthetic agent with or without a vasoconstriction agent (e.g. Xylocaine with or without epinephrine, Tetracaine with or without epinephrine, etc.), an analgesic agent, a corticosteroid or other anti-inflammatory (e.g. an NSAID), a decongestant (e.g. vasoconstrictor), a mucus thinning agent (e.g. an expectorant or mucolytic), a surfactant, an agent that prevents or modifies an allergic response (e.g. an antihistamine, cytokine inhibitor, leucotriene inhibitor, IgE inhibitor, immunomodulator), an allergen or another substance that causes secretion of mucous by tissues, hemostatic agents to stop bleeding, antiproliferative agents, cytotoxic agents (e.g. alcohol), biological agents such as protein molecules, stem cells, genes or gene therapy preparations, or the like.

Some nonlimiting examples of antimicrobial agents that may be used include acyclovir, amantadine, aminoglycosides (e.g., amikacin, gentamicin and tobramycin), amoxicillin, amoxicillinlclavulanate, amphotericin B, ampicillin, ampicillinlsulbactam, atovaquone, azithromycin, cefazolin, cefepime, cefotaxime, cefotetan, cefpodoxime, ceflazidime, ceflizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscamet, ganciclovir, atifloxacin, imipenemlcilastatin, isoniazid, itraconazole, ketoconazole, metronidazole, nafcillin, nafcillin, nystatin, penicillin, penicillin G, pentamidine, piperacillinitazobactam, rifampin, quinupristindalfopristin, ticarcillinlclavulanate, trimethoprimlsulfamethoxazole, valacyclovir, vancomycin, mafenide, silver sulfadiazine, mupirocin (e.g., Bactroban, Glaxo SmithKline, Research Triangle Park, N.C.), nystatin, triamcinolonelnystatin, clotrimazolelbetamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulphonated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acid form); non-pathogenic or "friendly" microbes that cause the production of hydrogen peroxide or other substances that kill or inhibit the growth of pathogenic microbes (e.g., *lactobacillus*); antimicrobial proteins or peptides such as those described in U.S. Pat. No. 6,716,813, entitled "Use of Antimicrobial Proteins and Peptides for the Treatment of Otitis Media and Paranasal Sinusitis," issued Apr. 6, 2004, the disclosure of which is incorporated by reference herein, or antimicrobial metals (e.g., colloidal silver).

Additionally or alternatively, in some applications where it is desired to treat or prevent inflammation the substances delivered may include various steroids or other anti-inflammatory agents (e.g., nonsteroidal anti-inflammatory agents or NSAIDS), analgesic agents or antipyretic agents. For example, corticosteroids that have previously administered by intranasal 10 administration may be used, such as beclomethasone (Vancenase® or Beconase), flunisolide (Nasalid®), fluticasone proprionate (Flonase®), triamcinolone acetonide (Nasacort®), budesonide (Rhinocort Aqua®), loterednol etabonate (Locort) and mometasone (Nasonex®). Other salt forms of the aforementioned corticosteroids may also be used. Also, other non-limiting examples of steroids that may be useable include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexarnethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as mmesulide).

Additionally or alternatively, in some applications, such as those where it is desired to treat or prevent an allergic or immune response and/or cellular proliferation, the substances delivered may include: various cytokine inhibitors such as humanized anti-cytokine antibodies, anti-cytokine receptor antibodies, recombinant (new cell resulting from genetic recombination) antagonists, or soluble receptors; various leucotriene modifiers such as zafirlukast, montelukast and zileuton; immunoglobulin E (IgE) inhibitors such as Omalizumab (an anti-IgE monoclonal antibody formerly called rhu Mab-E25) and secretory leukocyte protease inhibitor); and SYK Kinase inhibitors such as an agent designated as "R-112" manufactured by Rigel Pharmaceuticals, Inc, South San Francisco, Calif.

Additionally or alternatively, in some applications, such as those where it is desired to shrink mucosal tissue, cause decongestion, or effect hemostasis, the substances delivered may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered may include various mucolytics or other agents that modify the viscosity or consistency of mucous or mucoid secretions, including but not limited to acetylcysteine. In one particular embodiment, the substance delivered may comprise a combination of an anti-inflammatory agent (e.g. a steroid or an NSAID) and a mucolytic agent.

Additionally or alternatively, in some applications such as those where it is desired to prevent or deter histamine release, the substances delivered may include various mast cell stabilizers or drugs which prevent the release of histamine such as cromolyn (e.g., Nasal Chroma) and nedocromil.

Additionally or alternatively, in some applications such as those where it is desired to prevent or inhibit the effect of histamine, the substances delivered may include various antihistamines such as azelastine (e.g., Astylin) diphenhydramine, loratidine, etc.

Additionally or alternatively, in some embodiments such as those where it is desired to dissolve, degrade, cut, break or remodel bone or cartilage, the substances delivered may include substances that weaken or modify bone and/or cartilage to facilitate other procedures wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CGN), trypsin, trypsinlLEDTA, hyaluronidase, and tosyllysylchloromethane (TLCM).

Additionally or alternatively, in some applications such as those wherein it is desired to treat a tumor or cancerous lesion, the substances delivered may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other antitumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-I, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, 1MC-IC11, 1M862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmetteguerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogslcongeners and derivatives of such compounds as well as other antitumor agents not listed here.

Additionally or alternatively, in some applications such as those where it is desired to grow new cells or to modify existing cells, the substances delivered may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired, cells that participate in or effect mucogenesis or ciliagenesis, etc.

In some instances, a local anesthetic, such as Lidocaine is injected through injection lumen (234) prior to dilation of the Eustachian tube (26). Injection lumen (234) can be used for venting during dilation so that pressure in the middle ear (14) does not increase or decrease.

Figure 12:
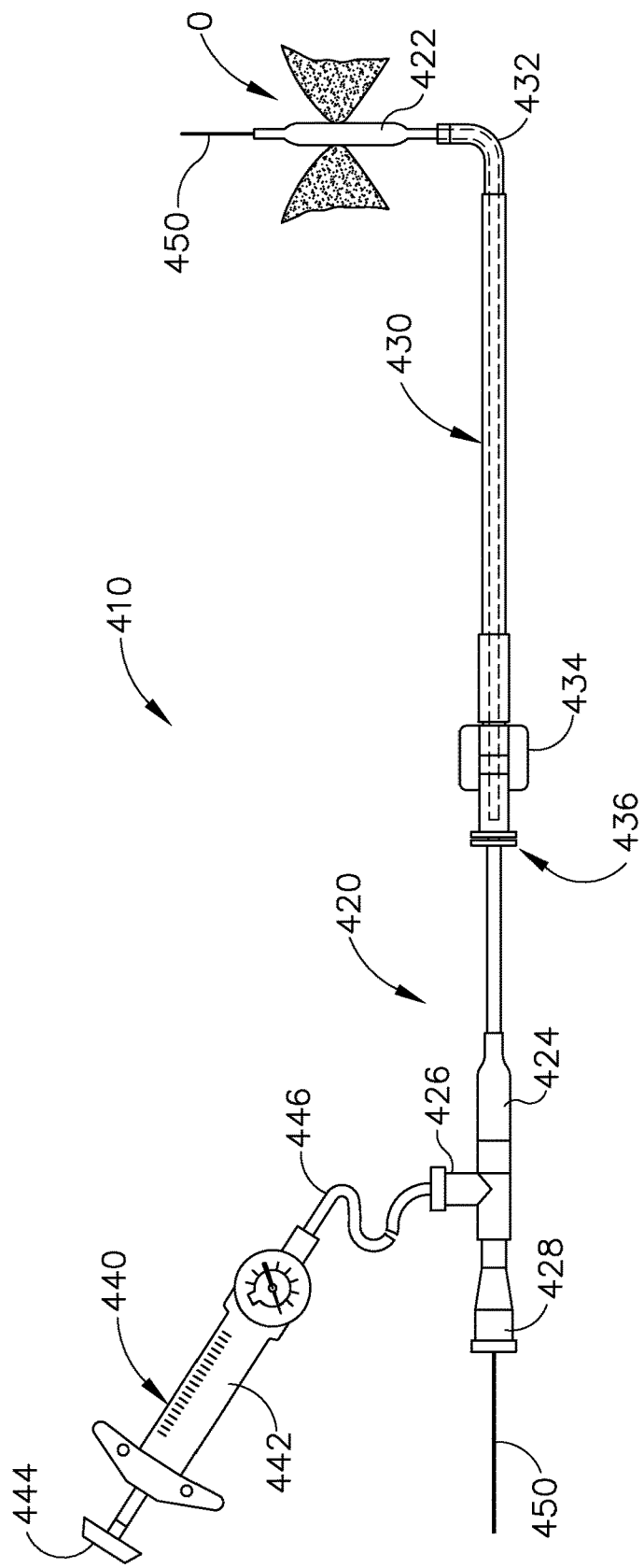
FIG. 12 depicts a side elevational view of an exemplary dilation catheter system.

FIG. 12 shows another exemplary dilation catheter system (410) that may be used to dilate the Eustachian tube (26); or to dilate some other anatomical passageway (e.g., within the ear, nose, or throat, etc.). Dilation catheter system (410) of this example comprises a balloon dilation catheter (420), a guide catheter (430), an inflator (440), and a guidewire (450). It should be understood that dilation catheter (420) may be viewed as a variation of dilation catheter (200) described above. Similarly, guide catheter (430) may be viewed as a variation of guide catheter (100) described above. By way of example only, dilation catheter system (410) may be configured in accordance with at least some of the teachings of U.S. Pat. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. In some versions, at least part of dilation catheter system (410) is configured similar to the Relieva® Spin Balloon Sinuplasty™ System by Acclarent, Inc. of Menlo Park, Calif.

The distal end of balloon dilation catheter (420) includes a balloon (422). The proximal end of balloon dilation catheter (420) includes a grip (424), which has a lateral port (426) and an open proximal end (428). Balloon dilation catheter (420) includes a first lumen (not shown) that provides fluid communication between lateral port (426) and the interior of balloon (422). Balloon dilation catheter (420) also includes a second lumen (not shown) that extends from open proximal end (428) to an open distal end that is distal to balloon (422). This second lumen is configured to slidably receive guidewire (450). The first and second lumens of balloon dilation catheter (420) are fluidly isolated from each other. Thus, balloon (422) may be selectively inflated and deflated by communicating fluid along the first lumen via lateral port (426) while guidewire (450) is positioned within the second lumen. In some versions, balloon dilation catheter (420) is configured similar to the Relieva Ultirra™ Sinus Balloon Catheter by Acclarent, Inc. of Menlo Park, Calif. In some other versions, balloon dilation catheter (420) is configured similar to the Relieva Solo Pro™ Sinus Balloon Catheter by Acclarent, Inc. of Menlo Park, Calif. Other suitable forms that balloon dilation catheter (420) may take will be apparent to those of ordinary skill in the art in view of the teachings herein.

Guide catheter (430) of the present example includes a bent distal end (432) and a grip (434) at its proximal end. Grip (434) has an open proximal end (436). Guide catheter (430) defines a lumen that is configured to slidably receive balloon dilation catheter (420), such that guide catheter (430) may guide balloon (422) out through bent distal end (432). In some versions, guide catheter (430) is configured similar to the Relieva Flex™ Sinus Guide Catheter by Acclarent, Inc. of Menlo Park, Calif. Other suitable forms that guide catheter (430) may take will be apparent to those of ordinary skill in the art in view of the teachings herein.

Inflator (440) of the present example comprises a barrel (442) that is configured to hold fluid and a plunger (444) that is configured to reciprocate relative to barrel (442) to selectively discharge fluid from (or draw fluid into) barrel (442). Barrel (442) is fluidly coupled with lateral port (426) via a flexible tube (446). Thus, inflator (440) is operable to add fluid to balloon (422) or withdraw fluid from balloon (422) by translating plunger (444) relative to barrel (442). In the present example, the fluid communicated by inflator (440) comprises saline, though it should be understood that any other suitable fluid may be used. There are various ways in which inflator (440) may be filled with fluid (e.g., saline, etc.). By way of example only, before flexible tube (446) is coupled with lateral port (426), the distal end of flexible tube (446) may be placed in a reservoir containing the fluid. Plunger (444) may then be retracted from a distal position to a proximal position to draw the fluid into barrel (442). Inflator (440) may then be held in an upright position, with the distal end of barrel (442) pointing upwardly, and plunger (444) may then be advanced to an intermediate or slightly distal position to purge any air from barrel (442). The distal end of flexible tube (446) may then be coupled with lateral port (426).

As best seen in FIGS. 13 and 14, guidewire (450) of the present example comprises a coil (452) positioned about a core wire (454). An illumination fiber (456) extends along the interior of core wire (454) and terminates in an atraumatic lens (458). A connector (455) at the proximal end of guidewire (450) enables optical coupling between illumination fiber (456) and a light source (4 not shown). Illumination fiber (456) may comprise one or more optical fibers. Lens (458) is configured to project light when illumination fiber (456) is illuminated by the light source, such that illumination fiber (456) transmits light from the light source to the lens (458). In some versions, the distal end of guidewire (450) is more flexible than the proximal end of guidewire (450). Guidewire (450) has a length enabling the distal end of guidewire (450) to be positioned distal to balloon (422) while the proximal end of guidewire (450) is positioned proximal to grip (424). Guidewire (450) may include indicia along at least part of its length (4 e.g., the proximal portion) to provide the operator with visual feedback indicating the depth of insertion of guidewire (450) relative to balloon dilation catheter (420). By way of example only, guidewire (450) may be configured in accordance with at least some of the teachings of U.S. Pat. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. In some versions, guidewire (450) is configured similar to the Relieva Luma Sentry™ Sinus Illumination System by Acclarent, Inc. of Menlo Park, Calif. Other suitable forms that guidewire (450) may take will be apparent to those of ordinary skill in the art in view of the teachings herein.

In an exemplary dilation procedure, guide catheter (430) may first be positioned near the targeted anatomical passageway, such as the ostium (28). Balloon (422) and the distal end of guidewire (450) may be positioned within or proximal to bent distal end (432) of guide catheter (430) at this stage. Guide catheter (430) is initially inserted into the nose of the patient and is advanced to a position that is within or near the ostium (40) to be dilated. This positioning of guide catheter (430) may be performed under visualization provided by an endoscope such as endoscope (460) described below. After guide catheter (430) has been positioned, the operator may advance guidewire (450) distally through guide catheter (430) such that a distal portion of the guidewire (450) passes through the sinus ostium (O) and into the sinus cavity. The operator may illuminate illumination fiber (456) and lens (458), which may provide transcutaneous illumination through the patient's face to enable the operator to visually confirm positioning of the distal end of guidewire (450) with relative ease.

With guide catheter (430) and guidewire (450) suitably positioned, balloon dilation catheter (420) is advanced along guidewire (450) and through bent distal end (432) of guide catheter (430), with balloon (422) in a non-dilated state until balloon (422) is positioned within the ostium (28) (or some other targeted anatomical passageway). After balloon (422) has been positioned within the ostium (O), balloon (422) may be inflated, thereby dilating the ostium. To inflate balloon (422), plunger (444) may be actuated to push saline from barrel (442) of inflator (440) through balloon dilation catheter (420) into balloon (422). The transfer of fluid expands balloon (422) to an expanded state to open or dilate the ostium (O), such as by remodeling the bone, etc., forming ostium (O). By way of example only, balloon (422) may be inflated to a volume sized to achieve about 10 to about 12 atmospheres. Balloon (422) may be held at this volume for a few seconds to sufficiently open the ostium (O) (or other targeted anatomical passageway). Balloon (422) may then be returned to a non-expanded state by reversing plunger (444) of inflator (440) to bring the saline back to inflator (440). Balloon (422) may be repeatedly inflated and deflated in different ostia and/or other targeted anatomical passageways. Thereafter, balloon dilation catheter (420), guidewire (450), and guide catheter (430) may be removed from the patient.

In some instances, it may be desirable to irrigate the sinus and paranasal cavity after balloon dilation catheter (420) has been used to dilate an ostium (O). Such irrigation may be performed to flush out blood, etc. that may be present after the dilation procedure. By way of example only, such irrigation may be carried out in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, the disclosure of which is incorporated by reference herein. An example of an irrigation catheter that may be fed through guide catheter (430) to reach the irrigation site after removal of balloon dilation catheter (420) is the Relieva Vortex® Sinus Irrigation Catheter by Acclarent, Inc. of Menlo Park, Calif. Another example of an irrigation catheter that may be fed through guide catheter (430) to reach the irrigation site after removal of balloon dilation catheter (420) is the Relieva Ultirra® Sinus Irrigation Catheter by Acclarent, Inc. of Menlo Park, Calif. Of course, irrigation may be provided in the absence of a dilation procedure; and a dilation procedure may be completed without also including irrigation.

As noted above, an endoscope (460) may be used to provide visualization within an anatomical passageway (e.g., within the nasal cavity, etc.) during a process of using dilation catheter system (410). As shown in FIGS. 15 and 16, endoscope (460) of the present example comprises a body (462) and a rigid shaft (464) extending distally from body (462). The distal end of shaft (464) includes a curved transparent window (466). A plurality of rod lenses and light transmitting fibers may extend along the length of shaft (464). A lens is positioned at the distal end of the rod lenses and a swing prism is positioned between the lens and window (466). The swing prism is pivotable about an axis that is transverse to the longitudinal axis of shaft (464). The swing prism defines a line of sight that pivots with the swing prism. The line of sight defines a viewing angle relative to the longitudinal axis of shaft (464). This line of sight may pivot from approximately 0 degrees to approximately 120 degrees, from approximately 10 degrees to approximately 90 degrees, or within any other suitable range. The swing prism and window (466) also provide a field of view spanning approximately 60 degrees (4 with the line of sight centered in the field of view). Thus, the field of view enables a viewing range spanning approximately 180 degrees, approximately 140 degrees, or any other range, based on the pivot range of the swing prism. Of course, all of these values are mere examples.

Body (462) of the present example includes a light post (470), an eyepiece (472), a rotation dial (474), and a pivot dial (476). Light post (470) is in communication with the light transmitting fibers in shaft (464) and is configured to couple with a source of light, to thereby illuminate the site in the patient distal to window (466). Eyepiece (472) is configured to provide visualization of the view captured through window (466) via the optics of endoscope (460). It should be understood that a visualization system (e.g., camera and display screen, etc.) may be coupled with eyepiece (472) to provide visualization of the view captured through window (466) via the optics of endoscope (460). Rotation dial (474) is configured to rotate shaft (464) relative to body (462) about the longitudinal axis of shaft (464). It should be understood that such rotation may be carried out even while the swing prism is pivoted such that the line of sight is non-parallel with the longitudinal axis of shaft (464). Pivot dial (476) is coupled with the swing prism and is thereby operable to pivot the swing prism about the transverse pivot axis. Indicia (478) on body (462) provide visual feedback indicating the viewing angle. Various suitable components and arrangements that may be used to couple rotation dial (474) with the swing prism will be apparent to those of ordinary skill in the art in view of the teachings herein. By way of example only, endoscope (460) may be configured in accordance with at least some of the teachings of U.S. Pat. Pub. No. 2010/0030031, entitled "Swing Prism Endoscope," published Feb. 4, 2010, now abandoned, the disclosure of which is incorporated by reference herein. In some versions, endoscope (460) is configured similar to the Acclarent Cyclops™ Multi-Angle Endoscope by Acclarent, Inc. of Menlo Park, Calif. Other suitable forms that endoscope (460) may take will be apparent to those of ordinary skill in the art in view of the teachings herein.

III. Exemplary Guide Catheter with Measurement Markings

Figure 17:
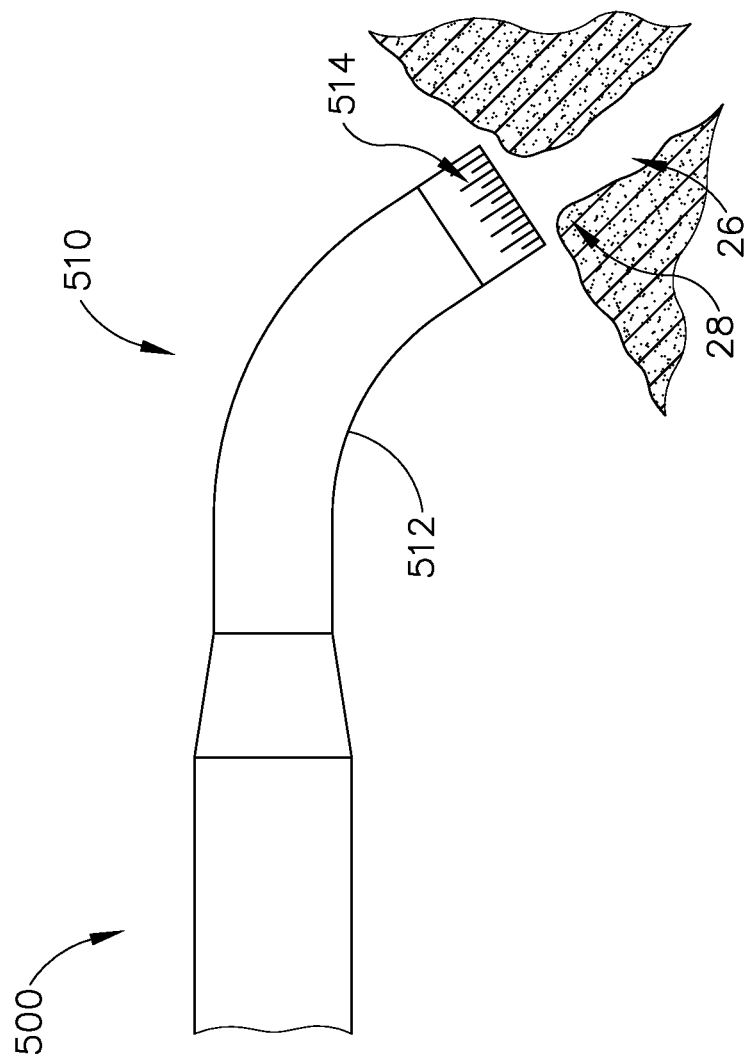
FIG. 17 depicts a detailed side elevational view of the distal end of the guide catheter of FIG. 7A having measurement markings.

FIG. 17 shows an exemplary guide catheter (500) suitable for use with dilation catheter system (410) described above. Guide catheter (500) of the present example is configured to operate substantially similar to guide catheters (100, 300, 430) described above except for the differences discussed below. In particular, guide catheter (500) is operable to direct balloon dilation catheters (200, 420) toward the Eustachian tube (26) (or any other anatomical passageway (e.g., within the ear, nose, or throat, etc.)) such that balloon dilation catheters (200, 420) may safely and effectively access the Eustachian tube (26).

As shown in FIG. 17, a distal portion (510) of guide catheter (500) includes a bend (512) with an angle between about 45 degrees and about 65 degrees, and more preferably between about 50 degrees and about 60 degrees, and in particular about 55 degrees to facilitate access into the Eustachian tube (26). Distal portion (510) of guide catheter (500) may be made of a transparent material such as a polymer including but not limited to nylon and PTFE such that balloon dilation catheters (200, 420) are visible within distal portion (510). Distal portion (510) of guide catheter (510) comprises an atraumatic distal tip (514). Distal tip (514) may be made of PEBAX® such that it provides for atraumatic access to the Eustachian tube (26), and may contain 20% barium sulfate or other similar radiopaque materials for visualizable access. Distal tip (514) of the present example includes a plurality of measurement markings (516) positioned about an exterior surface of distal tip (514). Measurement markings (516) may extend completely about the exterior surface of distal tip (514) in an angularly spaced array. Alternatively, measurement markings (516) may extend only partially about the exterior surface of distal tip (514). As shown in FIG. 17, when viewed via an endoscope, with distal tip (514) of distal portion (510) of guide catheter (500) positioned adjacent to the ostium (28) of the Eustachian tube (26), the user is able to measure a width of the ositum (28) and/or the Eustachian tube (26). Such measurements may be taken before and/or after dilation of the Eustachian tube (26) to ensure dilation of the Eustachian tube (26).

IV. Exemplary Balloon with Measurement Markings

Figure 18:
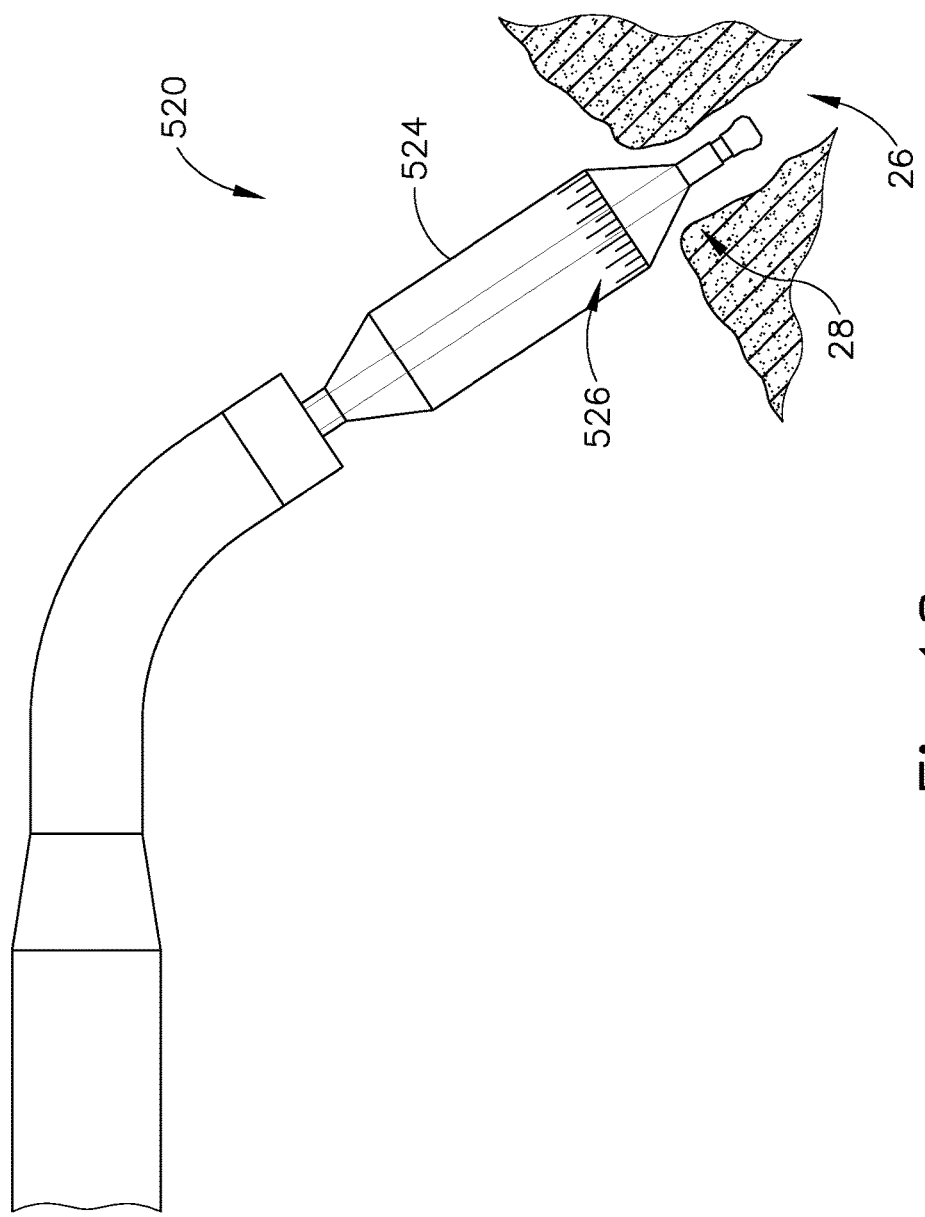
FIG. 18 depicts a detailed side elevational view of the distal end of the balloon dilation catheter of FIG. 9A having measurement markings.
Figure 19:
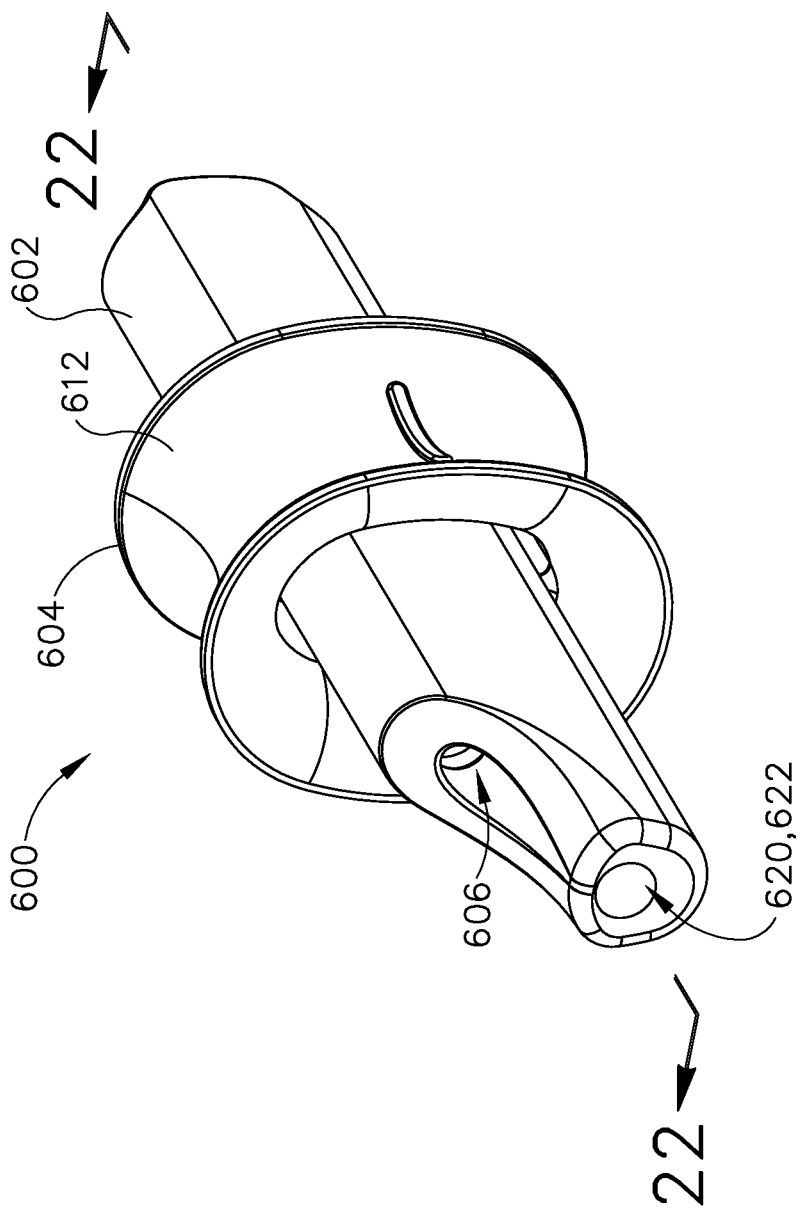
FIG. 19 depicts a perspective view of an exemplary handle suitable for use with the dilation catheter system of FIG. 12.

FIG. 18 shows an exemplary balloon dilation catheter (520) suitable for use with dilation catheter system (410) described above. Balloon dilation catheter (520) of the present example is configured to operate substantially similar to balloon dilation catheters (200, 420) described above except for the differences discussed below. In particular, balloon dilation catheter (520) is operable to safely and effectively access and dilate the Eustachian tube (26) (or any other anatomical passageway (e.g., within the ear, nose, or throat, etc.)).

Balloon dilation catheter (520) includes a balloon (524). Balloon (524) may be a polymer balloon (compliant, semi-compliant or non-compliant). In one embodiment, balloon (524) may be a suitable non-compliant material such as but not limited to polyethylene terepthalate (PET), PEBAX®, nylon or the like. Balloon dilation catheter (520) may include any size of balloon (524) including but not limited to balloons of 2 mm to 8 mm in diameter, or of between about 5 mm and 6 mm (when inflated) and 12 mm to 24 mm in working length (for example 2 mm×12 mm, 3.5 mm×12 mm, 5 mm×16 mm, 5 mm×24 mm, 6 mm×16 mm, 6 mm×20 mm, 6 mm×24 mm, 7 mm×16 mm and 7 mm×24 mm).

As shown in FIG. 18, balloon (524) of the present example includes a plurality of measurement markings (526) positioned about an exterior surface of distal balloon (524). Measurement markings (526) may extend completely about the exterior surface balloon (524) in an angularly spaced array. Alternatively, measurement markings (526) may extend only partially about the exterior surface of balloon (524). As shown in FIG. 18, when viewed via an endoscope, with balloon (524) positioned adjacent to the ostium (28) of the Eustachian tube (26), the user is able to measure a width of the ositum (28) and/or the Eustachian tube (26). Such measurements may be taken before and/or after dilation of the Eustachian tube (26) to ensure dilation of the Eustachian tube (26).

V. Exemplary Single-Hand-Use Handle

As mentioned above, it may be desirable to provide a system for dilation of the Eustachian tube (26) that would be ergonomic and easy to use and would safely and effectively access the Eustachian tube (26). For instance, it may be desirable to provide a handle operable to allow a user to single-handedly operate dilation catheter system (410) described above. In particular, it may be desirable to provide a handle operable to combine guide catheters (100, 300, 430, 500), balloon dilation catheters (200, 420, 520), and/or endoscope (460) in such a manner as to allow a user to maneuver and operate each element using only a single hand. Various examples of such handles will be described in greater detail below; while other examples will be apparent to those of ordinary skill in the art in view of the teachings herein. While the following examples are provided in the context of dilating a Eustachian tube (26) it should be understood that the same examples may be readily applied to the context of dilating ostia of paranasal sinuses, the frontal recess, and/or other anatomical passageways associated with the ear, nose, and throat.

Figure 20:
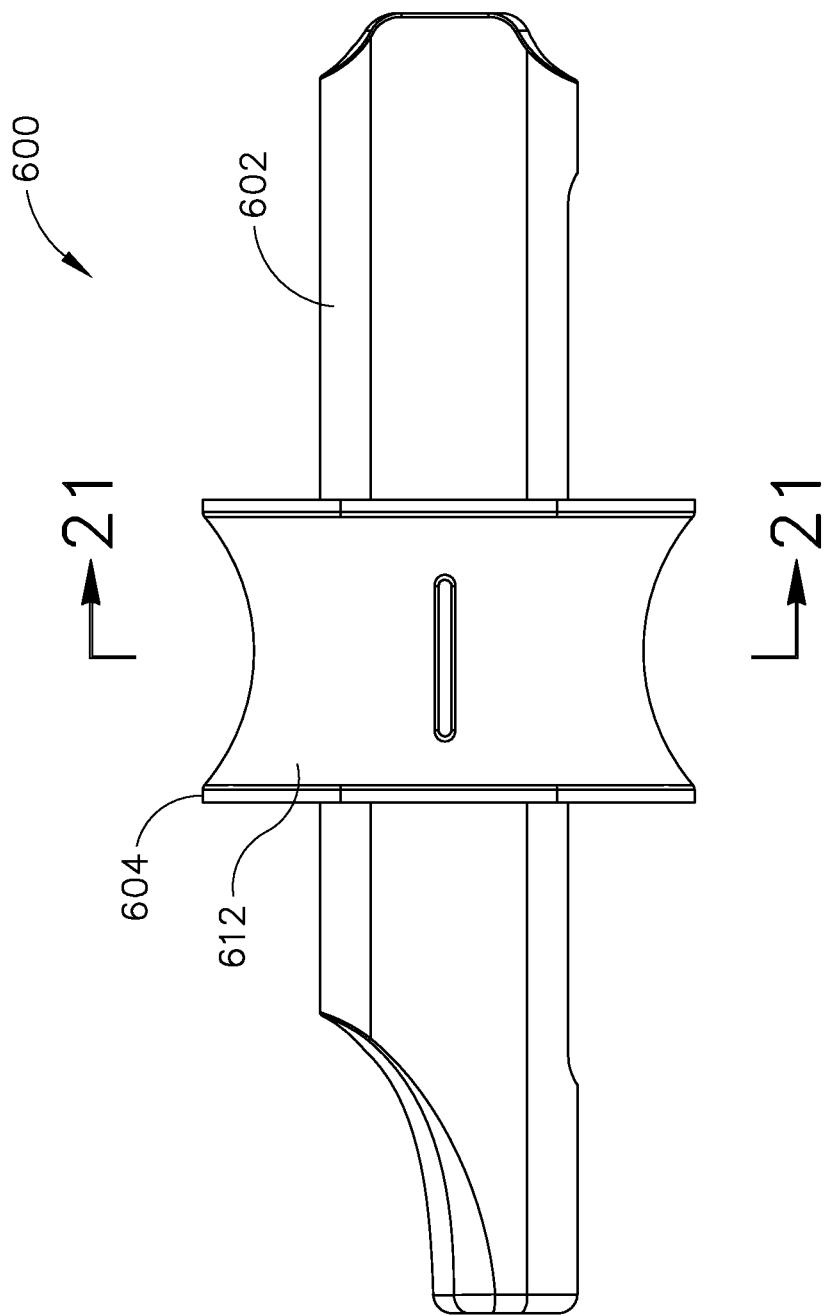
FIG. 20 depicts a side elevational view of the handle of FIG. 19.
Figure 21:
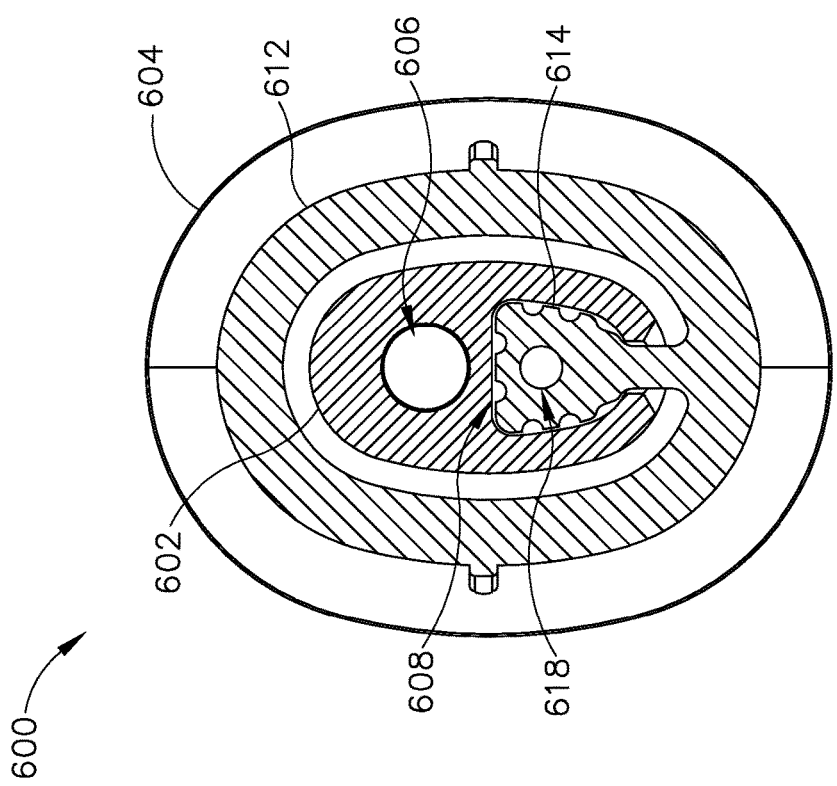
FIG. 21 depicts a cross-sectional front view of the handle of FIG. 19 taken along line 21-21 of FIG. 20.
Figure 22:
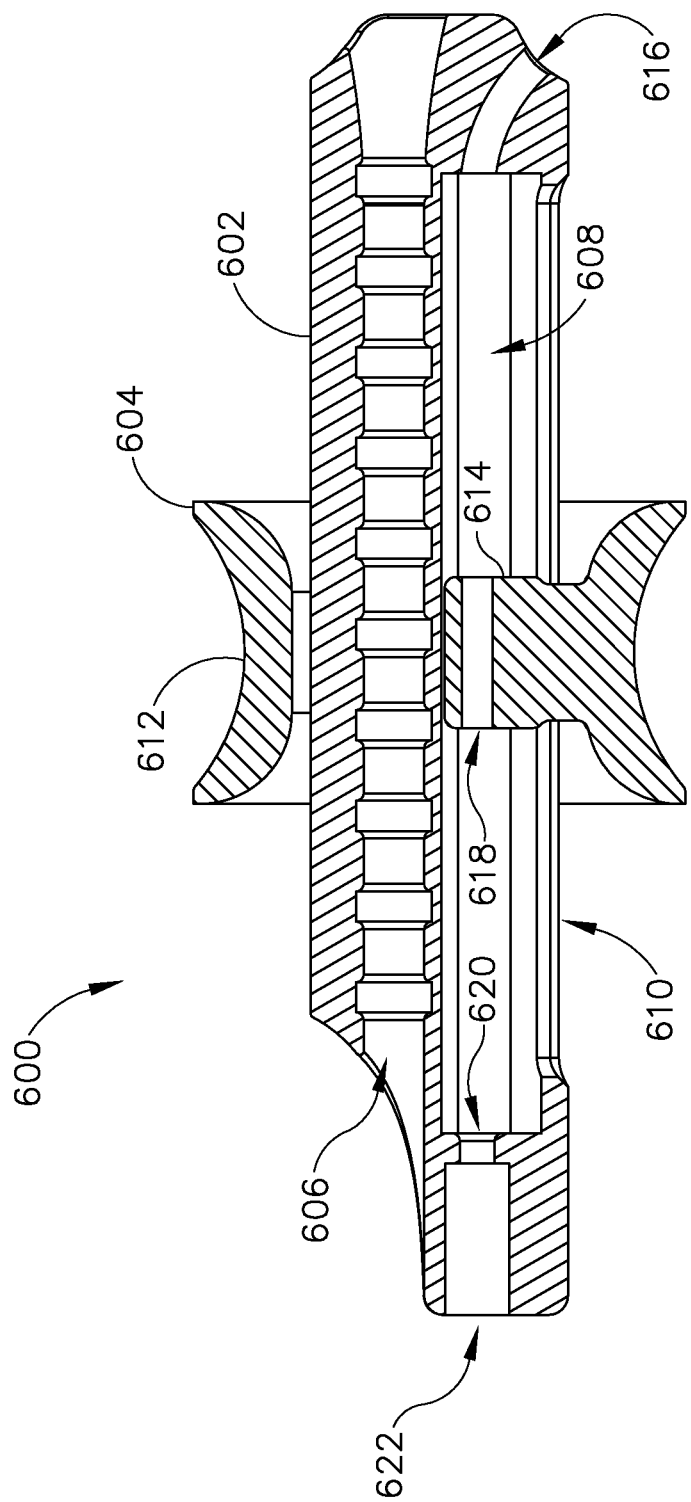
FIG. 22 depicts a cross-sectional side view of the handle of FIG. 19 taken along line 22-22 of FIG. 19.

FIGS. 19-23C show an exemplary single-hand-use handle (600). As will be described in more detail below, handle (600) is operable to combine a guide catheter (630), a balloon dilation catheter (640), and endoscope (460) in such a manner as to allow a user to maneuver and operate each element using only a single hand. Balloon dilation catheter (640) comprises an elongate shaft (642) and a balloon (644) on distal end of elongate shaft (642). Handle (600) of the present example comprises a body (602) and an actuator (604). As best seen in FIG. 22, body (602) includes a through-bore (606) formed in an upper portion of body (602). Through-bore (606) extends the length of body (602). As will be described in greater detail below, through-bore (606) is operable to receive and selectively retain shaft (464) of endoscope (460). Body (602) further includes a channel (608) formed in a lower portion of body (602). Channel (608) extends partially the length of body (602). As best seen in FIG. 21, channel (608) comprises a generally truncated-cone cross-section. An elongate opening (610) formed in a bottom surface of body (602) extends substantially the length of channel (608) and provides external access to channel (608). As will be described in more detail below, actuator (604) is slidably coupled within channel (608) of body (602) via elongate opening (610) such that actuator (604) may translate within channel (608) between a proximal longitudinal position and a distal longitudinal position along a length of body (602). As will also be described in more detail below, actuator (604) is coupled with balloon dilation catheter (640) such that translation of actuator (604) within channel (608) causes concurrent translation of balloon dilation catheter (640) relative to body (602).

Actuator (604) comprises a hollow oval-shaped body (612). Actuator (604) further comprises a protrusion (614) that extends inwardly from an interior surface of body (612). As best seen in FIG. 21, protrusion (614) comprises a generally truncated-cone cross-section similar to the cross-section of channel (608). Body (602) is positioned within the hollow interior of body (612) of actuator (604) and protrusion (614) of actuator (604) is positioned within channel (608) so as to slidably couple actuator (604) with body (602). With protrusion (614) positioned within channel (608), actuator (604) is operable to translate along the length of channel (608) between a proximal longitudinal position and a distal longitudinal position. Protrusion (614) comprises a through-bore (618) that is configured to receive and selectively couple balloon dilation catheter (640) with actuator (604). In this way, translation of actuator (604) within channel (608) is communicated to balloon dilation catheter (640). As best seen in FIGS. 20 and 22, an exterior surface of body (612) of actuator (604) is saddle-shaped. This saddle-shaped exterior surface allows a user to easily locate and maneuver actuator (604) with only a single finger or thumb while holding handle (600).

Figure 23A:
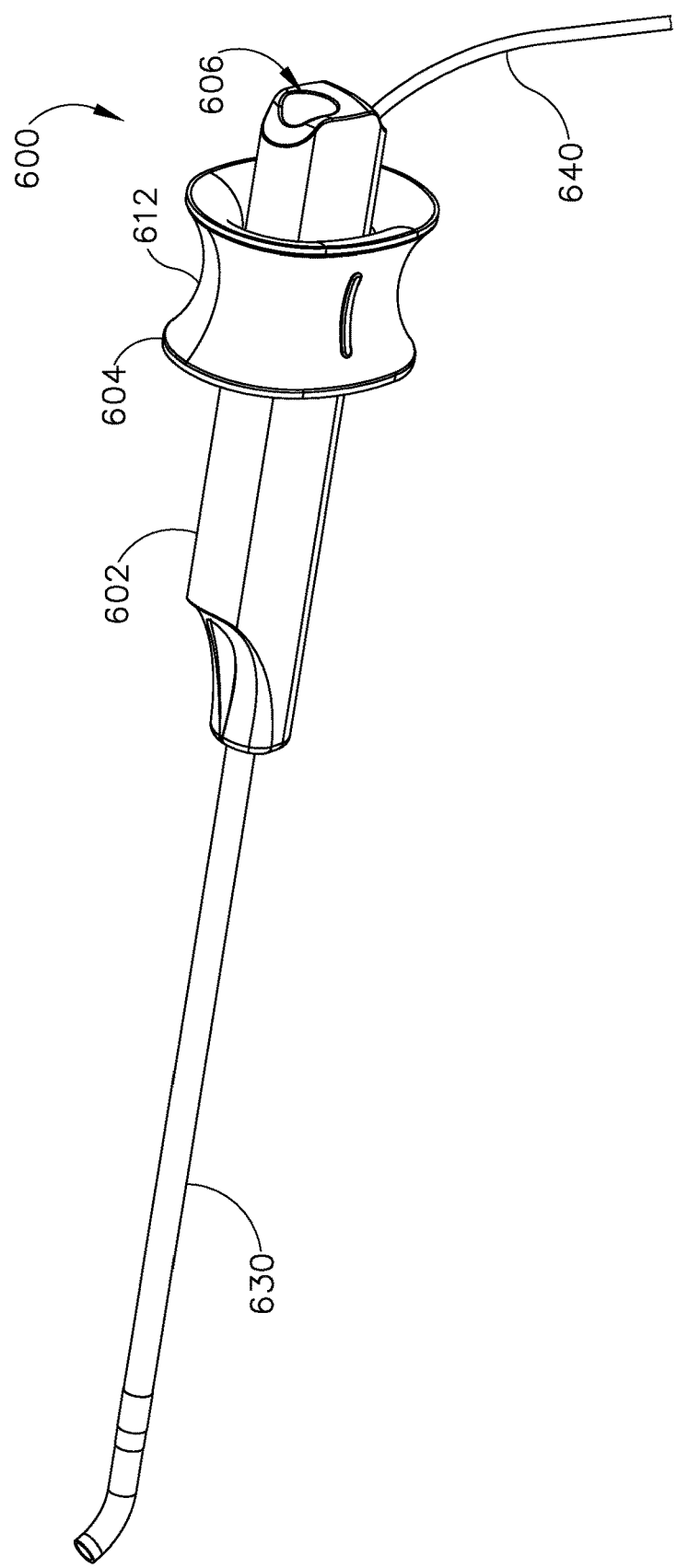
FIG. 23A depicts a perspective view of the handle of FIG. 19 with the guide catheter of FIG. 7A and an exemplary balloon dilation catheter positioned therein.

As best seen in FIG. 22, body (602) comprises a curved proximal bore (616) extending between a proximal end of body (602) and a proximal end of channel (608). As will be described in more detail below, the curved shape of proximal bore (616) is operable to limit interference between endoscope (460) and balloon dilation catheter (640). Body (602) further comprises a distal bore (620) extending between a distal end of body (602) and a distal end of channel (608). A distal portion (622) of distal bore (620) is sized to receive and selectively retain guide catheter (630) such that guide catheter (630) may be coupled with a distal end of body (602) and extend distally therefrom as shown in FIG. 23A. Guide catheter (630) of the present example is configured to operate substantially similar to guide catheters (100, 300, 430, 500) described above. In particular, guide catheter (630) is operable to direct balloon dilation catheter (640) toward the Eustachian tube (26) (or any other anatomical passageway (e.g., within the ear, nose, or throat, etc.)) such that balloon dilation catheter (640) may safely and effectively access the Eustachian tube (26).

As best seen in FIG. 22, proximal bore (616), channel (608), through-bore (618) of actuator (604), and distal bore (620) form a continuous passageway through body (602), which leads directly to guide catheter (630) when coupled with body (602). Balloon dilation catheter (640) is configured to pass through this passageway within body (602) and to further pass though guide catheter (630) when coupled with body (602). As described above, balloon dilation catheter (640) is selectively coupled with actuator (604) such that translation of actuator (604) within channel (608) is communicated to balloon dilation catheter (640). Thus, it should be understood that translation of actuator (604) within channel (608) causes concurrent translation of balloon dilation catheter (640) within this passageway. In particular, balloon dilation catheter (640) is configured to translate within proximal bore (616), channel (608), through-bore (618) of actuator (604), distal bore (620), and guide catheter (630) in response to translation of actuator (604). Balloon dilation catheter (640) of the present example is configured to operate substantially similar to balloon dilation catheters (200, 420, 520) described above. In particular, balloon dilation catheter (640) is operable to safely and effectively access and dilate the Eustachian tube (26) (or any other anatomical passageway (e.g., within the ear, nose, or throat, etc.)).

Figure 23B:
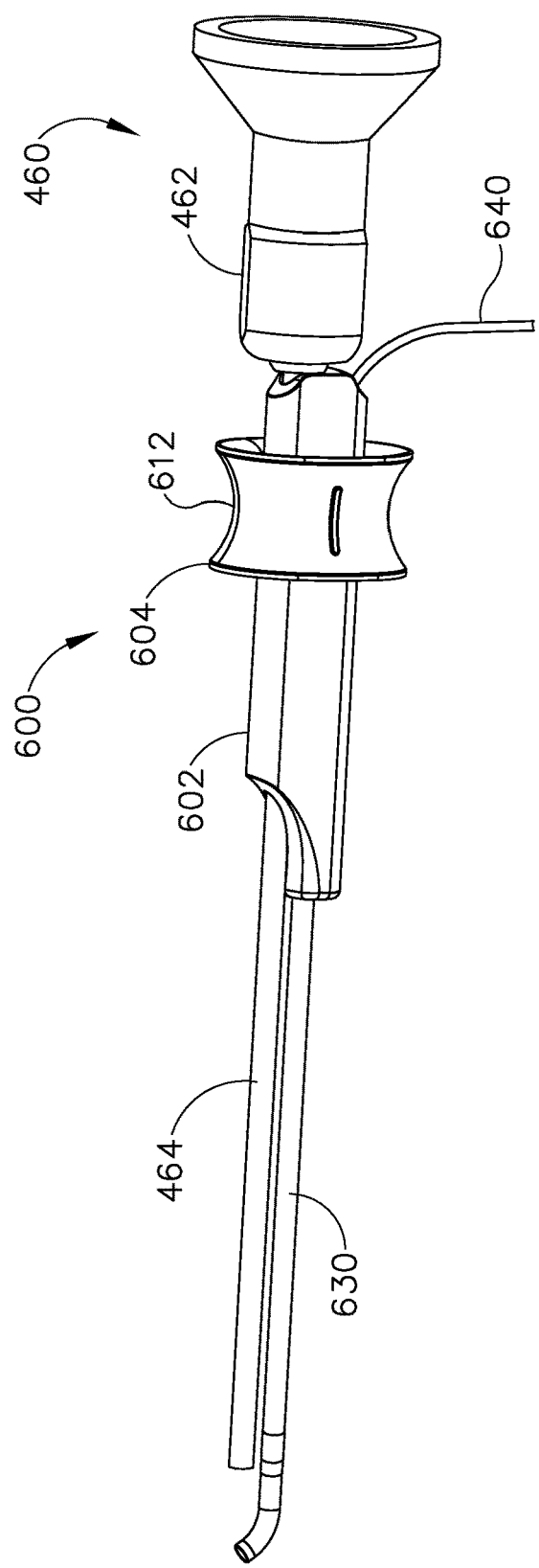
FIG. 23B depicts a perspective view of the handle of FIG. 19 with the endoscope of FIG. 15 positioned therein.
Figure 23C:
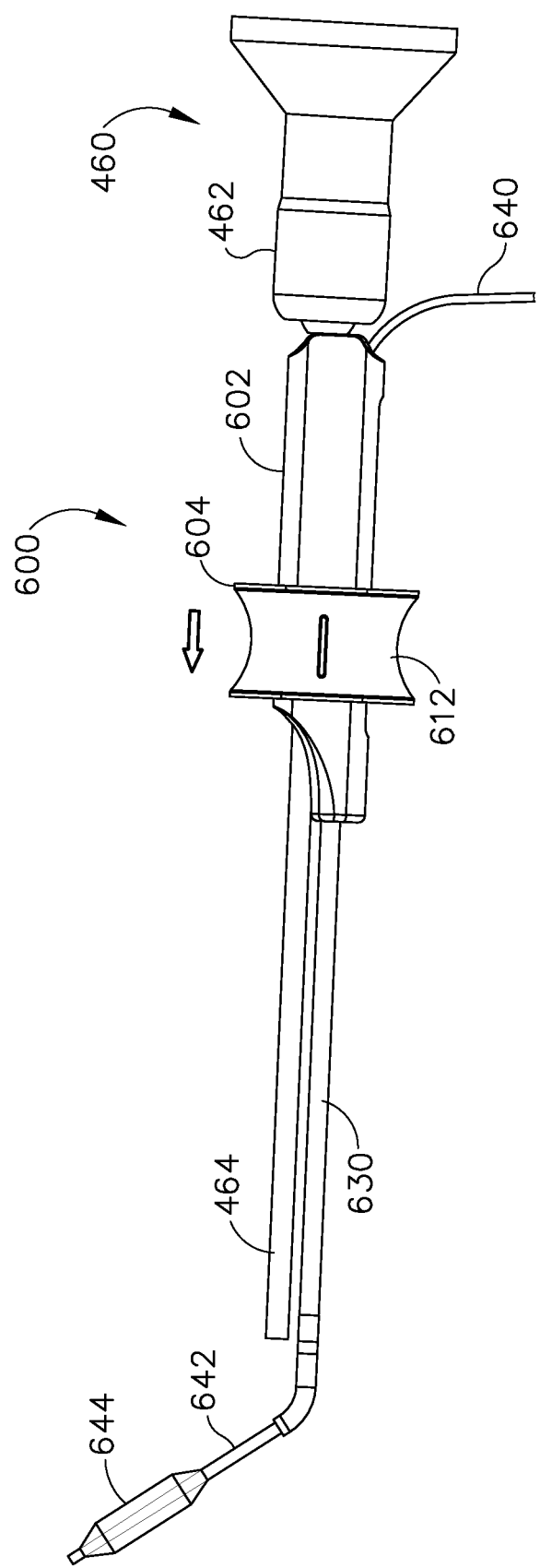
FIG. 23C depicts a perspective view of the handle of FIG. 19 with the balloon dilation catheter of FIG. 23A translated distally by distal translation of an actuator of the handle.
Figure 24:
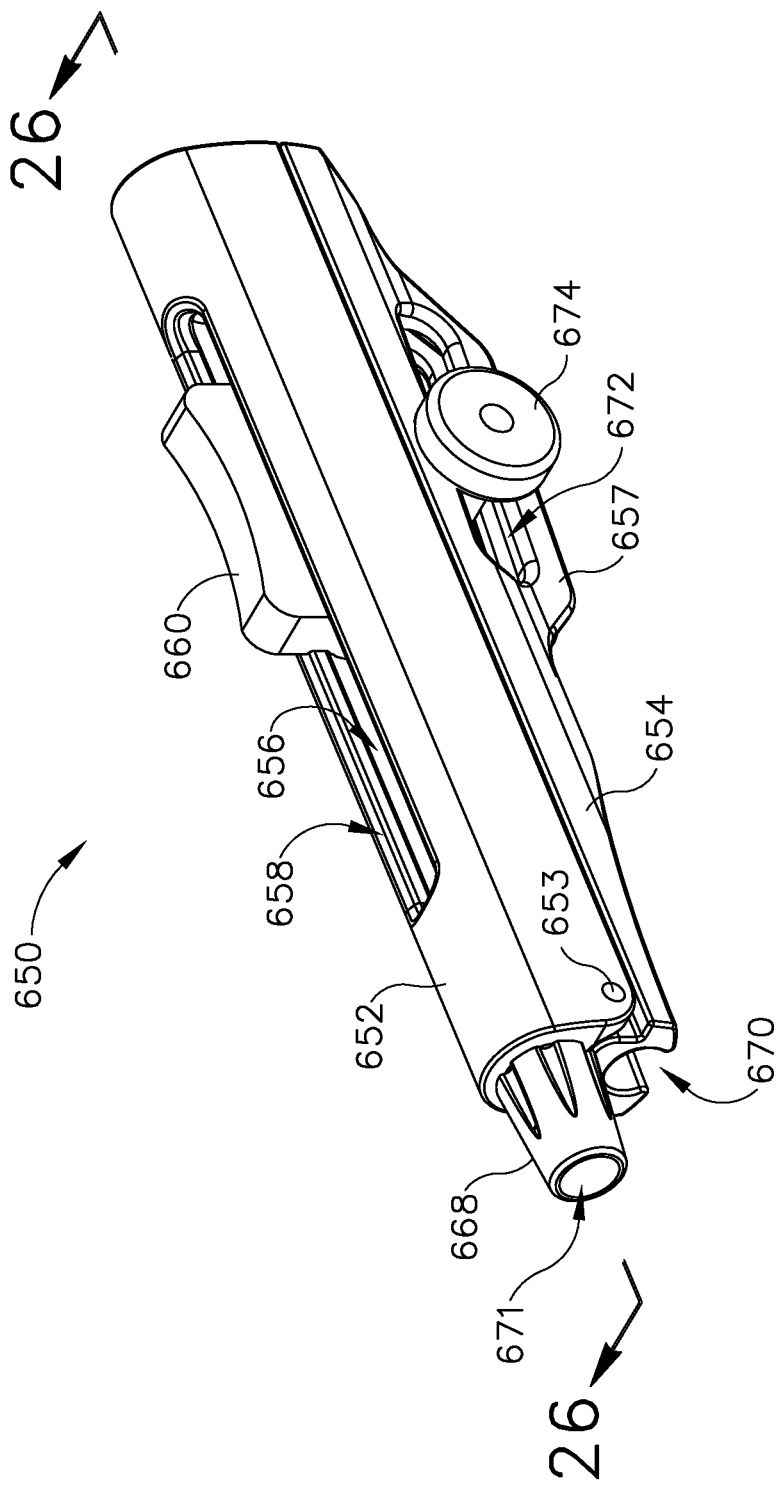
FIG. 24 depicts a perspective view of another exemplary handle suitable for use with the dilation catheter system of FIG. 12.

As shown in FIG. 23B, endoscope (460) may be positioned within through-bore (606) and oriented so as to view the distal end of guide catheter (630). As best seen in FIGS. 23B and 23C, the curved shape of proximal bore (616) is operable to direct balloon dilation catheter (640) away from endoscope (460) such that endoscope (460) does not interfere with translation of balloon dilation catheter (640). As will be described in more detail below, body (602) and/or through-bore (606) may comprise a locking feature configured to selectively secure endoscope (460) within through-bore (606). At this point, guide catheter (630) and endoscope (460) may be positioned within the patient adjacent the Eustachian tube (26). The user may then translate balloon dilation catheter (640) distally into the Eustachian tube (26) so as to position balloon (644) of balloon dilation catheter (640) within the Eustachian tube (26) distally of a distal end of guide catheter (630) by distally translating actuator (604) as shown in FIG. 23C.

It should be appreciated from the discussion above that handle (600) may be grasped and maneuvered, and actuator (604) may be translated, all using a single hand. For instance, while grasping handle (600), the user may use his or her index finger or thumb to translate actuator (604).

VI. Exemplary Single-Hand-Use, Pivoting Handle with Locking Roller

Figure 25:
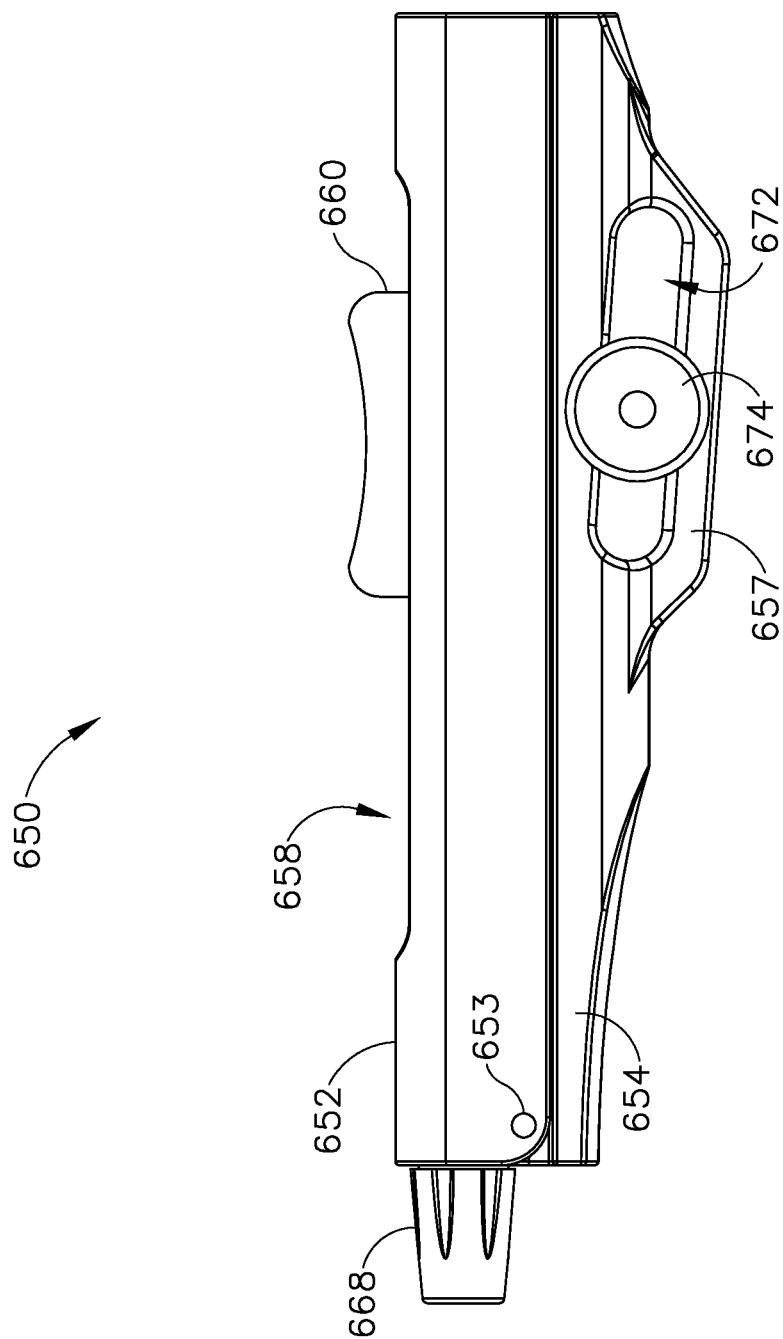
FIG. 25 depicts a side elevational view of the handle of FIG. 24.
Figure 26:
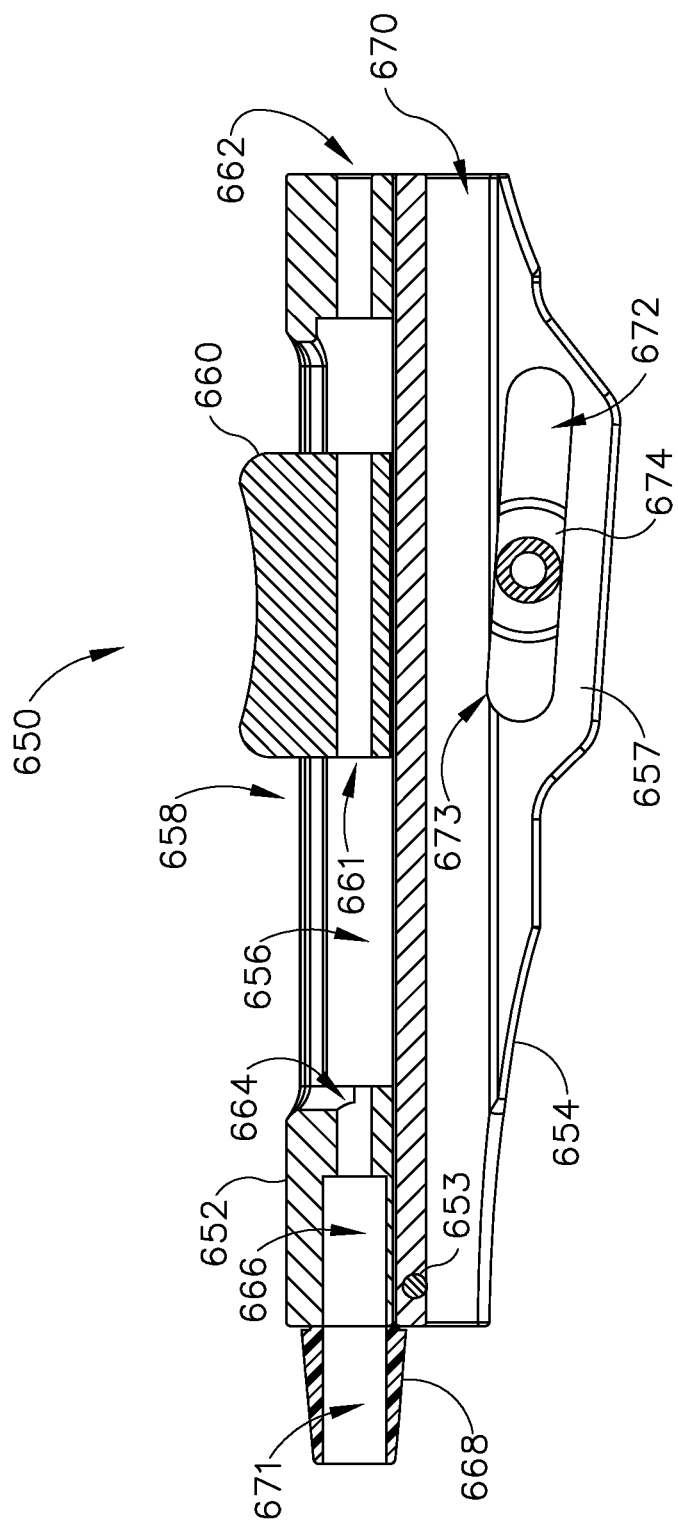
FIG. 26 depicts a cross-sectional side view of the handle of FIG. 24 taken along line 26-26 of FIG. 24.

Another exemplary single-hand use handle (650) is shown in FIGS. 24-28B. Handle (650) of the present example comprises a first body member (652), a second body member (654), and an actuator (660). A distal end of first body member (652) is pivotably coupled with a distal end of second body member (654) via a pin (653) such that first body member (652) and second body member (654) are pivotable toward and away from one another about pin (653). As best seen in FIG. 26, first body member (652) comprises a channel (656) formed therein. Channel (656) extends partially the length of first body member (652). An elongate opening (658) formed in a top surface of first body member (652) extends substantially the length of channel (656) and provides external access to channel (656). As will be described in more detail below, actuator (660) is slidably coupled within channel (656) of first body member (652) via elongate opening (658) such that actuator (660) may translate within channel (656) between a proximal longitudinal position and a distal longitudinal position along a length of first body member (652). Also as will be described in more detail below, actuator (660) is coupled with balloon dilation catheter (640) such that translation of actuator (660) within channel (656) causes concurrent translation of balloon dilation catheter (640) relative to first body member (652).

As best seen in FIG. 26, actuator (660) comprises a through-bore (661) that is configured to receive and selectively couple balloon dilation catheter (640) with actuator (660). In this way, translation of actuator (660) within channel (656) is communicated to balloon dilation catheter (640). A portion of actuator (660) extends from first body member (652) through elongate opening (658) and is exposed relative to first body member (652). As best seen in FIGS. 25 and 26, this exposed portion of actuator (660) is saddle-shaped. This saddle-shaped exposed portion allows a user to easily locate and maneuver actuator (660) with only a single finger or thumb while holding handle (650).

Figure 27A:
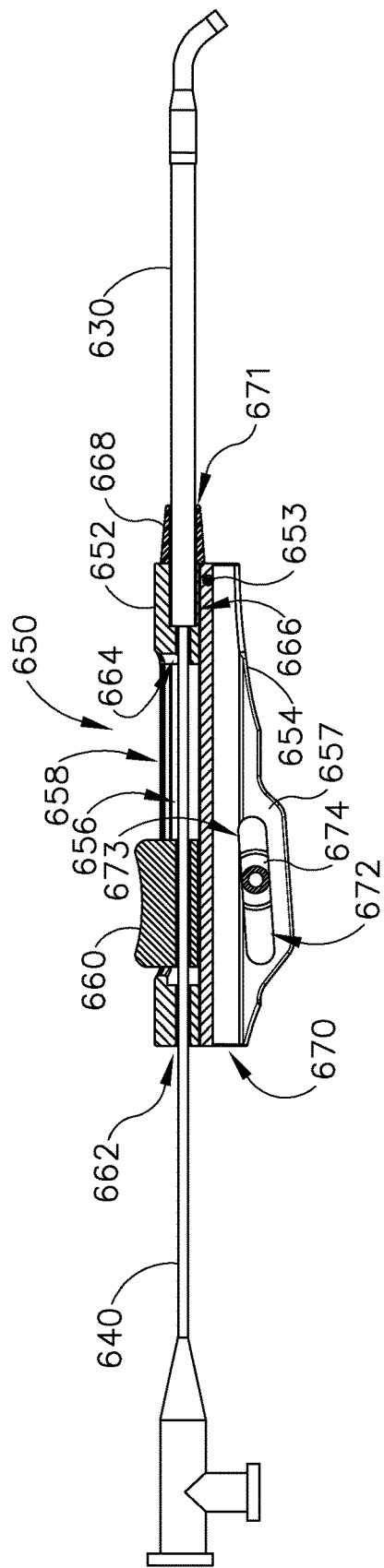
FIG. 27A depicts a cross-sectional side view of the handle of FIG. 24 with the guide catheter of FIG. 7A and an exemplary balloon dilation catheter positioned therein.

As also best seen in FIG. 22, first body member (652) comprises a proximal bore (662) extending between a proximal end of first body member (652) and a proximal end of channel (656). First body member (652) further comprises a distal bore (664) extending between a distal end of first body member (652) and a distal end of channel (656). A distal portion (666) of distal bore (664) is sized to rotatably receive a proximal end of guide catheter (630) such that guide catheter (630) is operable to rotate within distal portion (666) of distal bore (664). A rotation knob (668) is rotatably coupled to a distal end of first body member (652). Rotation knob (668) is configured to rotate relative to first body member (652). Rotation knob (668) comprises a through-bore (671) that is coaxially aligned with distal portion (666) of distal bore (664) and is sized to receive and selectively retain guide catheter (630) such that guide catheter (630) may be coupled with the distal end of first body member (652) and extend distally therefrom as shown in FIG. 27A; and further such that rotation of rotation knob (668) is communicated to guide catheter (630).

Proximal bore (662), channel (656), through-bore (661) of actuator (660), distal bore (664), and through-bore (671) of rotation knob (668) form a continuous passageway through first body member (652) that leads directly to guide catheter (630) when coupled with rotation knob (668). Balloon dilation catheter (640) is configured to pass through this passageway within first body member (652) and to further pass though guide catheter (630) when coupled with rotation knob (668). As described above, balloon dilation catheter (640) is selectively coupled with actuator (660) such that translation of actuator (660) within channel (656) is communicated to balloon dilation catheter (640). Thus, it should be understood that translation of actuator (660) within channel (656) causes concurrent translation of balloon dilation catheter (640) within this passageway. In particular, balloon dilation catheter (640) is configured to translate within proximal bore (662), channel (656), through-bore (661) of actuator (660), distal bore (664), through-bore (671) of rotation knob (668), and guide catheter (630) in response to translation of actuator (660) within channel (656).

Figure 27B:
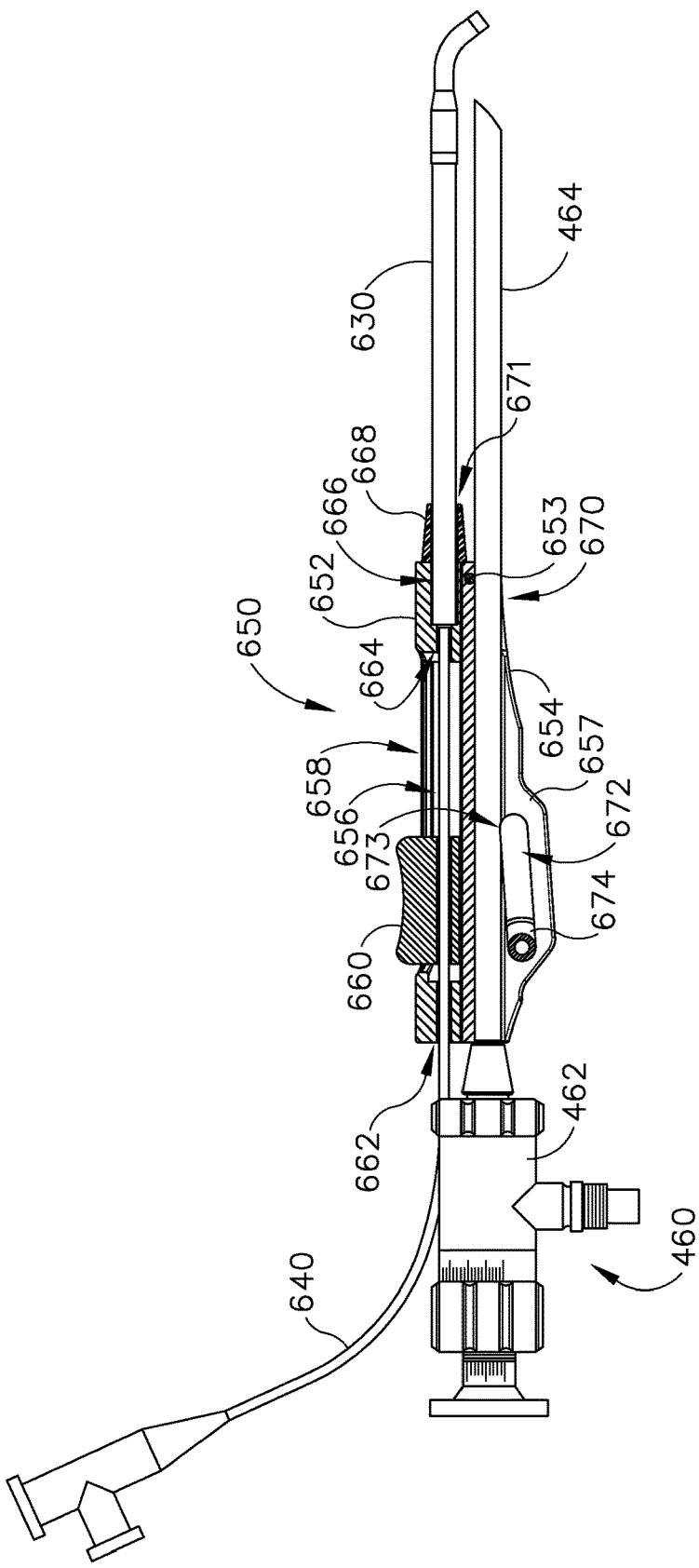
FIG. 27B depicts a cross-sectional side view of the handle of FIG. 24 with the endoscope of FIG. 15 positioned therein.
Figure 27C:
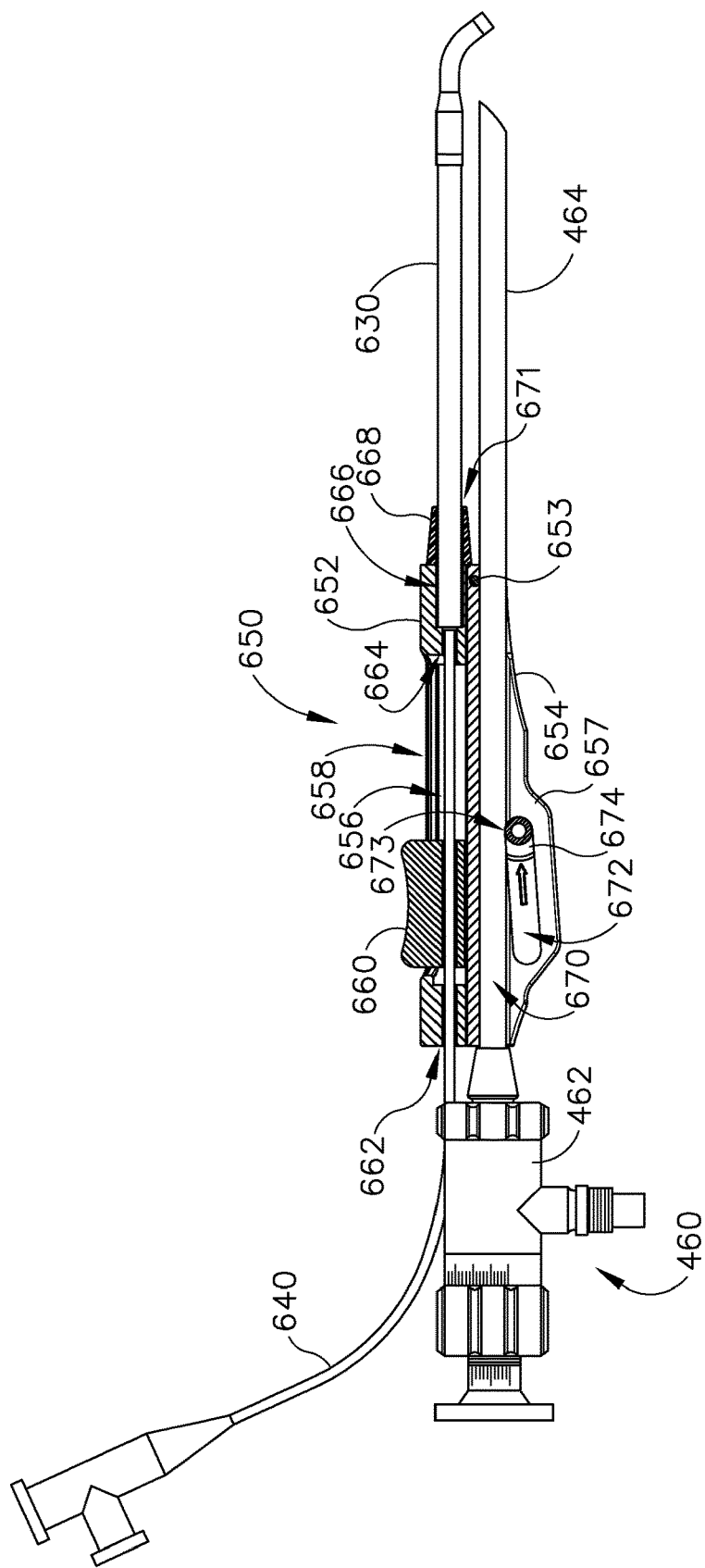
FIG. 27C depicts a cross-sectional side view of the handle of FIG. 19 with the endoscope of FIG. 15 locked within the handle by distal translation of a locking member.

Second body member (654) includes a through-bore (670) formed therein. Through-bore (670) extends the complete length of second body member (654). As shown in FIG. 27B, through-bore (670) is operable to receive and selectively retain endoscope (460). Second body member (654) further includes a pair of flanges (657) extending downwardly from opposing sides of second body member (654). An elongate slot (672) is formed in each flange (657). Slots (672) are angled distally-upwardly and overlap with through-bore (670) at a distal end of slots (672). This overlap of slots (672) and through-bore (670) provides an opening (673) in a bottom surface of second body member (654). Opening (673) provides external access to through-bore (670). A dumbbell-shaped roller (674) is slidably and rotatably disposed within slots (672) such that roller (674) is slidable/rotatable between a proximal (unlocked) position (FIG. 27B) and a distal (locked) position (FIG. 27C). As shown in FIG. 27C, with endoscope (460) positioned within through-bore (670), with roller (674) moved into the distal (locked) position, roller (674) is configured to bear against an exterior surface of endoscope (460) via opening (673) so as to lock endoscope (460) within through-bore (670). Roller (674) thus prevents endoscope (460) from rotating or translating relative to second body member (654). It should be appreciated that roller (674) may be moved from the distal (locked) position into the proximal (unlocked) position in order to unlock endoscope (460) to thereby enable reorientation or maneuvering of endoscope (460).

Figure 27D:
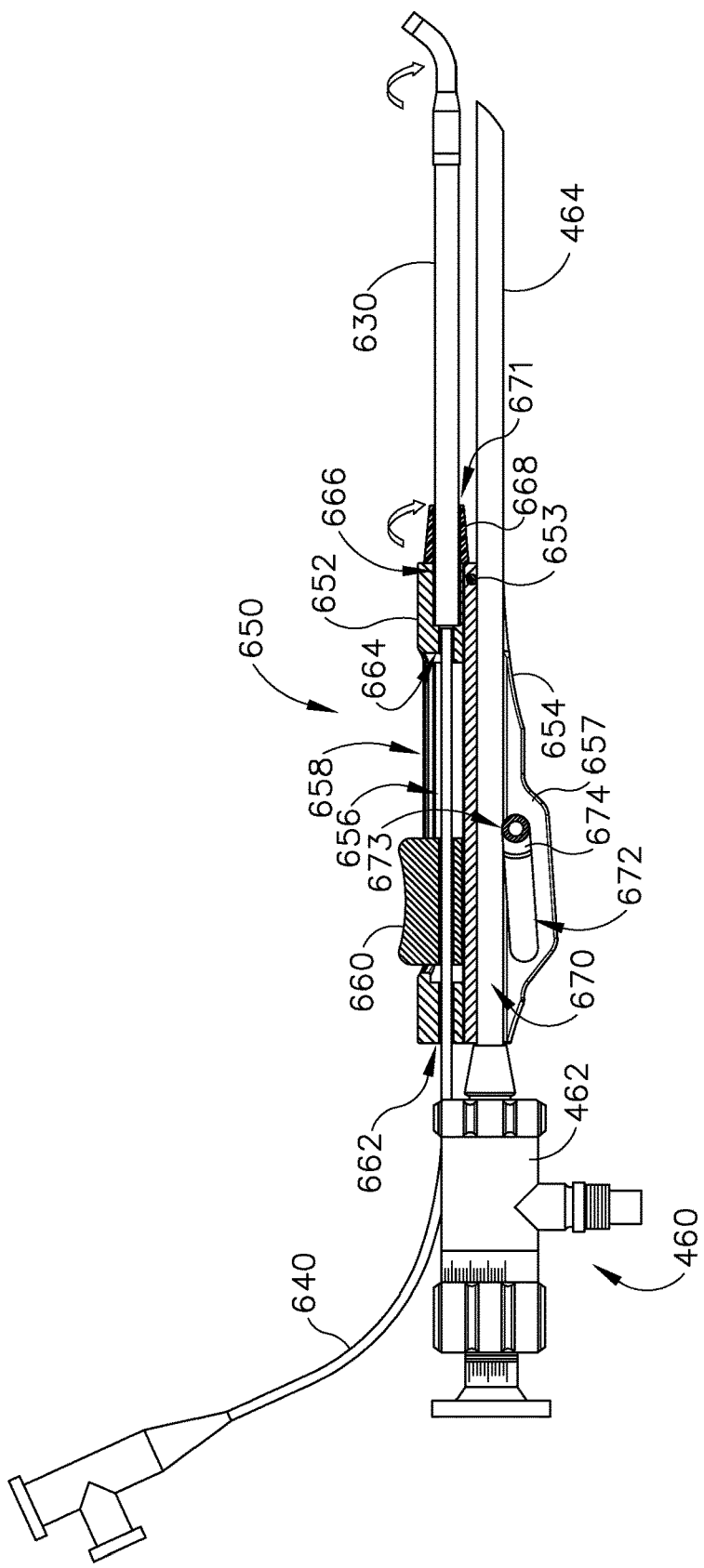
FIG. 27D depicts a cross-sectional side view of the handle of FIG. 19 with the guide catheter of FIG. 7A rotated relative to the handle by rotation of a rotation knob.
Figure 27E:
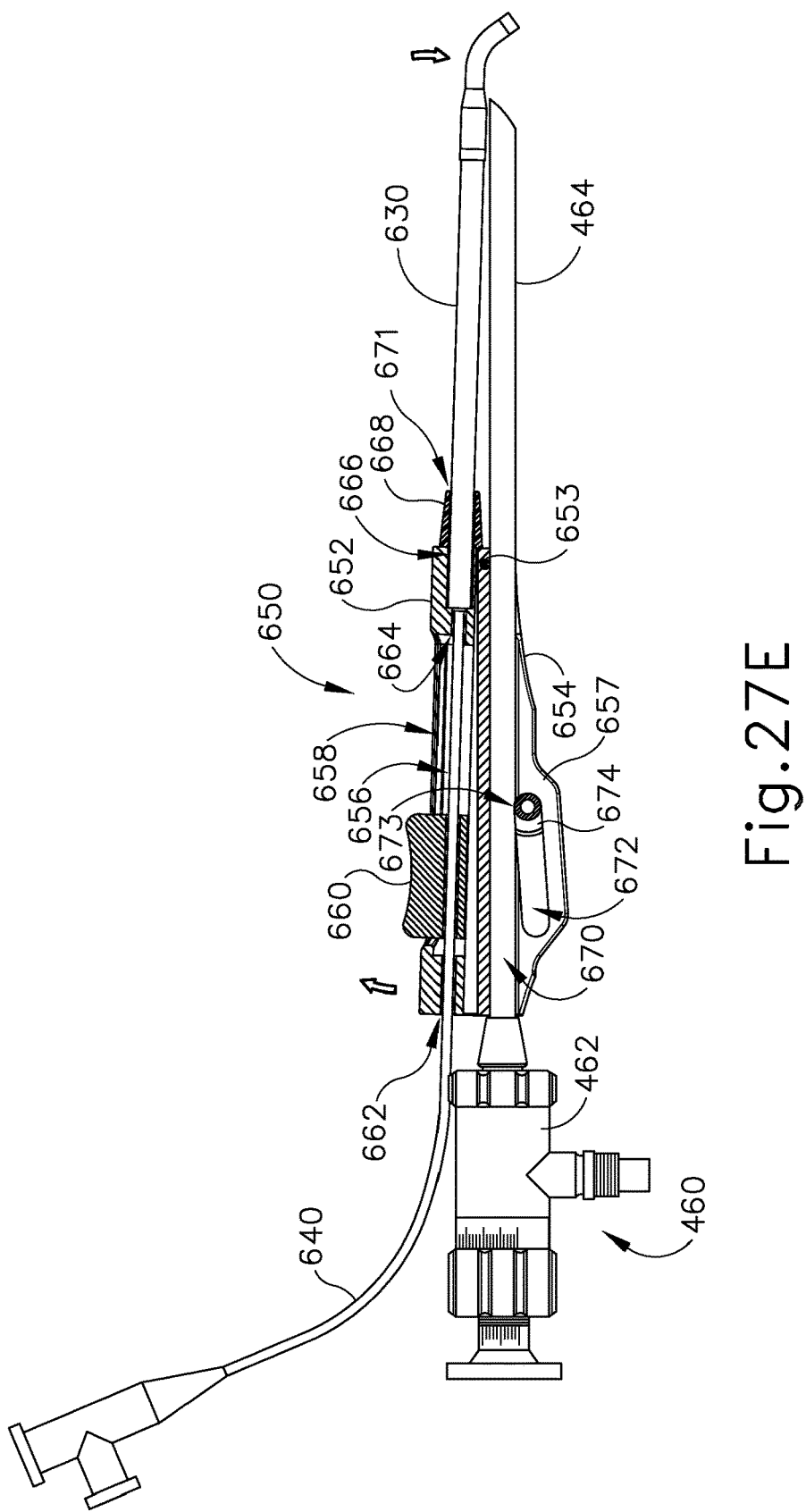
FIG. 27E depicts a cross-sectional side view of the handle of FIG. 19 with the guide catheter of FIG. 7A pivoted toward the endoscope of FIG. 15.
Figure 27F:
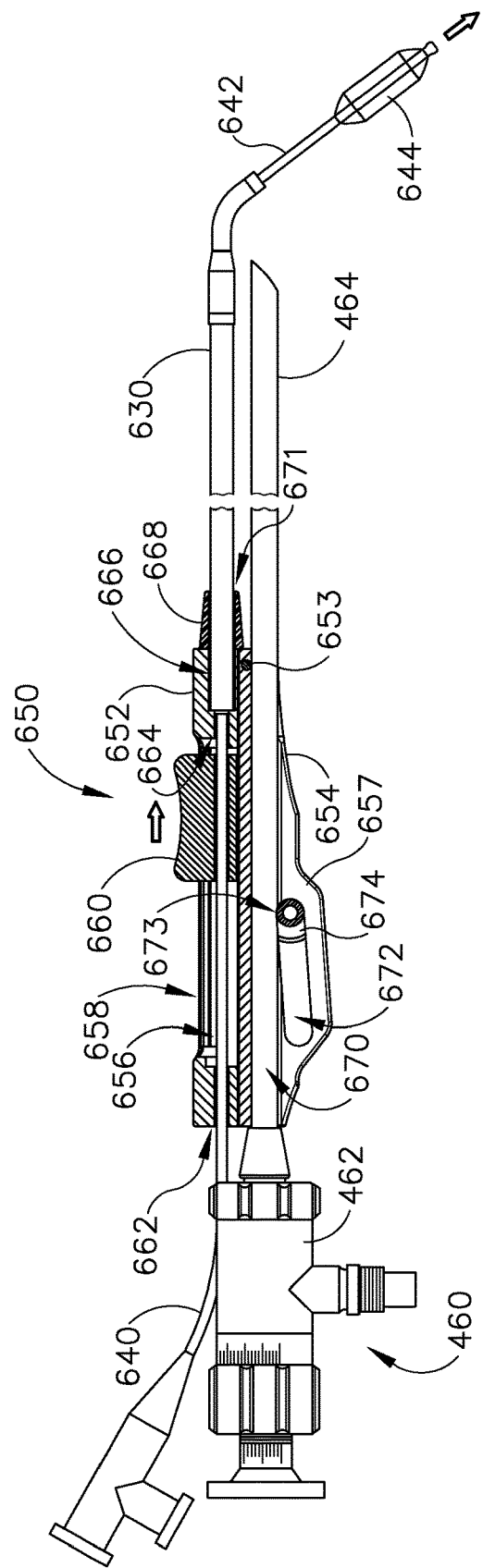
FIG. 27F depicts a cross-sectional side view of the handle of FIG. 19 with the balloon dilation catheter of FIG. 27A translated distally by distal translation of an actuator of the handle.
Figure 29:
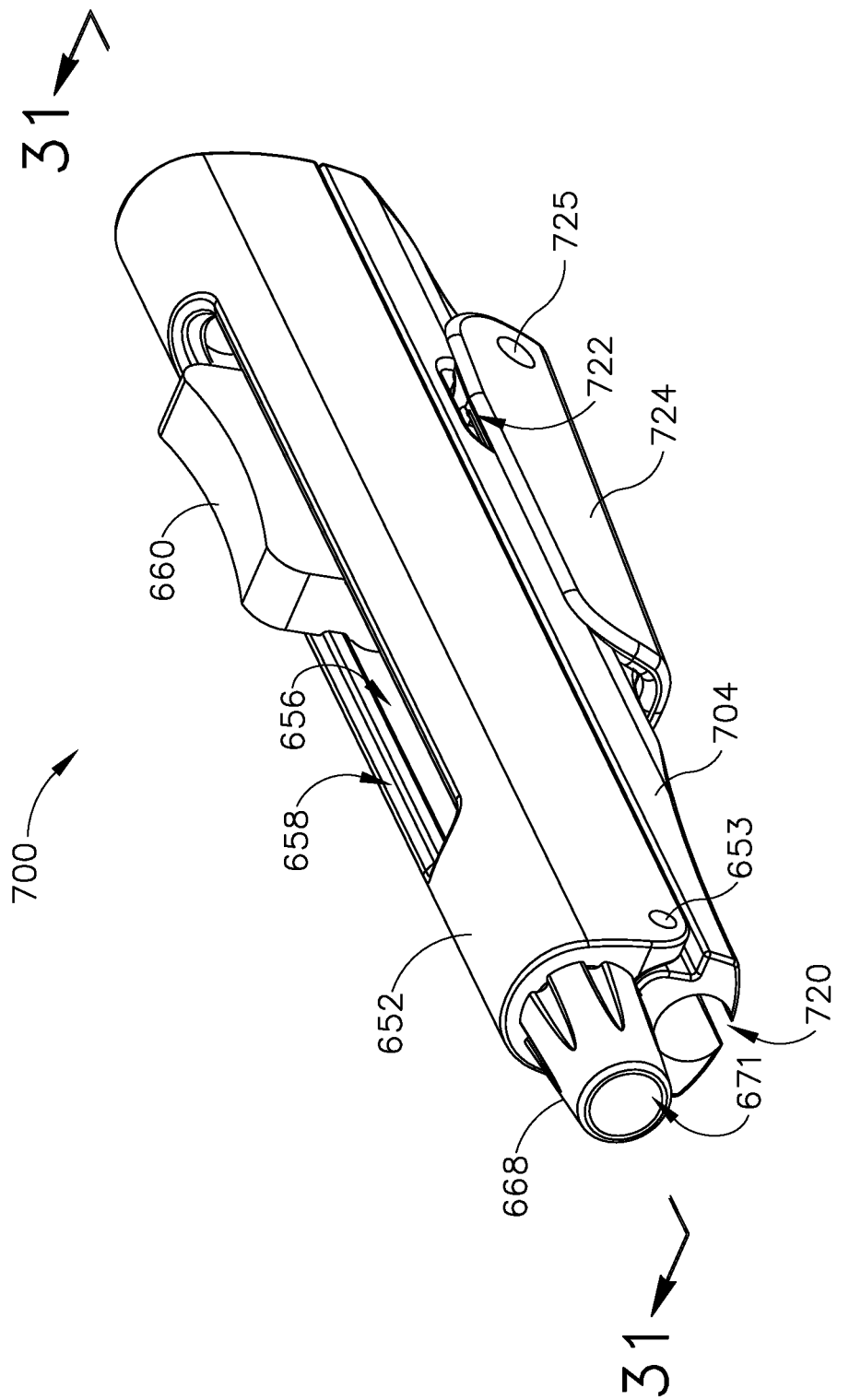
FIG. 29 depicts a perspective view of yet another exemplary handle suitable for use with the dilation catheter system of FIG. 12.
Figure 30:
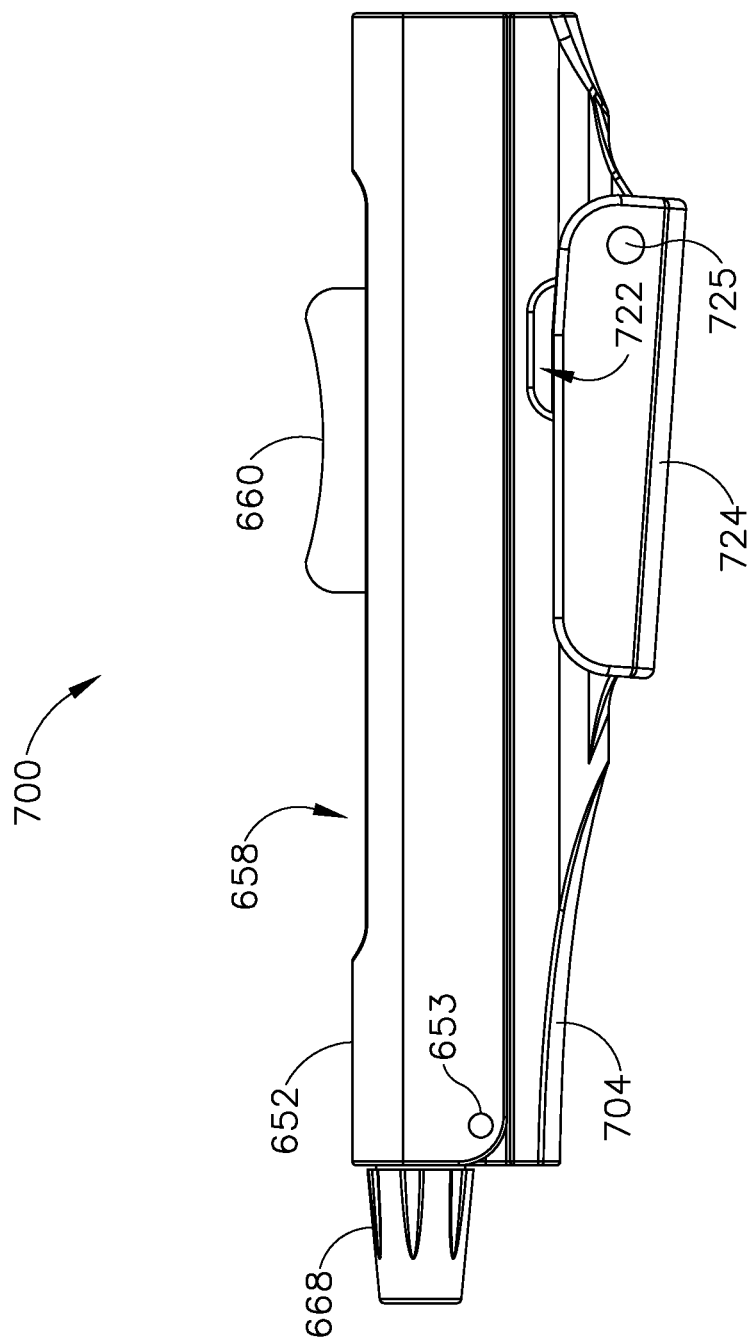
FIG. 30 depicts a side elevational view of the handle of FIG. 29.

As mentioned above, to adjust the orientation of guide catheter (630), the user may rotate rotation knob (668) to thereby rotate guide catheter (630) relative to first body member (652) as shown in FIG. 27D. In addition, with guide catheter (630) coupled to first body member (652) via rotation knob (668) and with endoscope (460) coupled within second body member (654), the user may pivot first body member (652) toward or away from second body member (654) about pin (653) to thereby manipulate the orientation of guide catheter (630) relative to endoscope (460) as shown in FIG. 27E. In some versions of handle (650), it may be desirable to limit the amount by which first body member (652) may be pivoted toward or away from second body member (654) about pin (653). For instance, as shown in FIG. 28A, first body member (652) may be provided with a triangle-shaped tab (676) and second body member (654) may be provided with a complimentary V-shaped recess (678). As shown in FIG. 28B, as first body member (652) is pivoted away from second body member (654) about pin (653), a distal surface of tab (676) engages a distal surface of recess (678) so as to prevent further pivoting of first body member (652). Once guide catheter (630) is positioned at a desired location, the user may then translate balloon dilation catheter (640) distally into the Eustachian tube (26) so as to position balloon (644) of balloon dilation catheter (640) within the Eustachian tube (26) distally of a distal end of guide catheter (630) by distally translating actuator (660) as shown in FIG. 27F.

It should be appreciated that handle (650) may be grasped, oriented, and maneuvered, and actuator (660) may be translated using a single hand. For instance, while grasping handle (630), the user may use his or her index finger or thumb to orient first body member (652) relative to second body member (654) and/or to translate actuator (660).

A. Exemplary Locking Lever

In some versions of handle (650), it may be desirable to provide second body member (654) with an alternative locking feature for selectively coupling endoscope (460) within through-bore (670) of second body member (654). FIGS. 29-31B show an exemplary handle (700) having first body member (652) and its components as described above with reference to handle (650). Handle (750) further includes an exemplary alternative second body member (704). As with handle (650) described above, the distal end of first body member (652) is pivotably coupled with a distal end of second body member (704) via pin (653) such that first body member (652) and second body member (704) are pivotable toward and away from one another about pin (653).

Figure 31A:
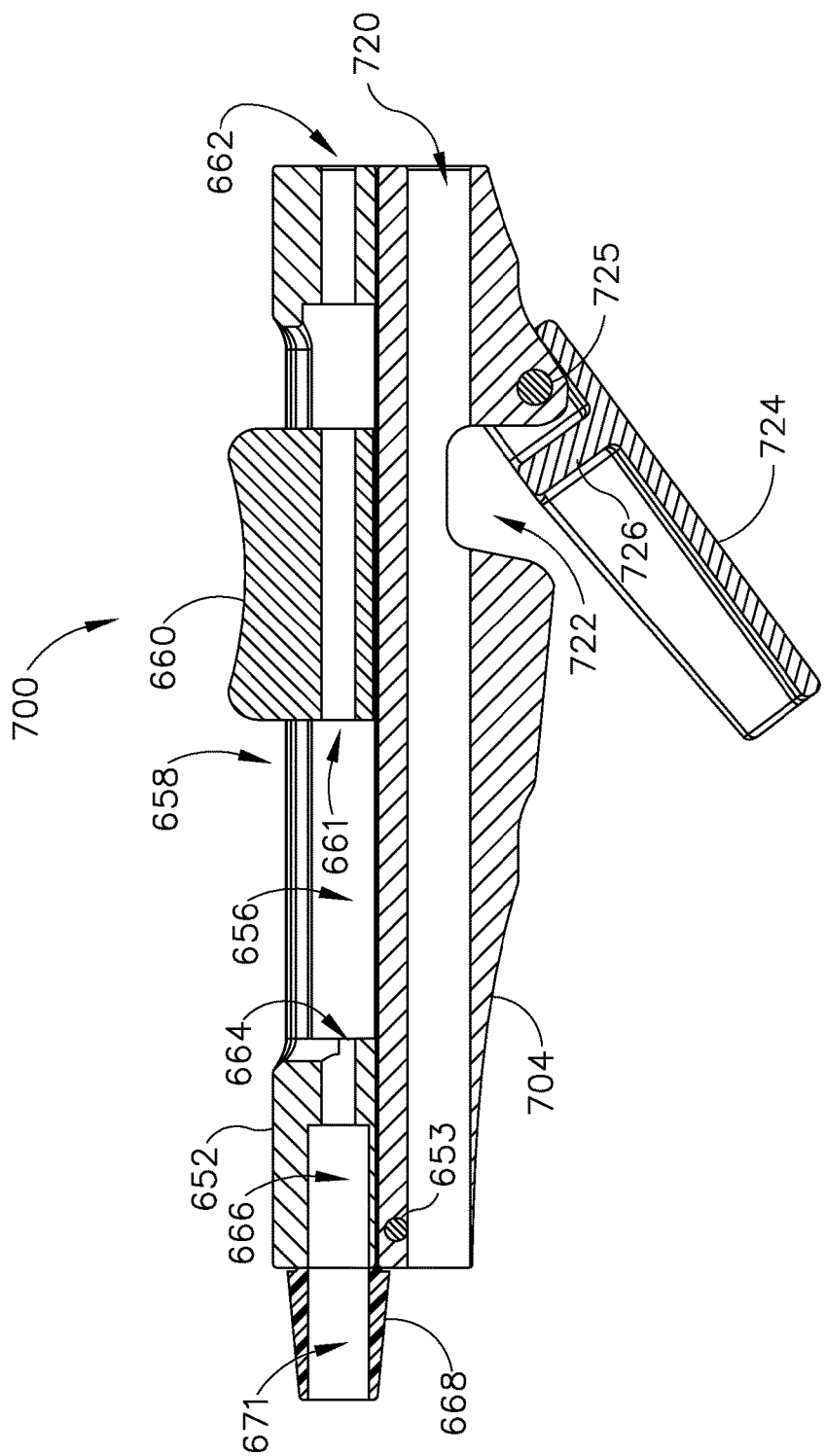
FIG. 31A depicts a side cross-sectional view of the handle of FIG. 29 taken along line 31-31 of FIG. 29, with a locking member of the handle in a first rotational position.
Figure 31B:
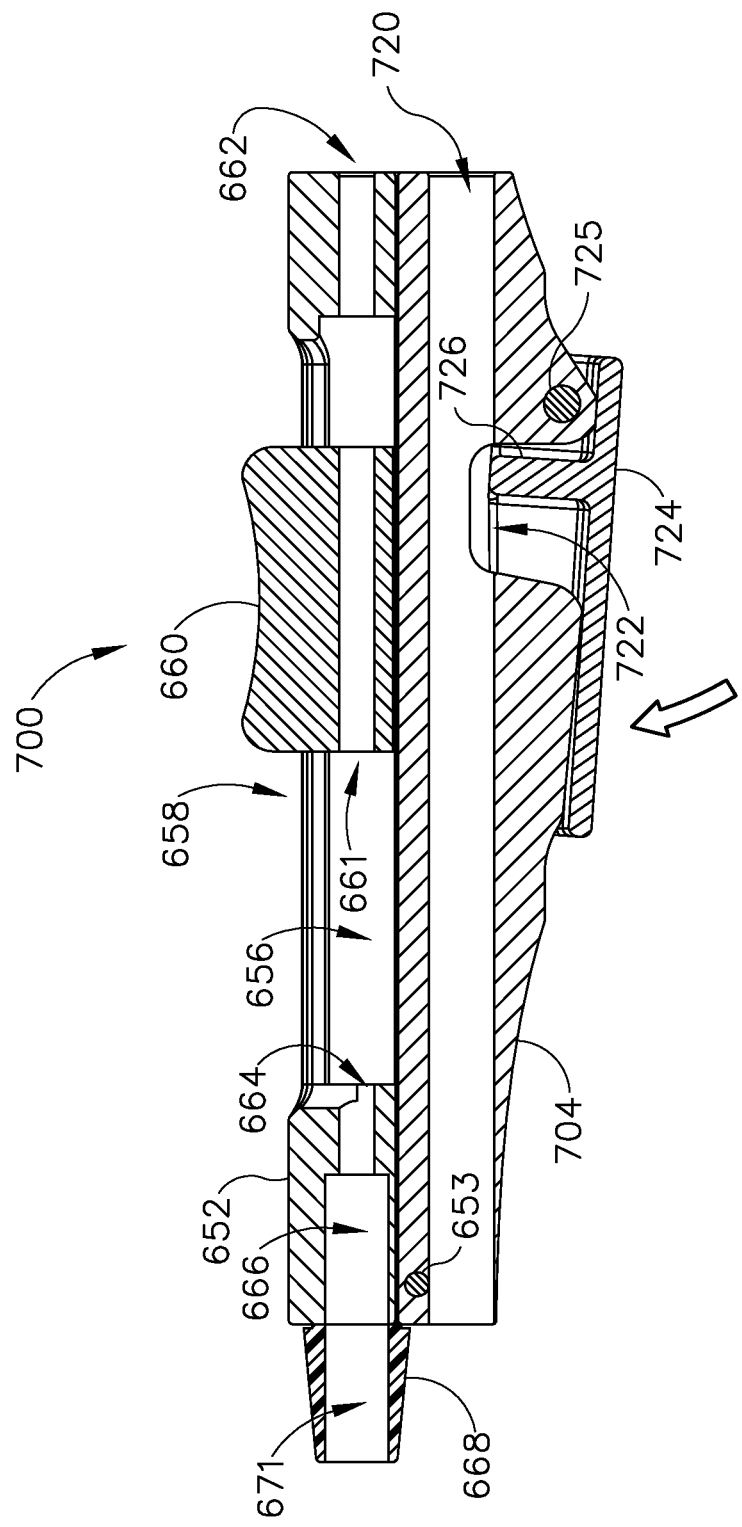
FIG. 31B depicts a side cross-sectional view of the handle of FIG. 29 taken along line 31-31 of FIG. 29, with the locking member of FIG. 31A rotated into a second rotational position.
Figure 32:
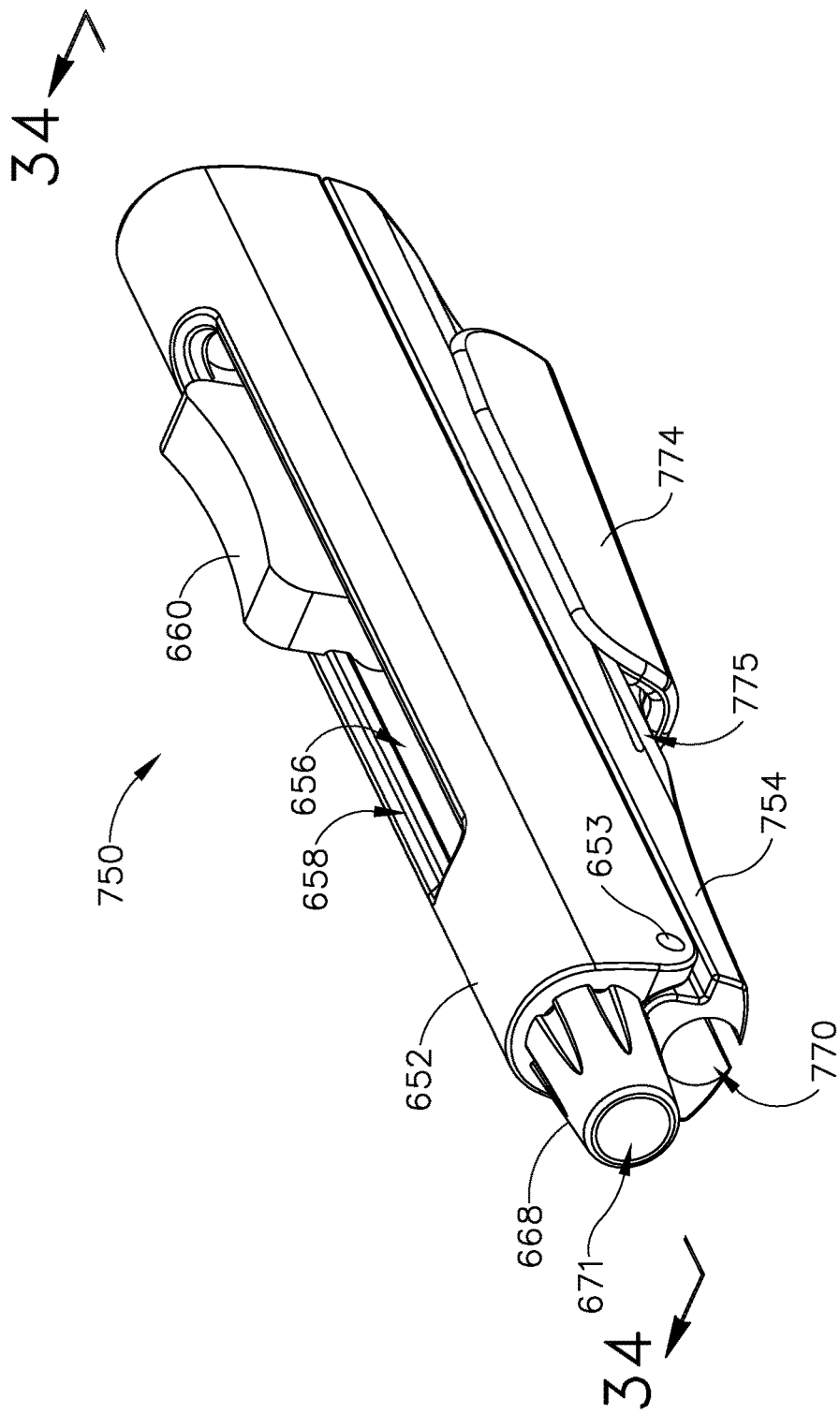
FIG. 32 depicts a perspective view of yet another exemplary handle suitable for use with the dilation catheter system of FIG. 12.
Figure 33:
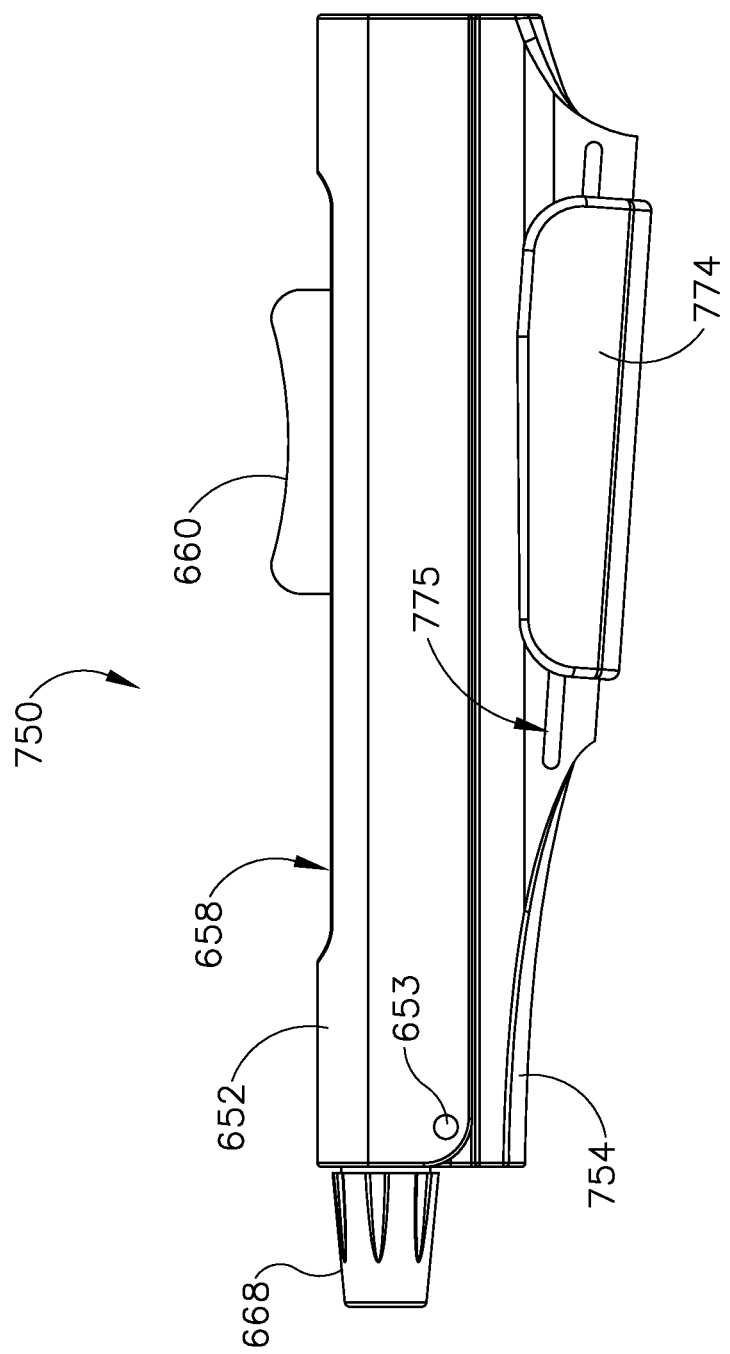
FIG. 33 depicts a side elevational view of the handle of FIG. 32.

As best seen in FIG. 31A, second body member (704) includes a through-bore (720) formed therein. Through-bore (720) extends the complete length of second body member (704). As with through bore (670) of handle (650) described above, through-bore (720) is operable to receive and selectively retain endoscope (460). Second body member (704) further includes an opening (722) formed in a bottom surface of second body member (704). Opening (722) provides external access to through-bore (720). A lever (724) is pivotably coupled with second body member (704) below through-bore (720) via a pin (725) such that lever (724) is pivotable toward and away from second body member (704) about pin (725) between an unlocked position (FIG. 31A) and a locked position (FIG. 31B). As shown in FIG. 31B, with lever (724) in the locked position, a lateral member (726) of lever (724) is configured to bear against an exterior surface of endoscope (460) via opening (722) so as to lock endoscope (460) within through-bore (720). It should be appreciated that lever (724) may be rotated from the locked position into the unlocked position in order to enable reorientation or maneuvering of endoscope (460). Various suitable features that may be provided to selectively hold lever (724) in the locked position will be apparent to those of ordinary skill in the art in view of the teachings herein.

It should be appreciated that handle (700) may be grasped, oriented, and maneuvered, and actuator (710) may be translated using a single hand. For instance, while grasping handle (700), the user may use his or her index finger or thumb to orient first body member (702) relative to second body member (704) and/or to translate actuator (710).

B. Exemplary Locking Sled

FIGS. 32-34B show another exemplary handle (750) having first body member (652) and its components as described above with reference to handle (650). Handle (750) further includes another exemplary alternative second body member (754). As with handle (650) described above, the distal end of first body member (652) is pivotably coupled with a distal end of second body member (754) via pin (653) such that first body member (652) and second body member (754) are pivotable toward and away from one another about pin (653).

Figure 34A:
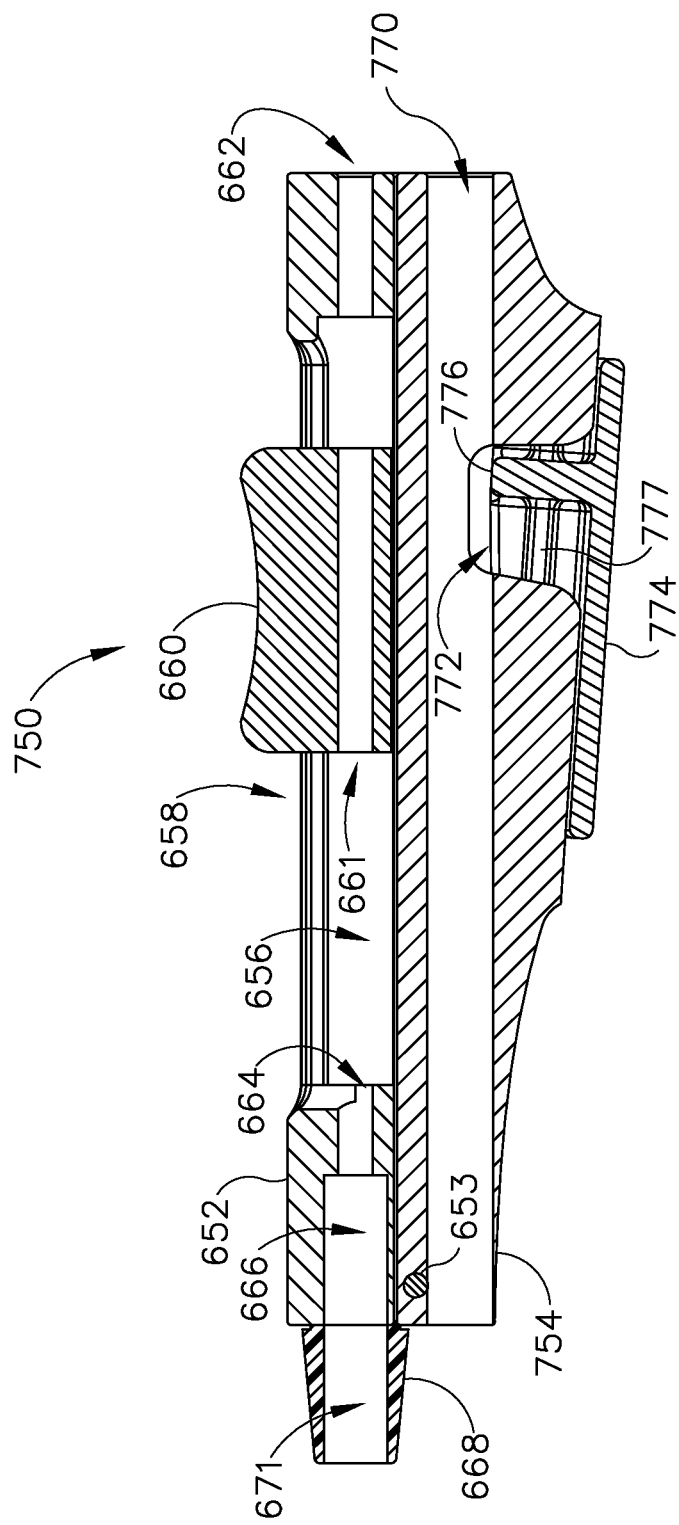
FIG. 34A depicts a cross-sectional side view of the handle of FIG. 32 taken along line 34-34 of FIG. 32 with a locking member of the handle in a first translational position.
Figure 34B:
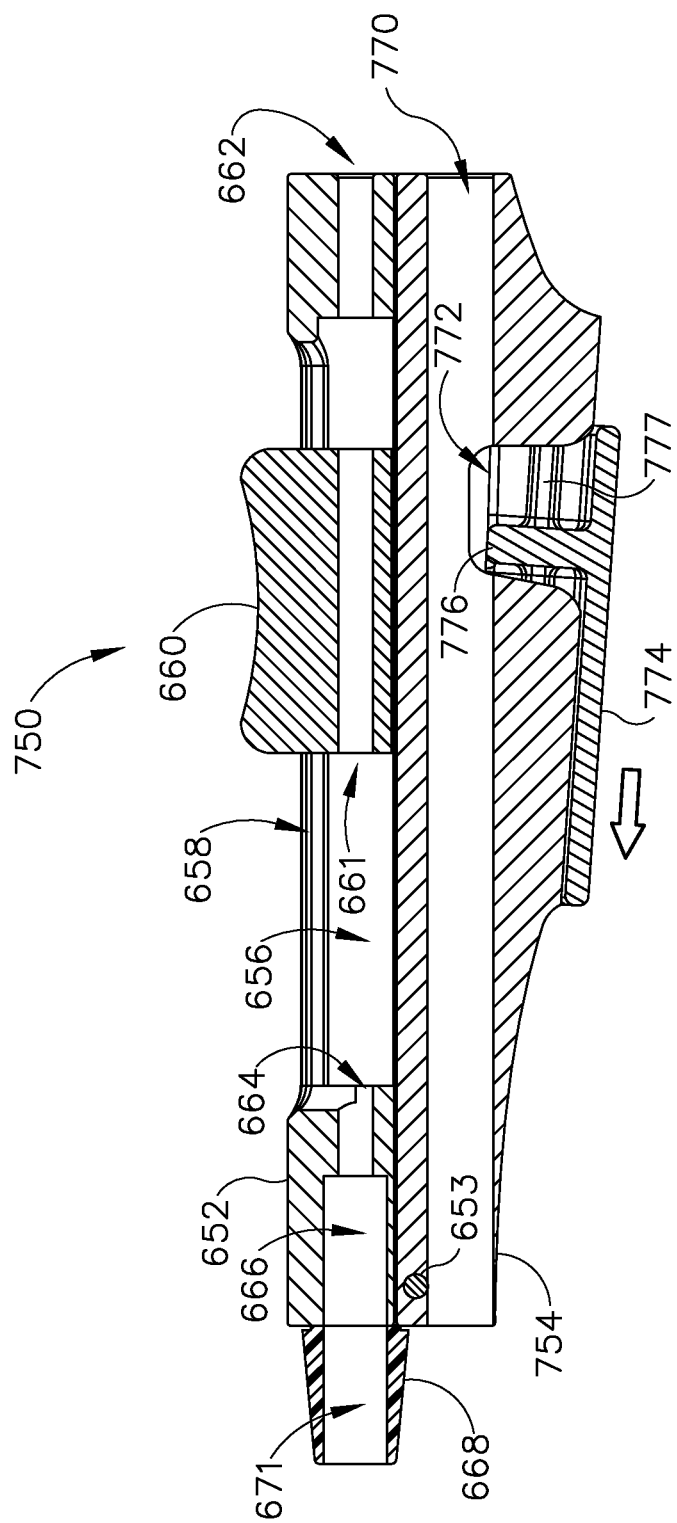
FIG. 34B depicts a side cross-sectional view of the handle of FIG. 32 taken along line 34-34 of FIG. 32 with the locking member of FIG. 34A translated into a second translational position.
Figure 35:
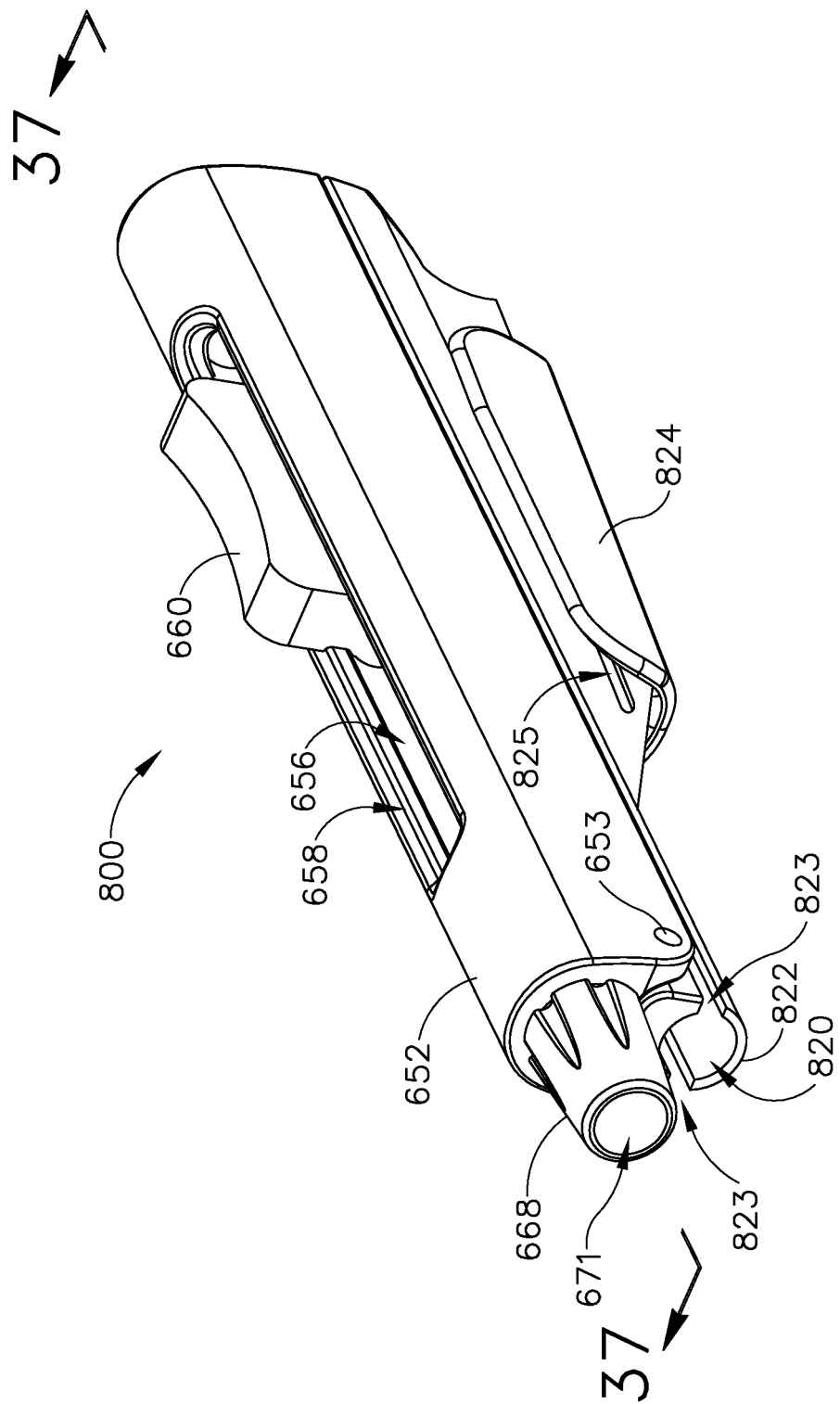
FIG. 35 depicts a perspective view of yet another exemplary handle suitable for use with the dilation catheter system of FIG. 12.
Figure 36:
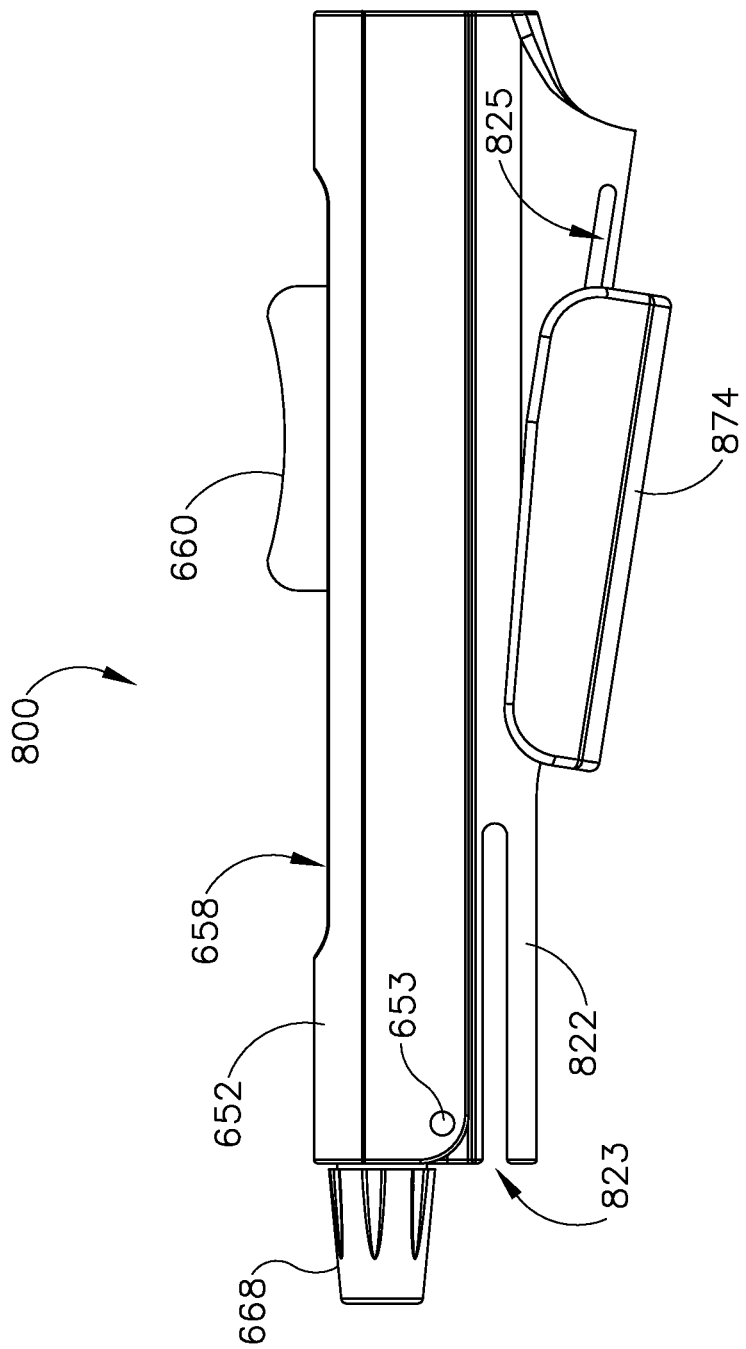
FIG. 36 depicts a side elevation view of the handle of FIG. 35.

As best seen in FIG. 34A, second body member (754) includes a through-bore (770) formed therein. Through-bore (770) extends the complete length of second body member (754). As with through bore (670) of handle (650) described above, through-bore (770) is operable to receive and selectively retain endoscope (460). Second body member (754) further includes an opening (772) formed in a bottom surface of second body member (754). Opening (772) provides external access to through-bore (770). A sled (774) is slidably coupled with second body member (754) via a pair of elongate recesses (775) formed in opposing sides of an exterior surface of second body member (754) and a pair of mating elongate projections (777) extending from an interior surface of sled (774). Sled (774) is slidable between a proximal (unlocked) position (FIG. 34A) and a distal (locked) position (FIG. 34B). As shown in FIG. 34B, with sled (774) in the distal (locked) position, a lateral member (776) of sled (774) is configured to bear against an exterior surface of endoscope (460) via opening (772) so as to lock endoscope (460) within through-bore (770). It should be appreciated that sled (774) may be slid from the distal (locked) position into the proximal (unlocked) position in order to enable reorientation or maneuvering of endoscope (460). Various suitable features that may be provided to selectively hold sled (774) in the locked position will be apparent to those of ordinary skill in the art in view of the teachings herein.

It should be appreciated that handle (750) may be grasped, oriented, and maneuvered, and actuator (760) may be translated using a single hand. For instance, while grasping handle (750), the user may use his or her index finger or thumb to orient first body member (752) relative to second body member (754) and/or to translate actuator (760).

C. Exemplary Locking Sled with Cantilevered Resilient Member

FIGS. 35-37B show yet another exemplary handle (800) having first body member (652) and its components as described above with reference to handle (650). Handle further includes another exemplary alternative second body member (804). As with handle (650) described above, the distal end of first body member (652) is pivotably coupled with a distal end of second body member (804) via pin (653) such that first body member (652) and second body member (804) are pivotable toward and away from one another about pin (653).

Figure 37A:
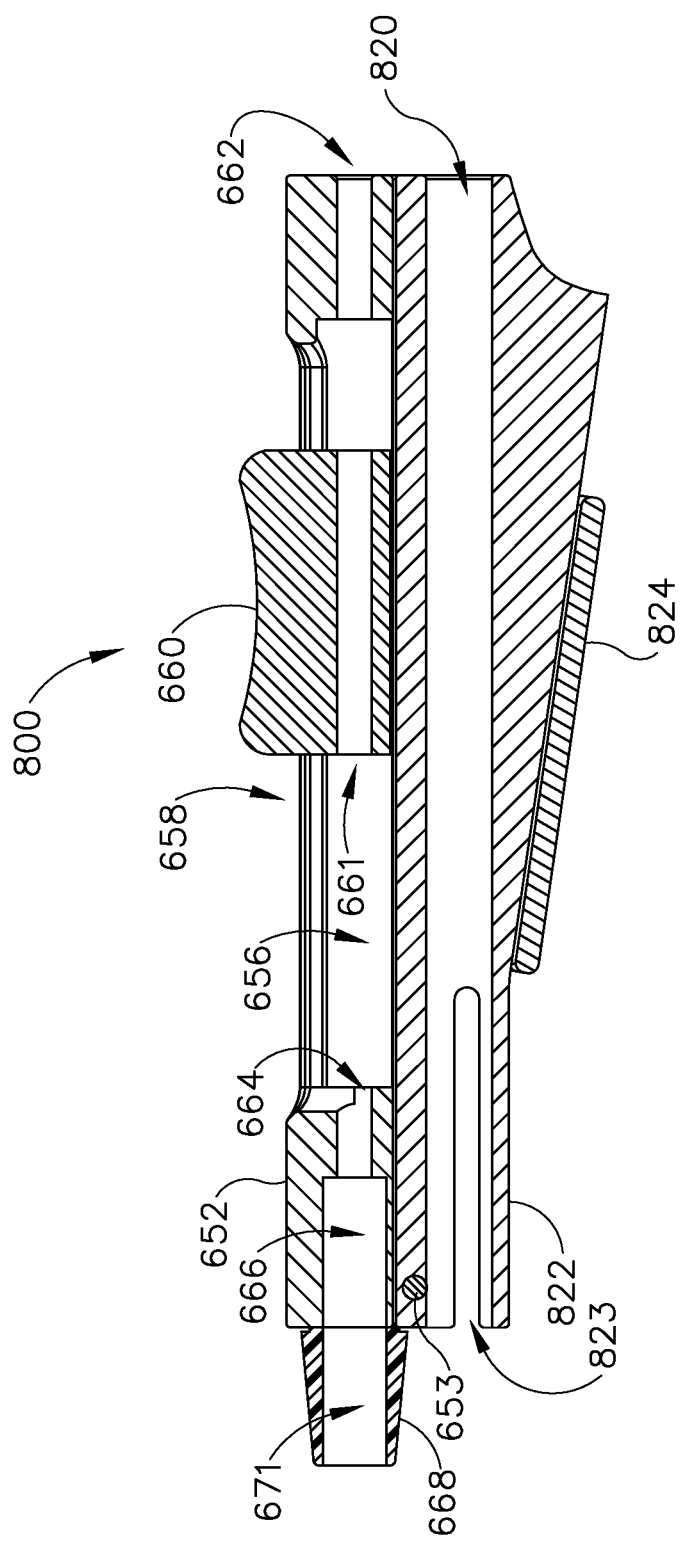
FIG. 37A depicts a cross-sectional side view of the handle of FIG. 35 taken along line 37-37 of FIG. 35 with a locking member of the handle in a first translational position.
Figure 37B:
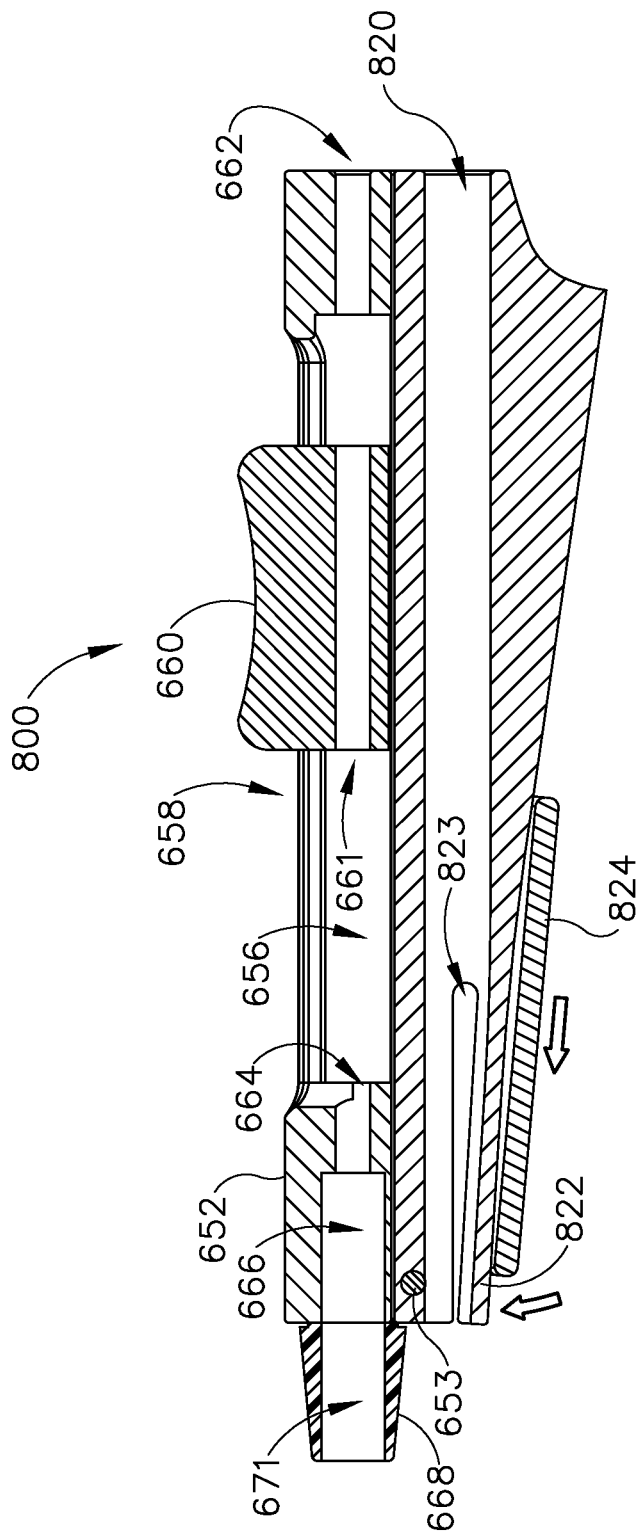
FIG. 37B depicts a cross-sectional side view of the handle of FIG. 35 taken along line 37-37 of FIG. 35 with the locking member of FIG. 37A translated into a second translational position.
Figure 38:
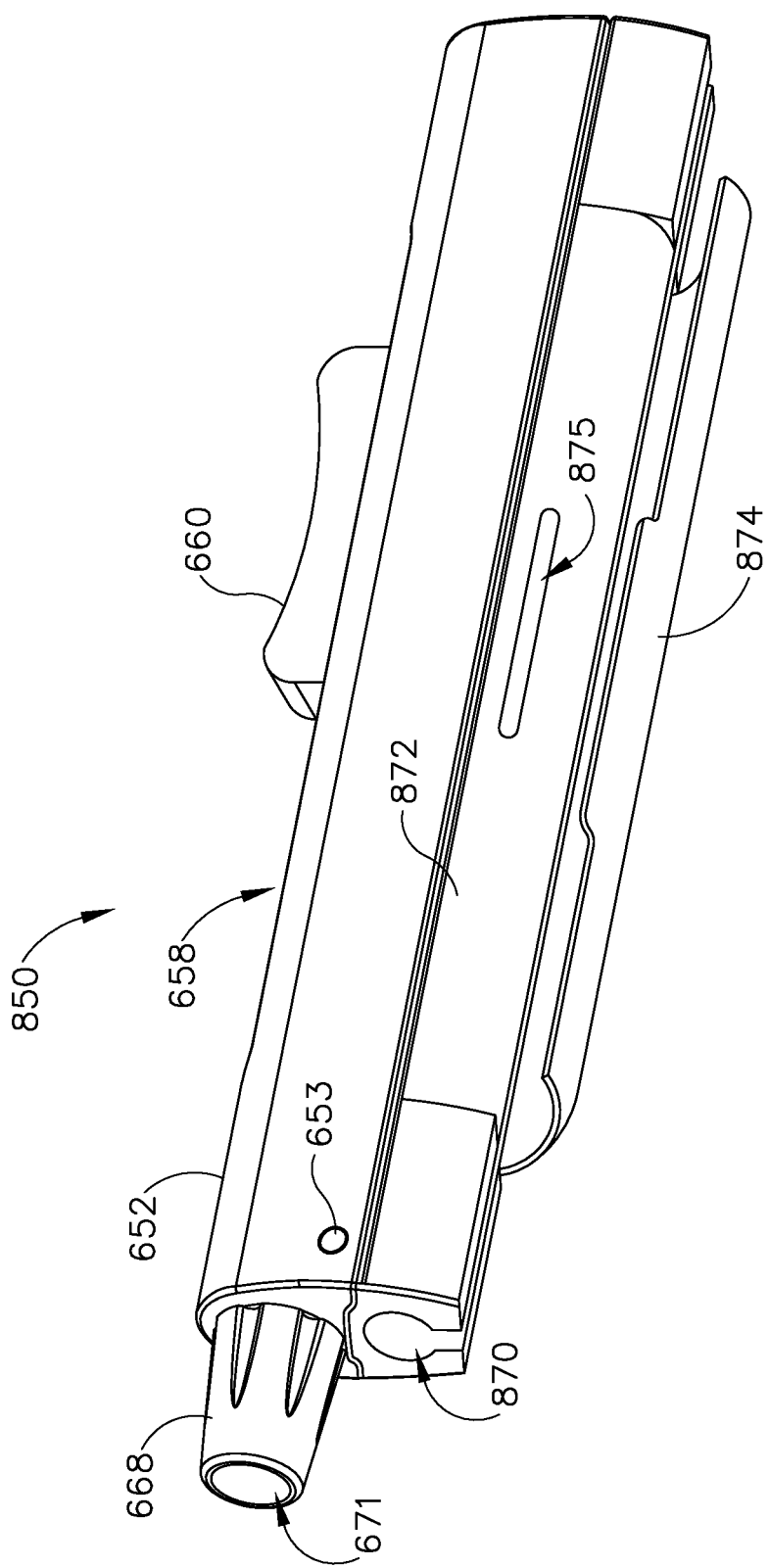
FIG. 38 depicts a perspective view of yet another exemplary handle suitable for use with the dilation catheter system of FIG. 12.

As best seen in FIG. 37A, second body member (804) includes a through-bore (820) formed therein. Through-bore (820) extends the complete length of second body member (804). As with through bore (670) of handle (650) described above, through-bore (820) is operable to receive and selectively retain endoscope (460). Second body member (804) further includes a cantilevered resilient member (822) formed in a distal end of second body member (804) via a pair of slots (823) formed in a distal end of through-bore (820). A sled (824) is slidably coupled with second body member (804) via a pair of elongate recesses (825) formed in an exterior surface of second body member (804) and a pair of mating elongate projections (not shown) extending from an interior surface of sled (824). Sled (824) is slidable between a proximal (unlocked) position (FIG. 37A) and a distal (locked) position (FIG. 37B). As shown in FIG. 37B, with sled (824) in the distal (locked) position, sled (824) is configured to bear against a bottom surface of resilient member (822) to thereby drive resilient member (822) upwardly so as to bear against an exterior surface of endoscope (460) to thereby lock endoscope (460) within through-bore (820). It should be appreciated that sled (824) may be slid from the distal (locked) position into the proximal (unlocked) position so as to allow resilient member (822) to return its original position (FIG. 37A) in order to enable reorientation or maneuvering of endoscope (460). Various suitable features that may be provided to selectively hold sled (824) in the locked position will be apparent to those of ordinary skill in the art in view of the teachings herein.

It should be appreciated that handle (800) may be grasped, oriented, and maneuvered, and actuator (810) may be translated using a single hand. For instance, while grasping handle (800), the user may use his or her index finger or thumb to orient first body member (802) relative to second body member (804) and/or to translate actuator (810).

D. Exemplary Locking Cover

FIGS. 38-40B show yet another exemplary handle (850) having first body member (652) and its components as described above with reference to handle (650). Handle (850) further includes another exemplary alternative second body member (854). As with handle (650) described above, the distal end of first body member (652) is pivotably coupled with a distal end of second body member (854) via pin (653) such that first body member (652) and second body member (854) are pivotable toward and away from one another about pin (653).

Figure 40A:
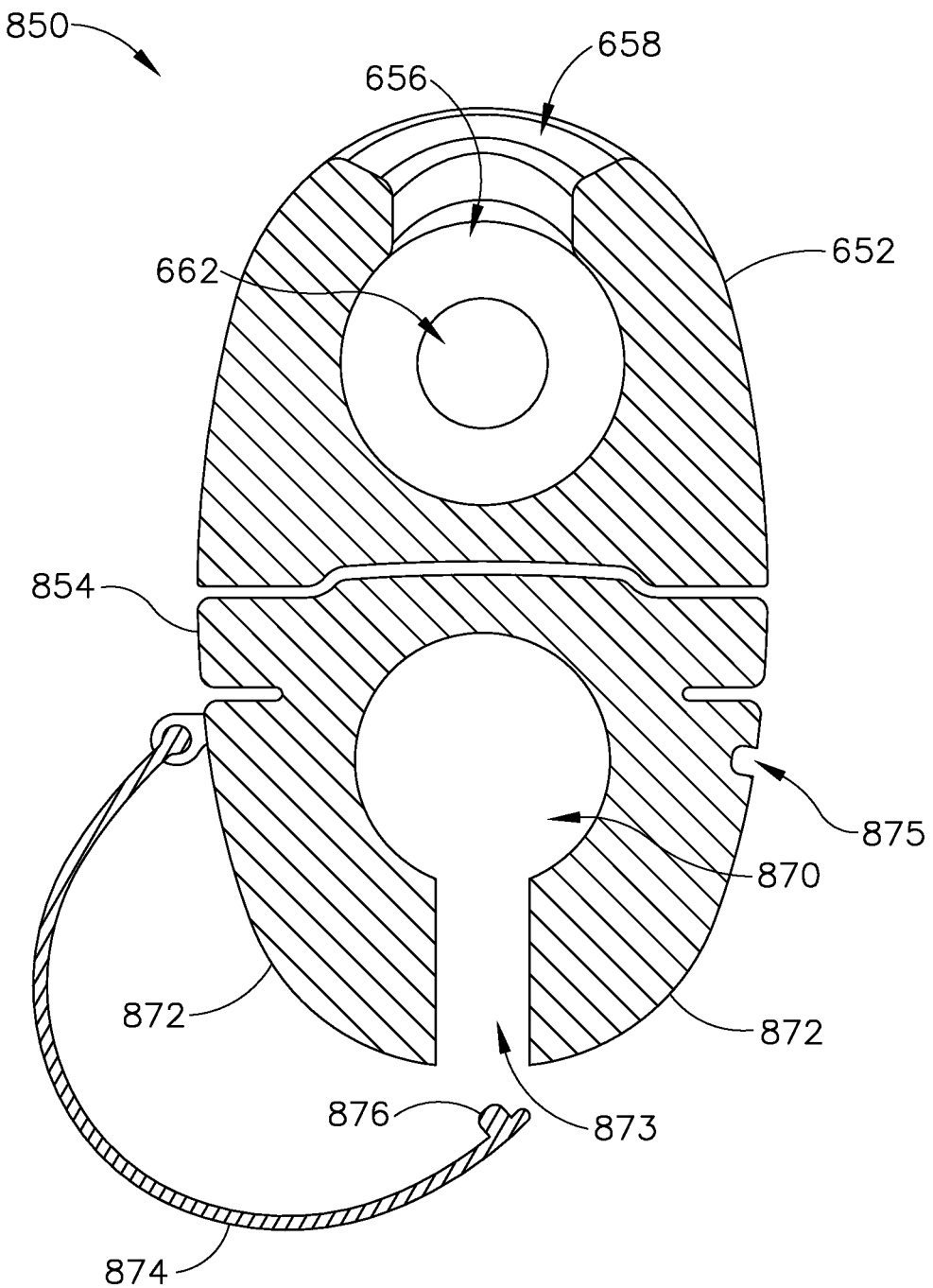
FIG. 40A depicts a cross-sectional front view of the handle of FIG. 38 taken along line 40-40 of FIG. 39, with a locking member of the handle in a first rotational position.
Figure 40B:
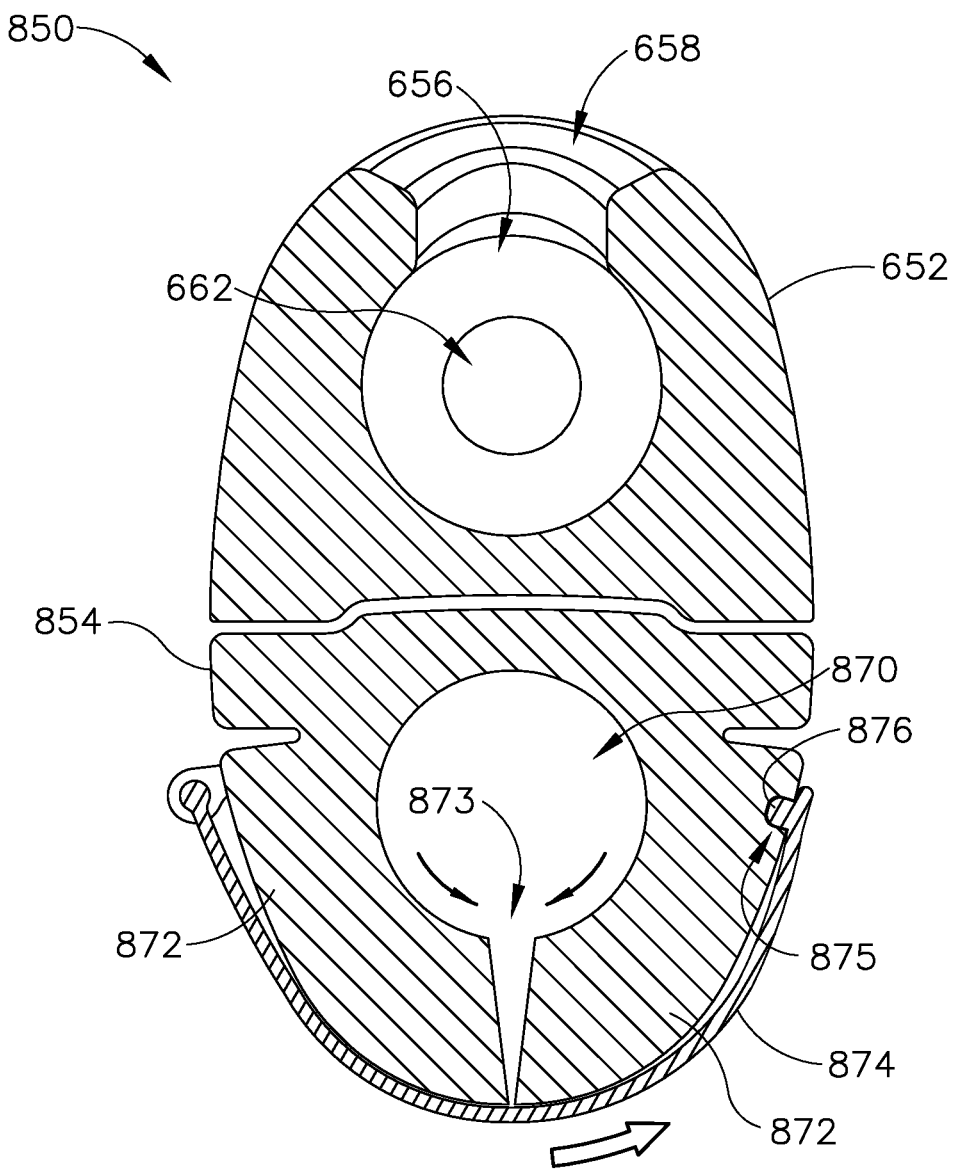
FIG. 40B depicts a cross-sectional front view of the handle of FIG. 38 taken along line 40-40 of FIG. 39, with the locking member of FIG. 40A rotated into a second rotational position.
Figure 41:
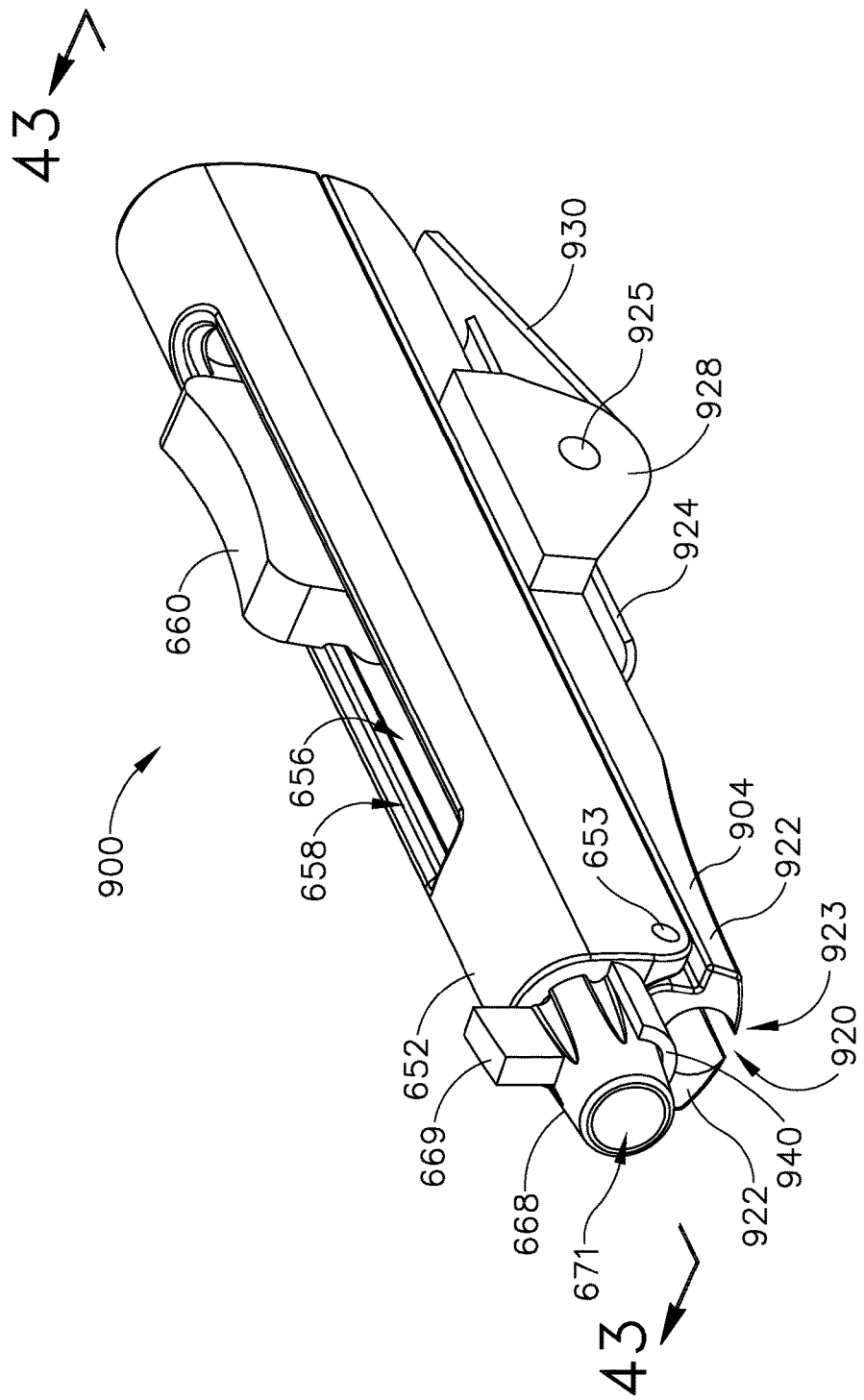
FIG. 41 depicts a perspective view of yet another exemplary handle suitable for use with the dilation catheter system of FIG. 12.
Figure 42:
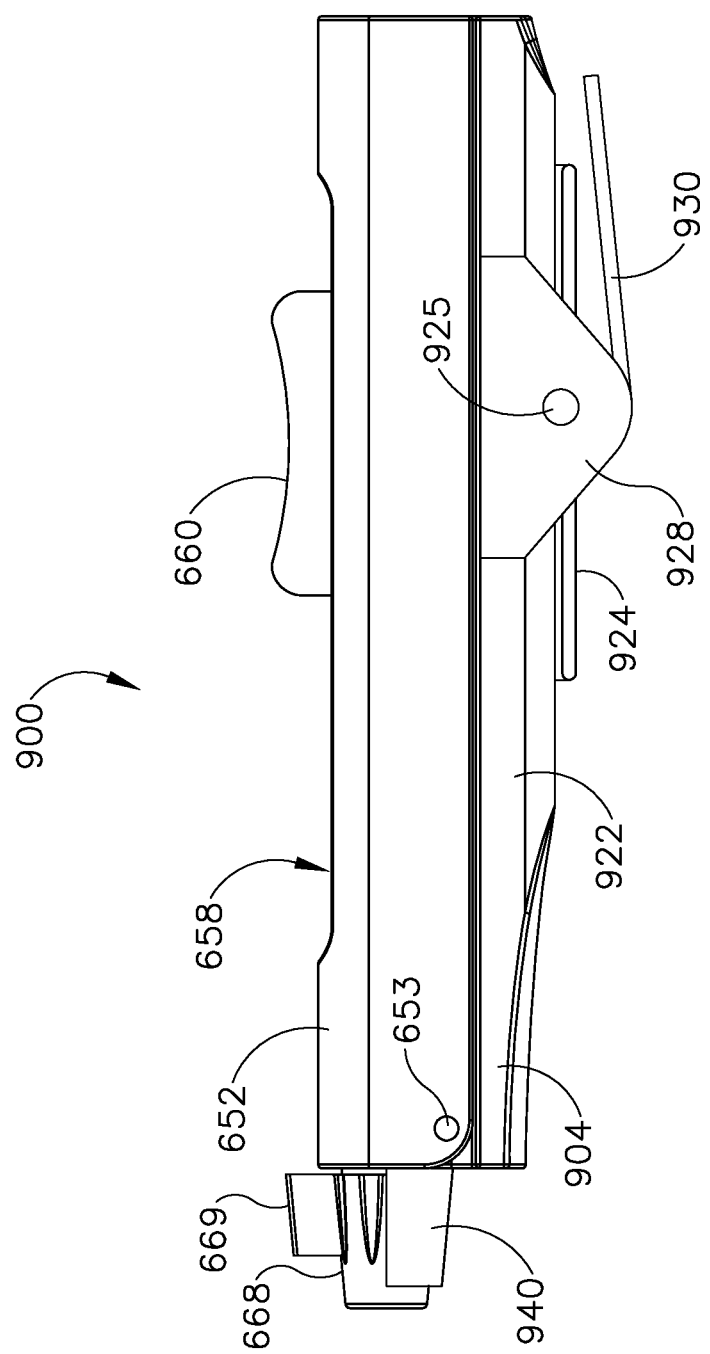
FIG. 42 depicts a side elevation view of the handle of FIG. 41.

Second body member (854) includes a through-bore (870) formed therein. Through-bore (870) extends the complete length of second body member (854). As with through bore (670) of handle (650) described above, through-bore (870) is operable to receive and selectively retain endoscope (460). Second body member (854) further includes a pair of oval-shaped flanges (872) that envelop and define a portion of through-bore (870) as shown in FIGS. 40A and 40B. A gap (873) is defined between interior surfaces of flanges (872). A semi-circular-shaped cover (874) is hingedly coupled to an exterior surface of second body member (854) such that cover (874) is operable to rotate between an unlocked position (FIG. 40A) and a locked position (FIG. 40B). As shown in FIG. 40B, with cover (874) in the locked position, cover (874) encompasses and bears against flanges (872) and drives flanges (872) inwardly toward one another so as to lock endoscope (460) within through-bore (870). An elongate recess (875) is formed in an exterior surface of second body member (854). Cover (874) comprises an elongate tab (876) configured to engage recess (875) with cover (874) in the locked position so as to selectively retain cover (874) in the locked position. It should be appreciated that cover (874) may be disengaged from recess (875) and rotated from the locked position into the unlocked position in order to enable reorientation or maneuvering of endoscope (460). Various suitable features that may be provided to selectively hold cover (874) in the locked position will be apparent to those of ordinary skill in the art in view of the teachings herein.

It should be appreciated that handle (850) may be grasped, oriented, and maneuvered, and actuator (860) may be translated using a single hand. For instance, while grasping handle (850), the user may use his or her index finger or thumb to orient first body member (852) relative to second body member (854) and/or to translate actuator (860).

E. Exemplary Locking Camming Lever

FIGS. 41-44B show yet another exemplary handle (900) having first body member (652) and its components as described above with reference to handle (650). As will be described in more detail below, however, first body member (652) of the present example comprises a feature configured to limit the amount by which rotation knob (668), and as a result guide catheter (630), may be rotated relative to first body member (652). Handle (900) further includes another exemplary alternative second body member (904). As with handle (650) described above, the distal end of first body member (652) is pivotably coupled with a distal end of second body member (904) via pin (653) such that first body member (652) and second body member (904) are pivotable toward and away from one another about pin (653).

Figure 43A:
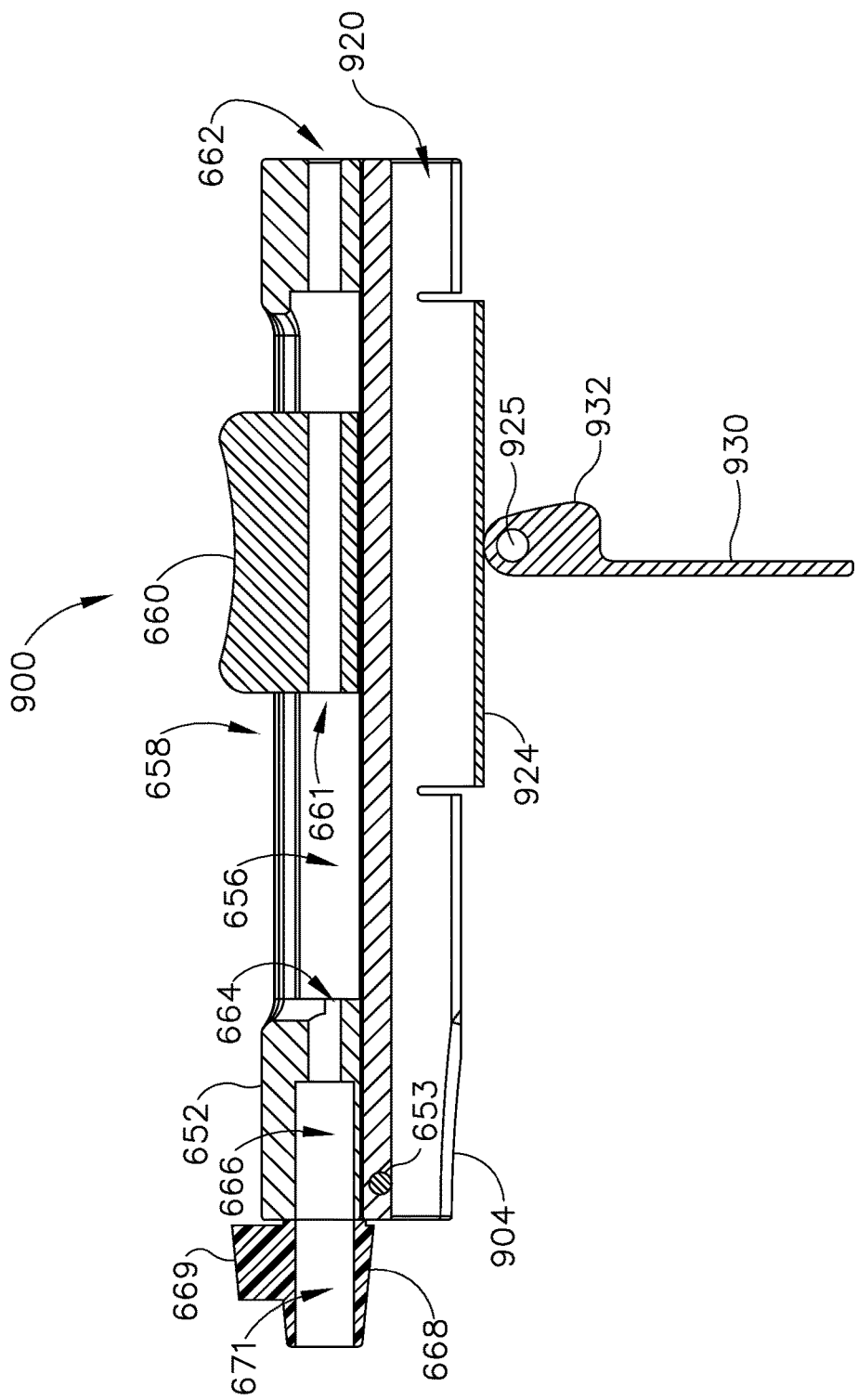
FIG. 43A depicts a cross-sectional side view of the handle of FIG. 41 taken along line 43-43 of FIG. 41, with a locking member of the handle in a first rotational position.
Figure 43B:
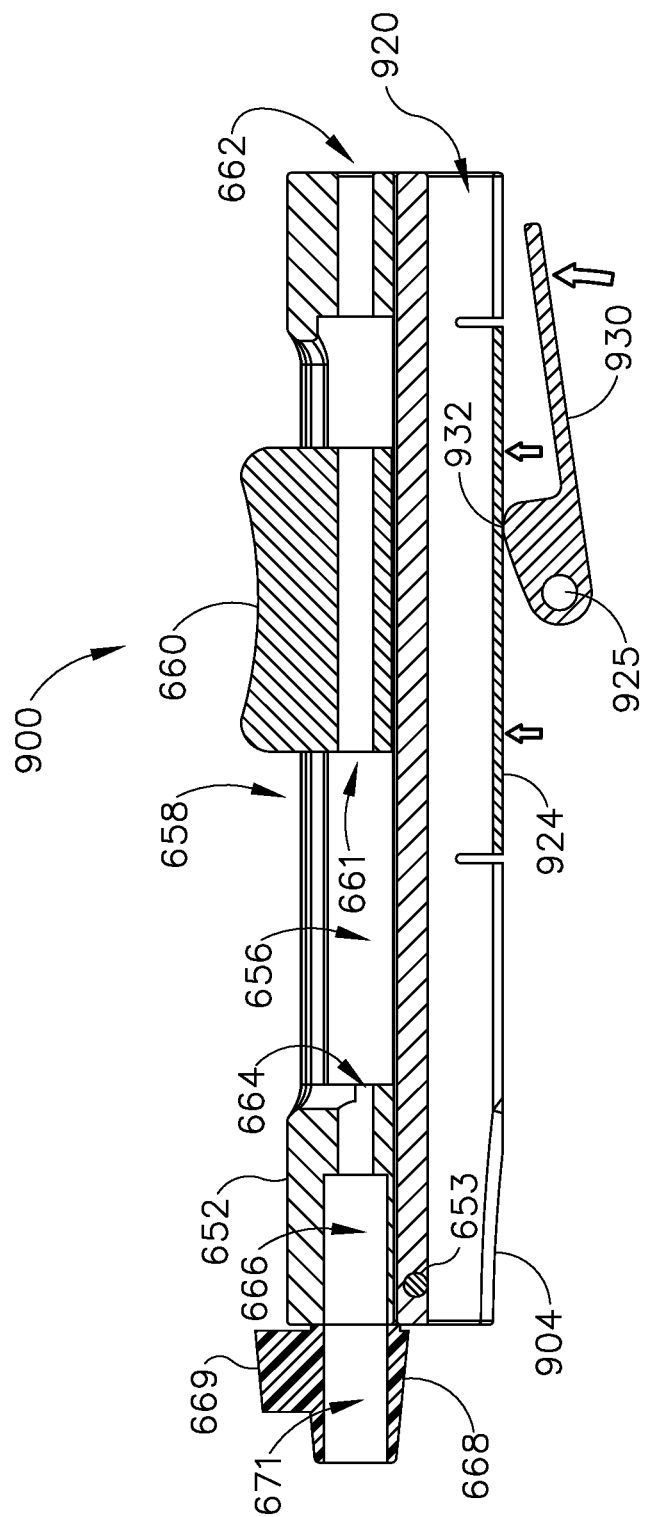
FIG. 43B depicts a cross-sectional side view of the handle of FIG. 41 taken along line 43-43 of FIG. 41, with the locking member of FIG. 43A rotated into a second rotational position.
Figure 44A:
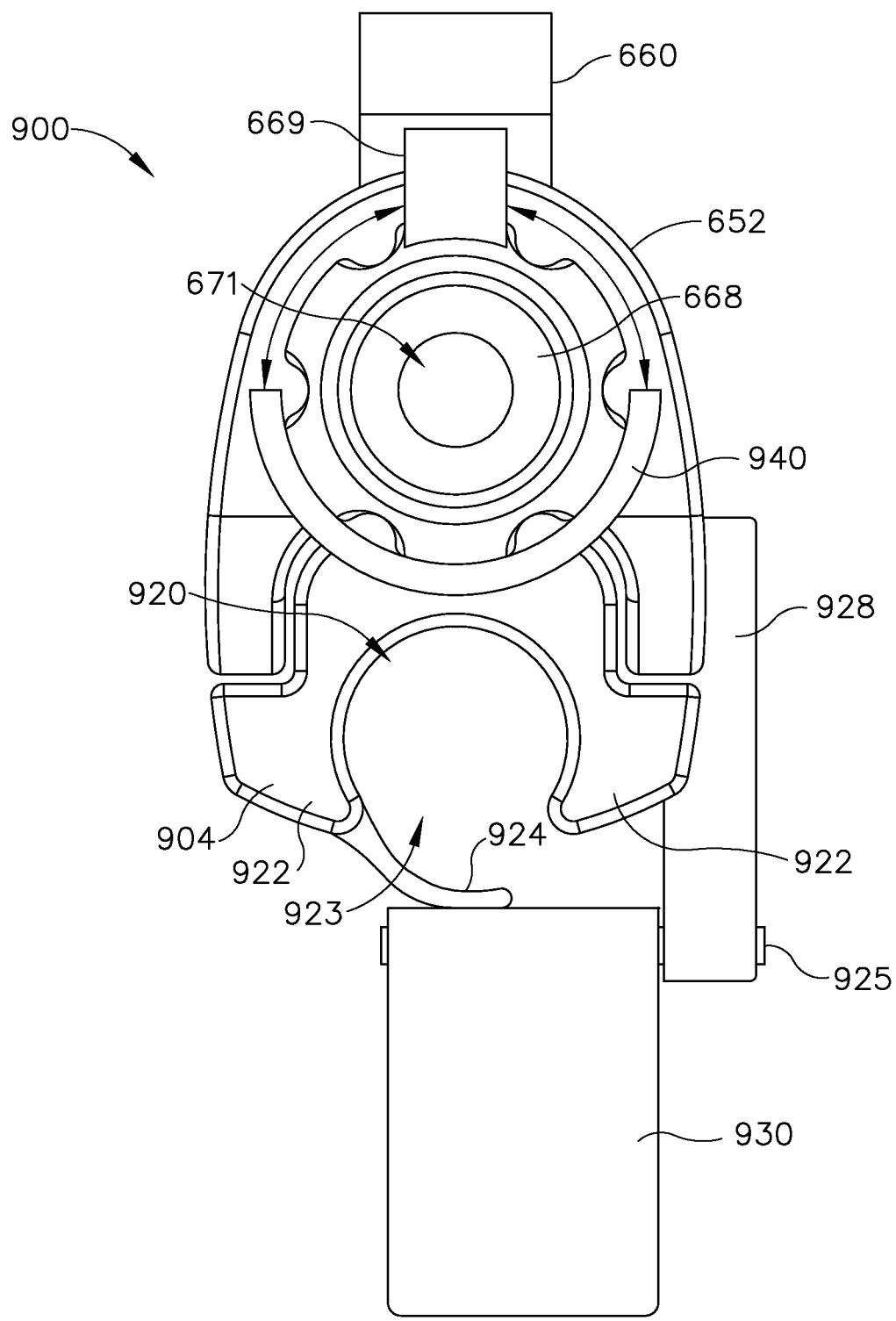
FIG. 44A depicts front elevational view of the handle of FIG. 41, with the locking member of FIG. 43A in the first rotational position.
Figure 44B:
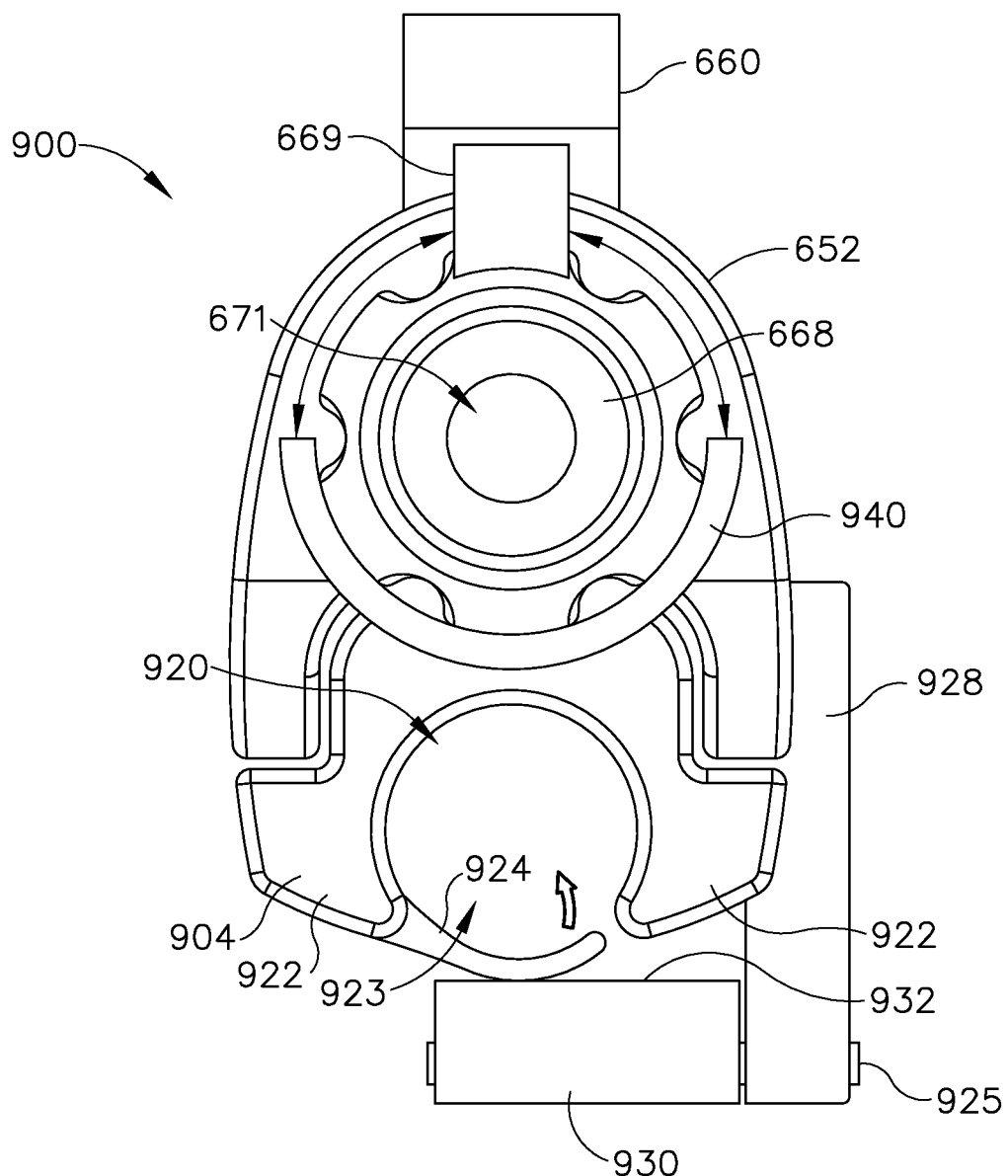
FIG. 44B depicts a front elevational view of the handle of FIG. 41, with the locking member of FIG. 43A rotated into the second rotational position.

As shown in FIGS. 43A-44B, second body member (904) includes a through-bore (920) formed therein. Through-bore (920) extends the complete length of second body member (904). As with through bore (670) of handle (650) described above, through-bore (920) is operable to receive and selectively retain endoscope (460). Second body member (904) further includes a pair of flanges (922) that envelop and define through-bore (920) as best seen in FIGS. 44A and 44B. A gap (923) is defined between interior surfaces of flanges (922). Gap (923) provides external access to through-bore (920). As best seen in FIGS. 44A and 44B, a resilient cover (924) is coupled with a first flange (922A) of flanges (922) via a living hinge and is configured to flex toward and away from the other flange (922B) of flanges (922) between an unlocked position (FIGS. 43A and 44A) and a locked position (FIGS. 43B and 44B). Resilient cover (924) is resiliently biased toward the unlocked position shown in FIGS. 44A and 44A.

A flange (928) extends downwardly from an exterior surface of second body member (904). A lever (930) is pivotably coupled with flange (928) of second body member (904) below through-bore (920) via a pin (925) such that lever (930) is pivotable toward and away from second body member (904) about pin (925) between an unlocked position (FIGS. 44A and 44B) and a locked position (FIGS. 43B and 44B). Lever (930) includes a camming surface (932) that is configured to bear against an exterior surface of resilient cover (924) such that as lever (930) is rotated from the unlocked position (FIGS. 44A and 44B) to the locked position (FIGS. 43B and 44B), resilient cover (924) is driven from the unlocked position (FIGS. 44A and 44B) to the locked position (FIGS. 43B and 44B). Thus, as shown in FIGS. 43B and 44B, with lever (930) in the locked position, resilient cover (924) is driven into the locked position and is configured to bear against an exterior surface of endoscope (460) via gap (923) so as to lock endoscope (460) within through-bore (920). It should be appreciated that lever (930) may be rotated from the locked position into the unlocked position so as to allow resilient cover (924) to return to the unlocked position in order to enable reorientation or maneuvering of endoscope (460). Various suitable features that may be provided to selectively hold lever (930) in the locked position will be apparent to those of ordinary skill in the art in view of the teachings herein.

As mentioned above, first body member (652) of the present example comprises a feature that is configured to limit the amount by which rotation knob (668), and as a result guide catheter (630), may be rotated relative to first body member (652). In particular, first body member (652) of the present example comprises a semi-circular protrusion (940) that extends distally from the distal end of first body member (652) about an exterior surface of rotation knob (668). As best seen in FIGS. 44A and 44B, semi-circular protrusion (940) partially encompasses rotation knob (668). In particular, semi-circular protrusion (940) of the present example encompasses approximately half of rotation knob (668), but may alternatively encompass any other appropriate amount of rotation knob (668). Rotation knob (668) of the present example comprises a projection (669) extending from an exterior surface of a rotation knob (668) not encompassed by semi-circular protrusion (940). As rotation knob (668) rotates, projection (669) of rotation knob (668) engages semi-circular protrusion (940) to thereby limit rotation of rotation knob (668) and as a result guide catheter (630). As mentioned above, semi-circular protrusion (940) of the present example encompasses approximately half of rotation knob (668) thereby limiting rotation of rotation knob (668) and guide catheter (630) to approximately 180 degrees. However, semi-circular protrusion (940) may alternatively encompass any other appropriate amount of rotation knob (668) to thereby further limit or allow rotation of rotation knob (668) and guide catheter (630).

It should be appreciated that handle (900) may be grasped, oriented, and maneuvered, and actuator (910) may be translated using a single hand. For instance, while grasping handle (900), the user may use his or her index finger or thumb to orient first body member (902) relative to second body member (904) and/or to translate actuator (910).

F. Exemplary Locking Sled with Cantilevered Resilient Members

Figure 45:
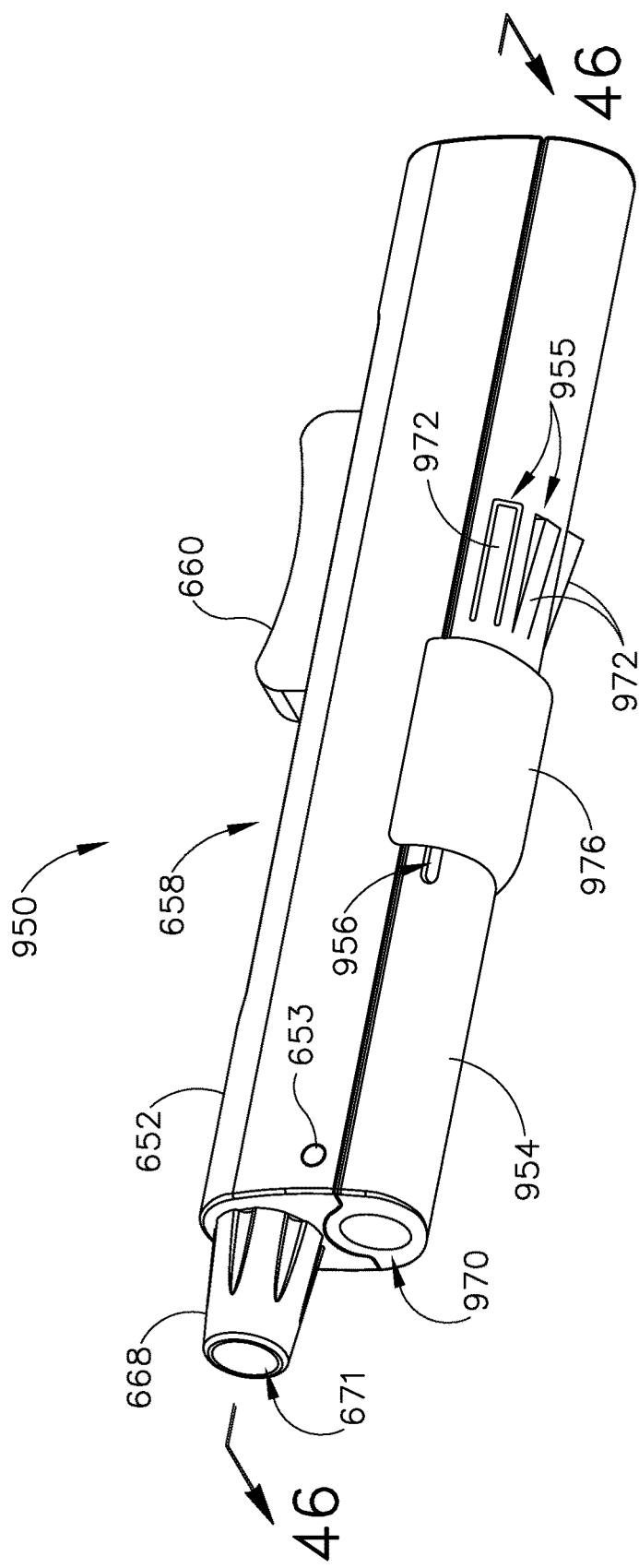
FIG. 45 depicts a perspective view of yet another exemplary handle suitable for use with the dilation catheter system of FIG. 12.
Figure 46A:
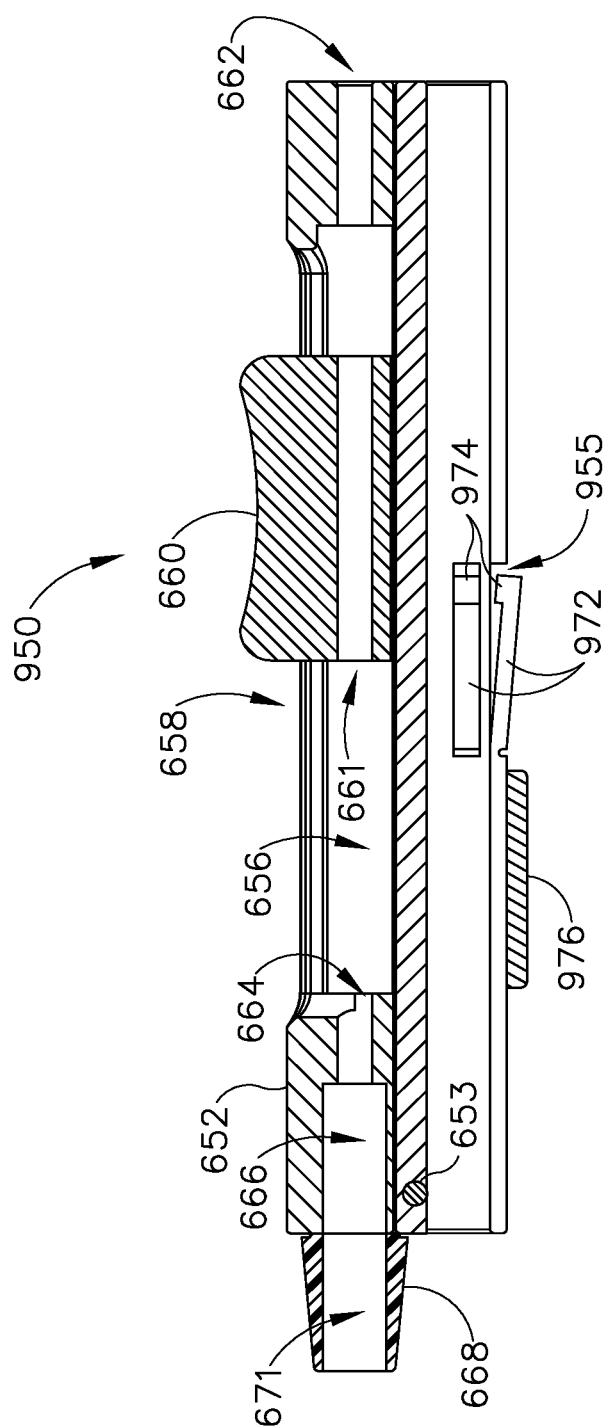
FIG. 46A depicts a cross-sectional side view of the handle of FIG. 45 taken along line 46-46 of FIG. 45, with a locking member of the handle in a first translational position.
Figure 46B:
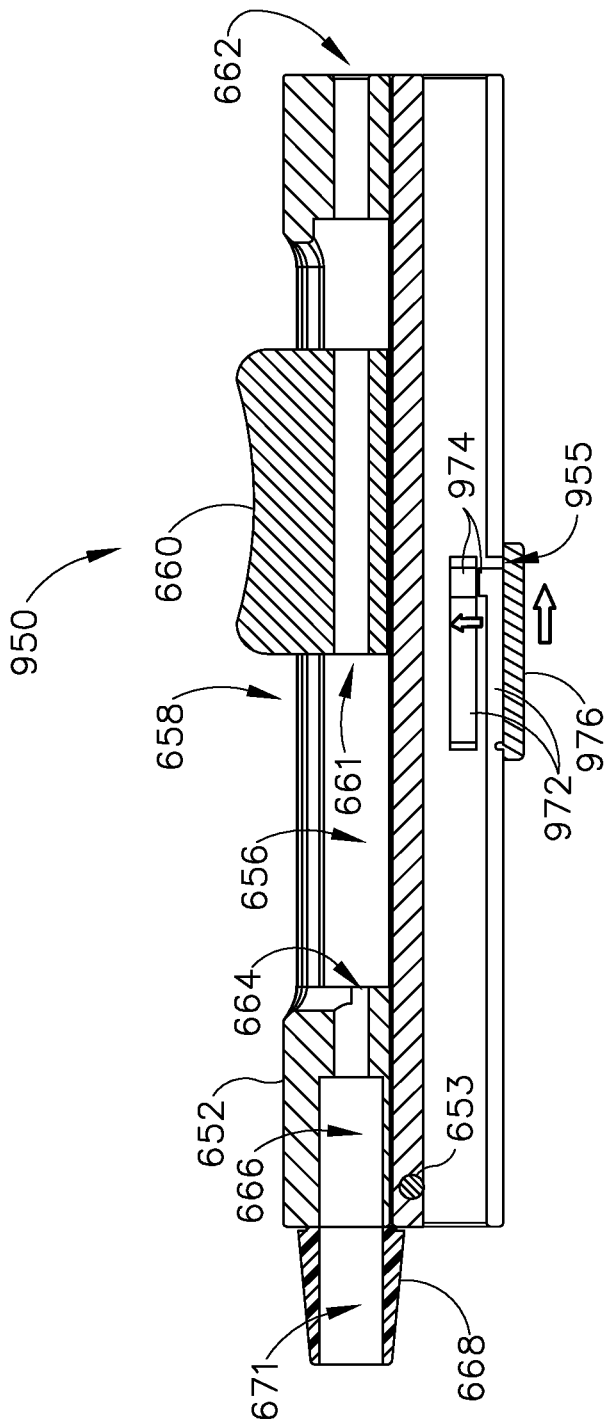
FIG. 46B depicts a cross-sectional side view of the handle of FIG. 45 taken along line 46-46 of FIG. 45, with the locking member of FIG. 46A translated into a second translational position.

FIGS. 45-46B show yet another exemplary handle (950) having first body member (652) and its components as described above with reference to handle (650). Handle further includes another exemplary alternative second body member (954). As with handle (650) described above, the distal end of first body member (652) is pivotably coupled with a distal end of second body member (954) via pin (653) such that first body member (652) and second body member (954) are pivotable toward and away from one another about pin (653).

As best seen in FIGS. 46A and 46B, second body member (954) includes a through-bore (970) formed therein. Through-bore (970) extends the complete length of second body member (954). As with through bore (670) of handle (650) described above, through-bore (970) is operable to receive and selectively retain endoscope (460). Second body member (954) further includes a plurality of cantilevered resilient members (972) formed in a sidewall of second body member (954). Resilient members (972) are angularly disposed about second body member (954) in a plurality of elongate slots (955). Each resilient member (972) includes a tab (974) extending inwardly from an unsupported end of each resilient member (972). A sled (976) is slidably coupled with second body member (954) via a pair of elongate recesses (956) formed in opposing sides of the exterior surface of second body member (954) and a pair of mating elongate projections (not shown) extending from an interior surface of sled (976). Sled (976) is slidable between a distal (unlocked) position (FIG. 46A) and a proximal (locked) position (FIG. 46B). As shown in FIG. 46B, with sled (976) in the proximal (locked) position, sled (976) is configured to bear against an exterior surface of each resilient member (972) to thereby drive resilient members (972) inwardly so as to cause tabs (974) of resilient members (972) to bear against an exterior surface of endoscope (460) to thereby lock endoscope (460) within through-bore (970). It should be appreciated that sled (974) may be slid from the proximal (locked) position into the distal (unlocked) position so as to return resilient members (972) to their original position (FIG. 46A) in order to enable reorientation or maneuvering of endoscope (460). Various suitable features that may be provided to selectively hold sled (974) in the locked position will be apparent to those of ordinary skill in the art in view of the teachings herein.

It should be appreciated that handle (950) may be grasped, oriented, and maneuvered, and actuator (960) may be translated using a single hand. For instance, while grasping handle (950), the user may use his or her index finger or thumb to orient first body member (952) relative to second body member (954) and/or to translate actuator (960).

G. Exemplary Locking Compression Lever

Figure 47:
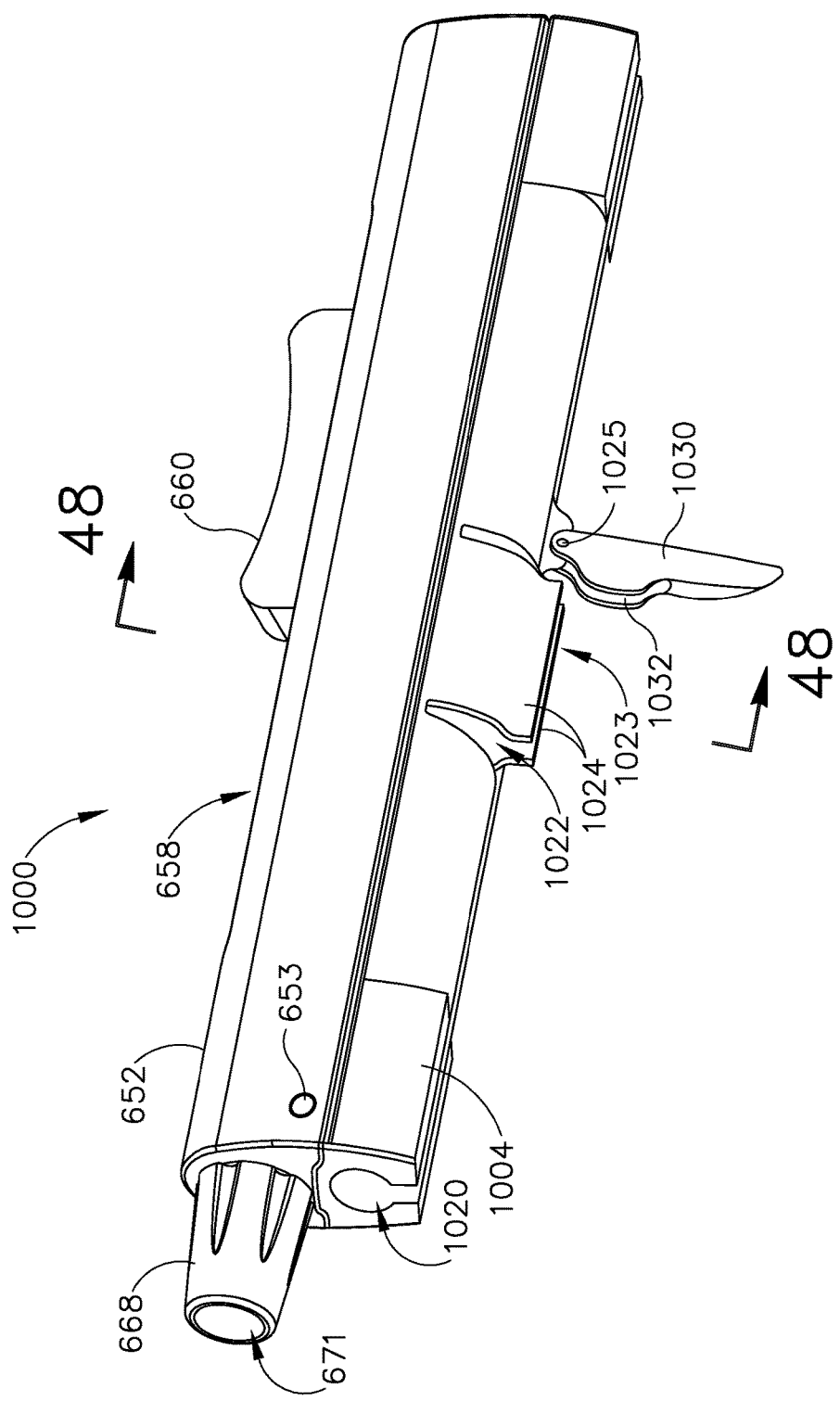
FIG. 47 depicts a perspective view of yet another exemplary handle suitable for use with the dilation catheter system of FIG. 12.
Figure 48A:
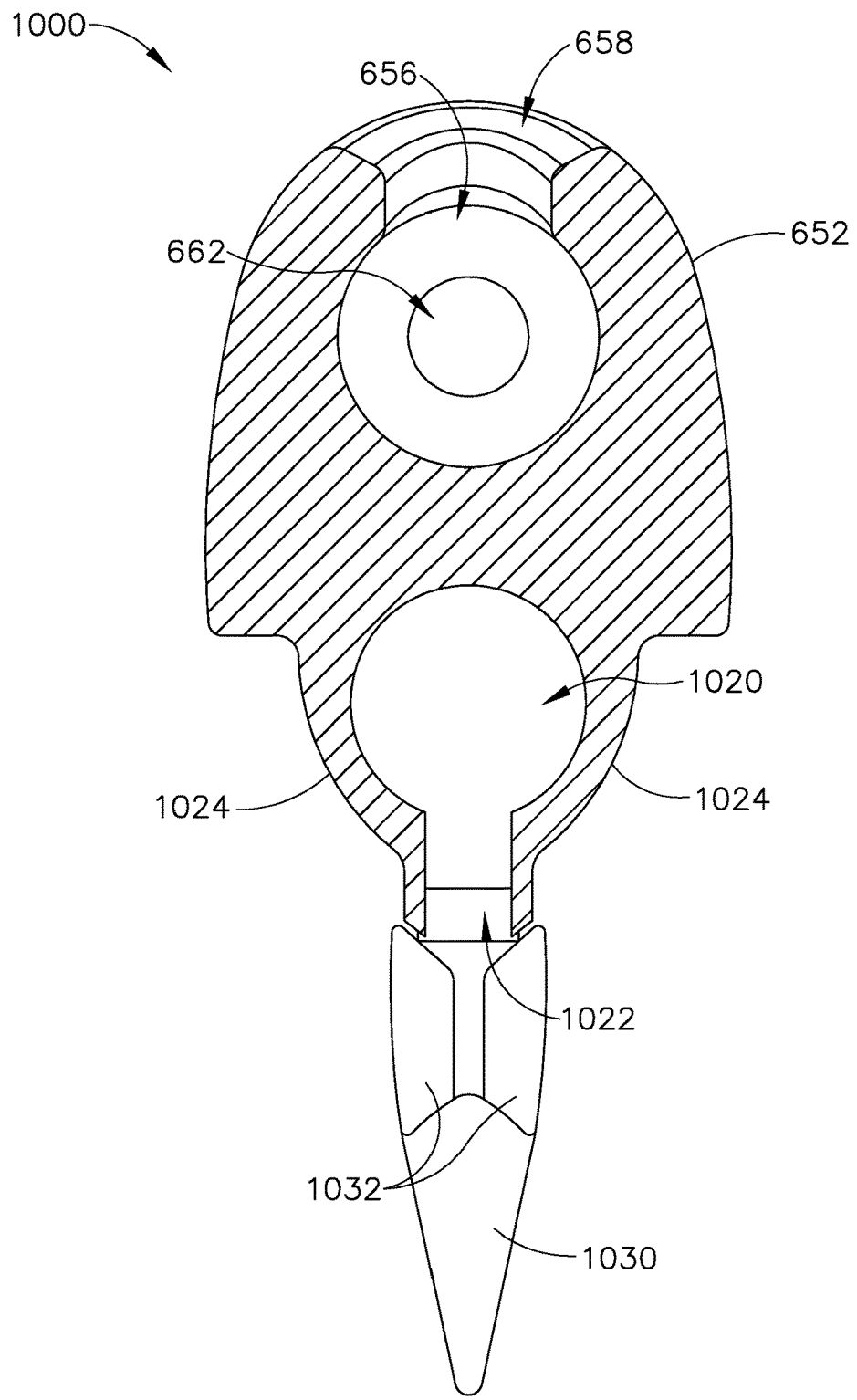
FIG. 48A depicts a cross-sectional front view of the handle of FIG. 47 taken along line 48-48 of FIG. 47, with a locking member of the handle in a first rotational position.
Figure 48B:
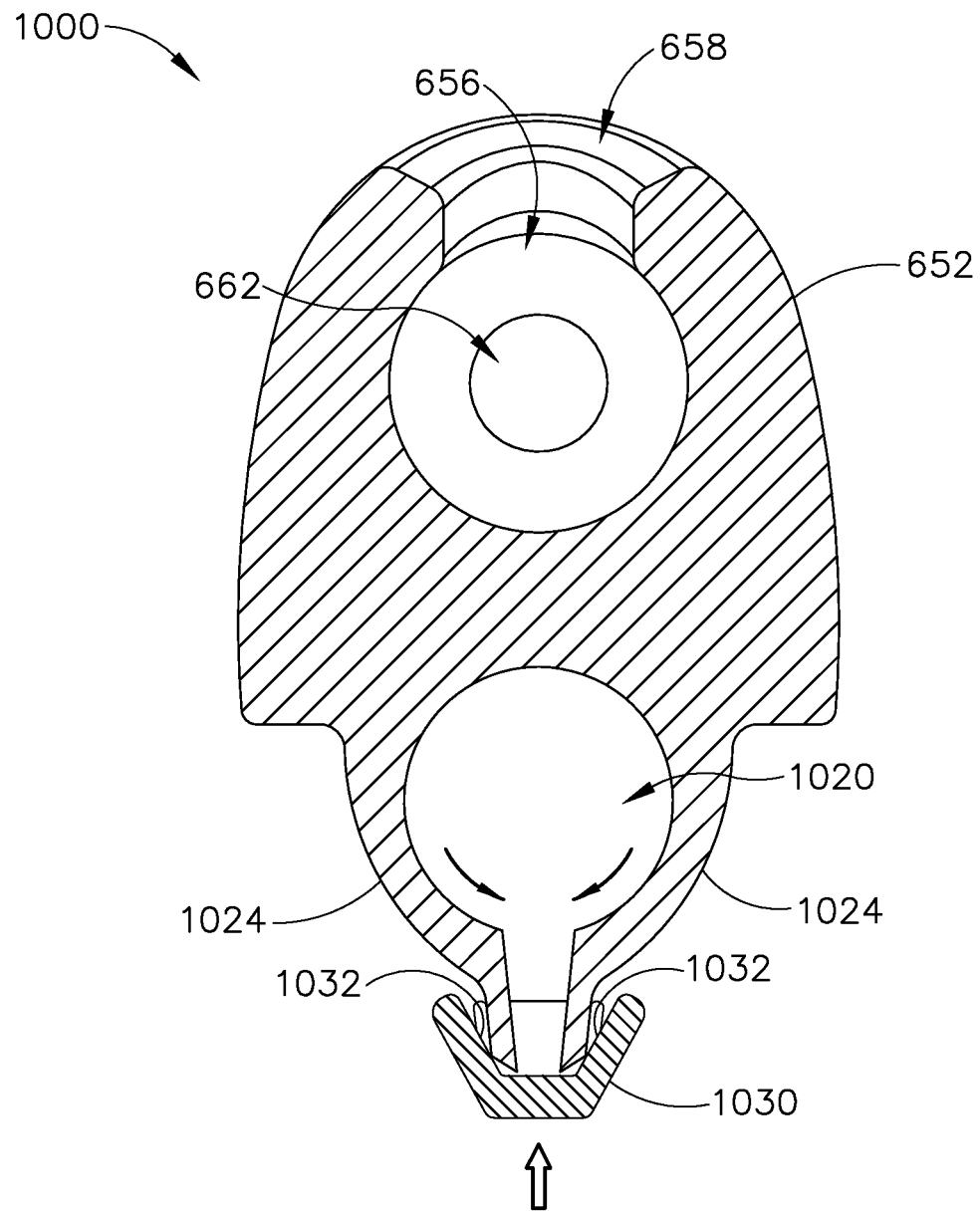
FIG. 48B depicts a cross-sectional front view of the handle of FIG. 47 taken along line 48-48 of FIG. 47, with the locking member of FIG. 48A rotated into a second rotational position.

FIGS. 47-48B show yet another exemplary handle (1000) having first body member (652) and its components as described above with reference to handle (650). Handle (1000) further includes another exemplary alternative second body member (1004). As with handle (650) described above, the distal end of first body member (652) is pivotably coupled with a distal end of second body member (1004) via pin (653) such that first body member (652) and second body member (1004) are pivotable toward and away from one another about pin (653).

Second body member (1004) includes a through-bore (1020) formed therein. Through-bore (1020) extends the complete length of second body member (1004). As with through bore (670) of handle (650) described above, through-bore (1020) is operable to receive and selectively retain endoscope (460). Second body member (1004) further includes an opening (1022) formed in a bottom surface of second body member (1004). Opening (1022) provides external access to through-bore (1020). A pair of resilient flanges (1024) are coupled with second body member (1004) via living hinges and are disposed within opening (1022) on opposing sides of second body member (1004). A gap (1023) is defined between interior surfaces of resilient flanges (1024). Resilient flanges (1024) are configured to flex toward and away from one another between an unlocked position (FIG. 48A) and a locked position (FIG. 48B). Resilient flanges (1024) are resiliently biased toward the unlocked position shown in FIG. 48A.

A lever (1030) is pivotably coupled with second body member (1004) below through-bore (1020) via a pin (1025) such that lever (1030) is pivotable toward and away from second body member (1004) about pin (1025) between an unlocked position (FIG. 48A) and a locked position (FIG. 48B). When in the locked position, lever (1030) comprises an angled interior surface (1032) that is configured to bear against exterior surfaces of resilient flanges (1024) so as to drive resilient flanges (1024) toward one another. Thus, as shown in FIG. 48B, with lever (1030) in the locked position, angled interior surface (1032) of lever (1004) is configured to bear against the exterior surfaces of resilient flanges (1024) so as to drive resilient flanges (1024) toward one another to thereby bear against an exterior surface of endoscope (460) so as to lock endoscope (460) within through-bore (1020). It should be appreciated that lever (1004) may be rotated from the locked position into the unlocked position so as to allow resilient flanges (1024) to return to the unlocked position in order to enable reorientation or maneuvering of endoscope (460). Various suitable features that may be provided to selectively hold lever (1004) in the locked position will be apparent to those of ordinary skill in the art in view of the teachings herein.

It should be appreciated that handle (1000) may be grasped, oriented, and maneuvered, and actuator (1010) may be translated using a single hand. For instance, while grasping handle (1000), the user may use his or her index finger or thumb to orient first body member (1002) relative to second body member (1004) and/or to translate actuator (1010).

H. Exemplary Locking Cover

Figure 49:
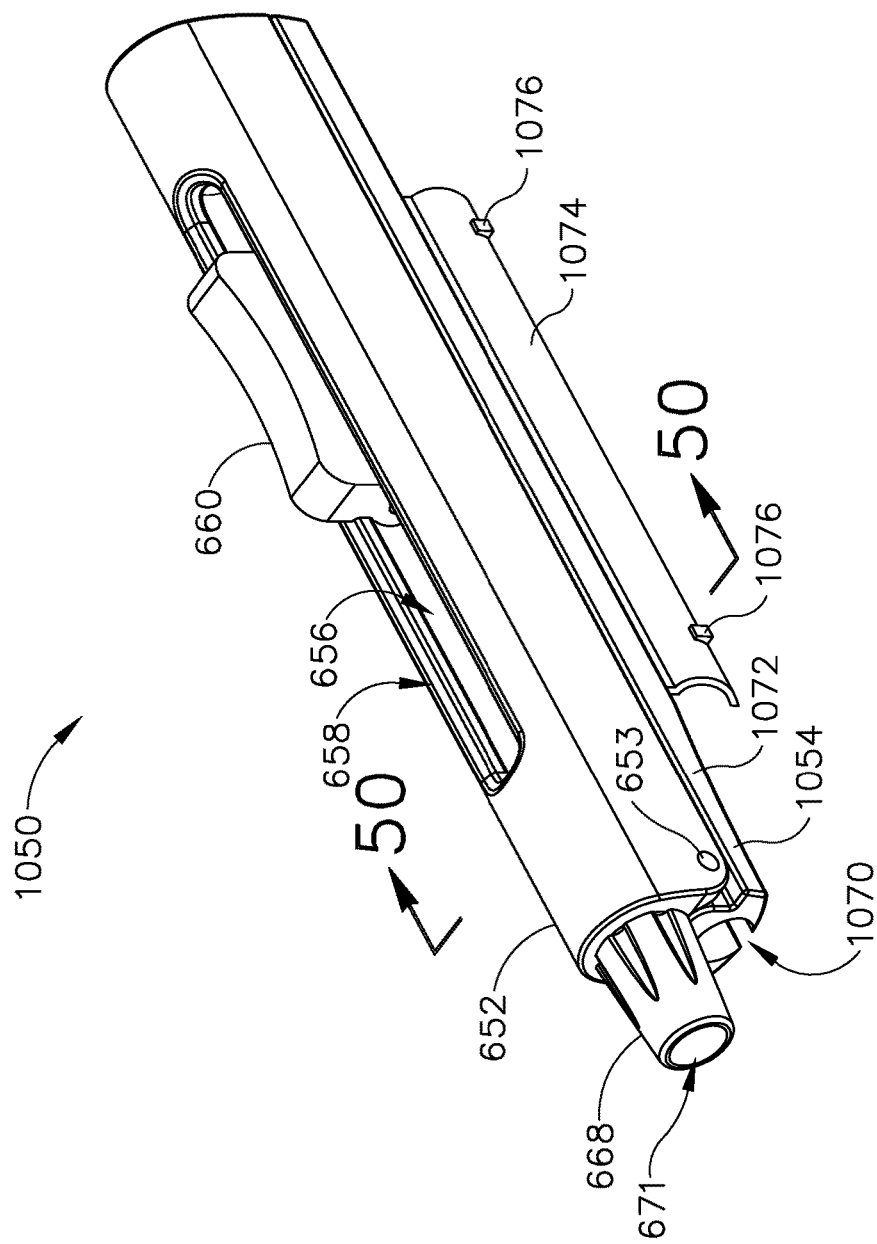
FIG. 49 depicts a perspective view of yet another exemplary handle suitable for use with the dilation catheter system of FIG. 12.
Figure 50A:
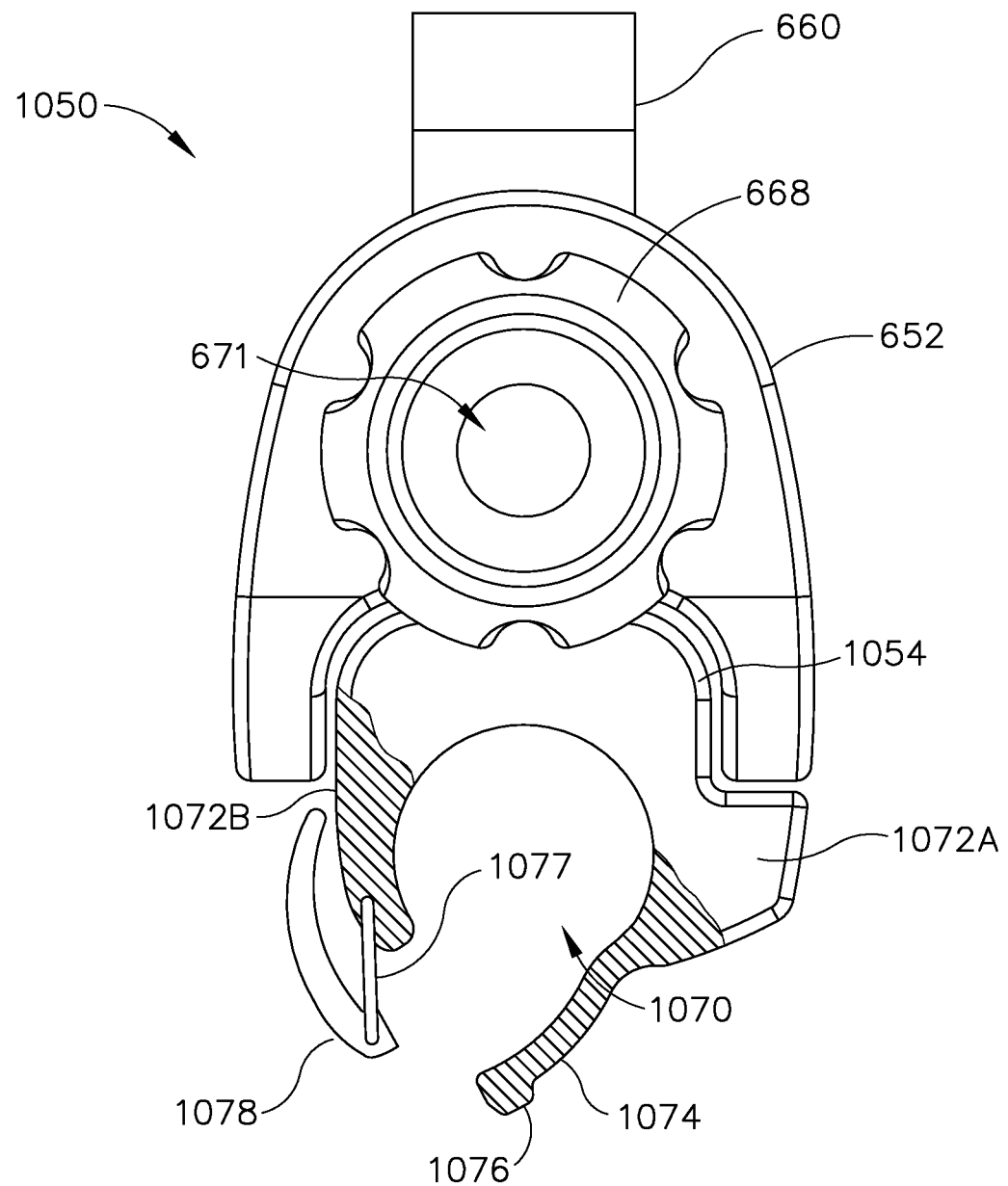
FIG. 50A depicts a cross-sectional front view of the handle of FIG. 49 taken along line 50-50 of FIG. 49, with a locking member of the handle in a first rotational position.
Figure 50B:
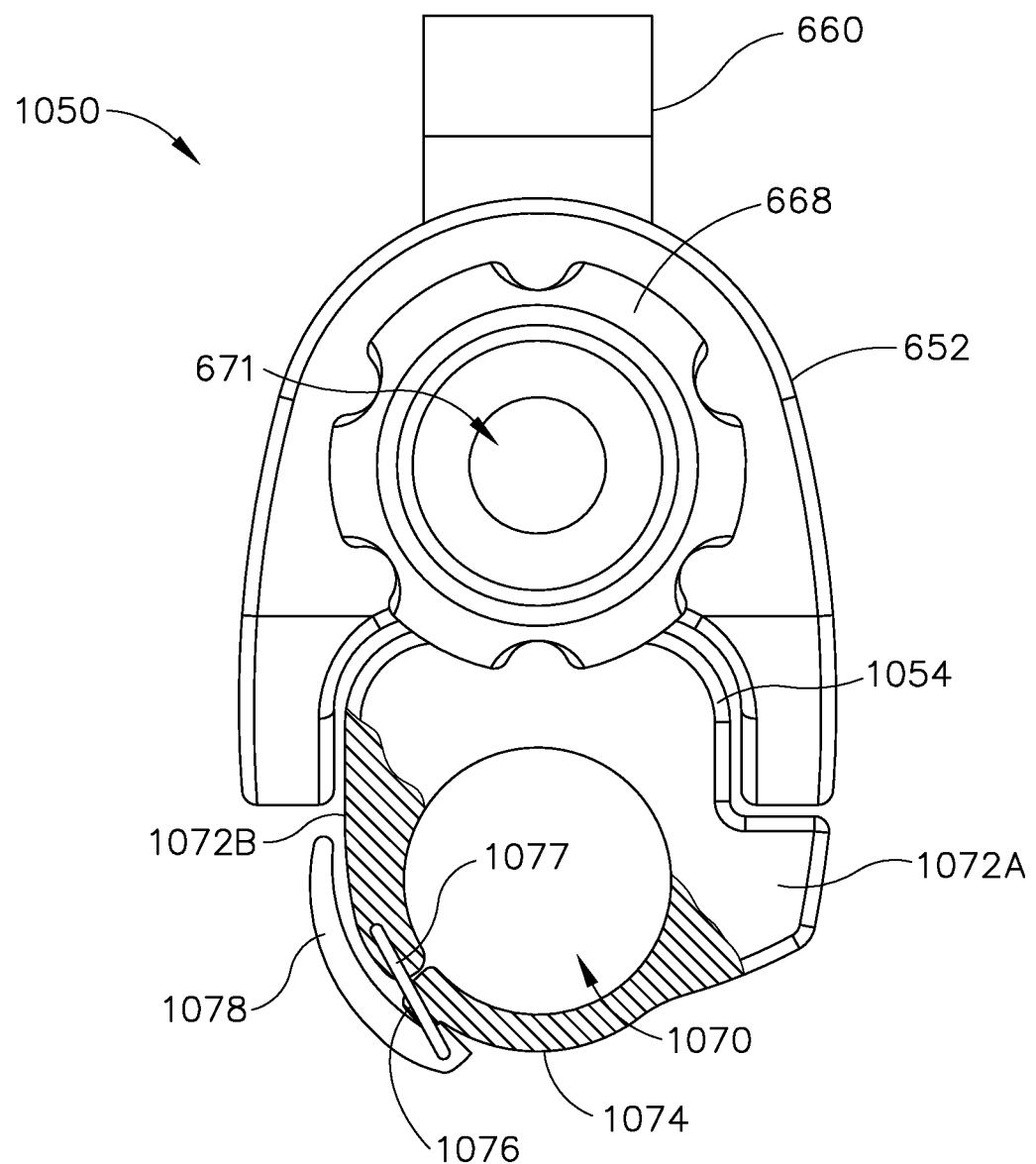
FIG. 50B depicts a cross-sectional front view of the handle of FIG. 49 taken along line 50-50 of FIG. 49, with the locking member of FIG. 50A rotated and locked into a second rotational position.

FIGS. 49-50B show yet another exemplary handle (1050) having first body member (652) and its components as described above with reference to handle (650). Handle (1050) further includes another exemplary alternative second body member (1054). As with handle (650) described above, the distal end of first body member (652) is pivotably coupled with a distal end of second body member (1054) via pin (653) such that first body member (652) and second body member (1054) are pivotable toward and away from one another about pin (653).

As best seen in FIGS. 50A and 50B, second body member (1054) includes a through-bore (1070) formed therein. Through-bore (1070) extends the complete length of second body member (1054). As with through bore (670) of handle (650) described above, through-bore (1070) is operable to receive and selectively retain endoscope (460). Second body member (1054) further includes a pair of flanges (1072) that envelop and define through-bore (1070) as best seen in FIGS. 50A and 50B. A gap (1073) is defined between interior surfaces of flanges (1072). Gap (1073) provides external access to through-bore (1070). As best seen in FIGS. 44A and 44B, a resilient cover (1074) is coupled with a first flange (1072A) of flanges (1072) via a living hinge and is configured to flex toward and away from the other flange (1072B) of flanges (1072) between an unlocked position (FIG. 50A) and a locked position (FIG. 50B). Resilient cover (1074) is resiliently biased toward the unlocked position shown in FIG. 50A. As shown in FIG. 50B, with resilient cover (1074) in the locked position, resilient cover (1074) is configured to bear against an exterior surface of endoscope (460) via gap (1073) so as to lock endoscope (460) within through-bore (1070). Resilient cover (1074) comprises a tab (1076). Second flange (1072B) comprises a latch (1078) pivotably coupled with second flange (1072B) via a linkage (1077). Latch (1078) is configured to couple about tab (1076) of resilient cover (1074) with resilient cover (1074) in the locked position to thereby selectively retain resilient cover (1074) in the locked position. It should be appreciated that resilient cover (1074) may be unlatched so as to allow resilient cover (1074) to return to the unlocked position in order to enable reorientation or maneuvering of endoscope (460). Various suitable features that may be provided to selectively hold cover (1074) in the locked position will be apparent to those of ordinary skill in the art in view of the teachings herein.

It should be appreciated that handle (1050) may be grasped, oriented, and maneuvered, and actuator (1060) may be translated using a single hand. For instance, while grasping handle (1050), the user may use his or her index finger or thumb to orient first body member (1052) relative to second body member (1054) and/or to translate actuator (1060).

I. Exemplary Locking Screw

Figure 51:
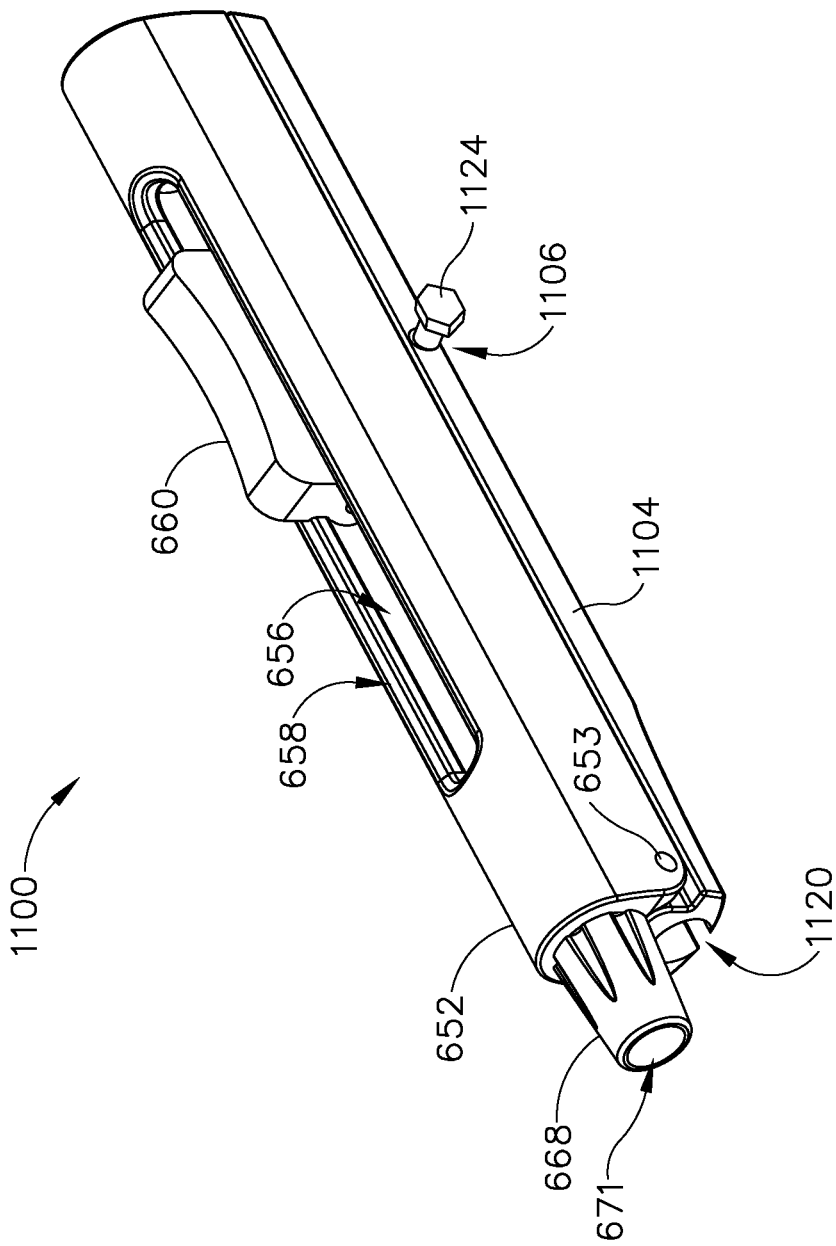
FIG. 51 depicts a perspective view of yet another exemplary handle suitable for use with the dilation catheter system of FIG. 12.
Figure 52:
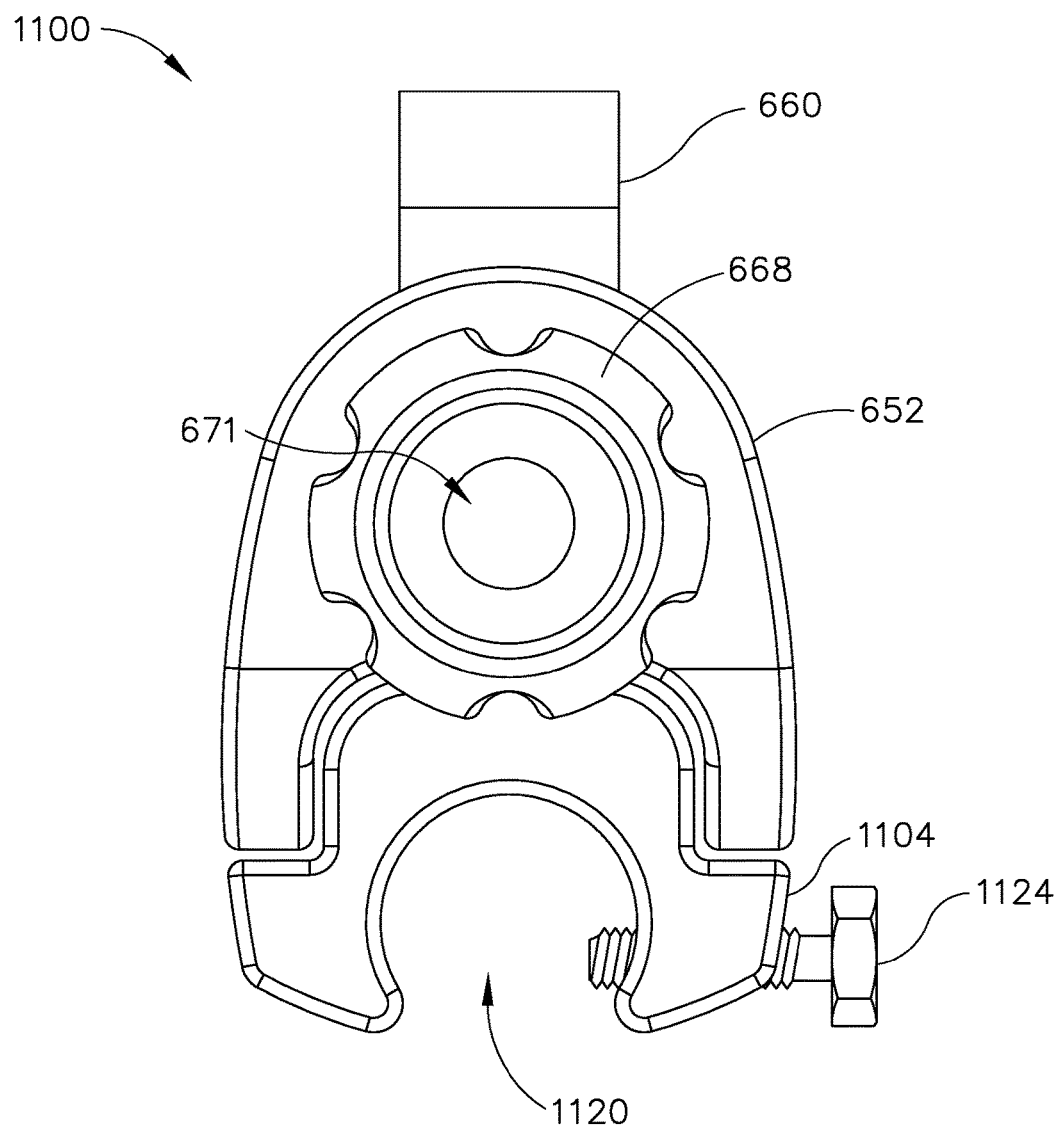
FIG. 52 depicts a front elevation view of the handle of FIG. 51.

FIGS. 51 and 52 show yet another exemplary handle (1100) having first body member (652) and its components as described above with reference to handle (650). Handle (750) further includes an exemplary alternative second body member (1104). As with handle (650) described above, the distal end of first body member (652) is pivotably coupled with a distal end of second body member (1104) via pin (653) such that first body member (652) and second body member (1104) are pivotable toward and away from one another about pin (653).

As best seen in FIG. 52, second body member (1104) includes a through-bore (1120) formed therein. Through-bore (1120) extends the complete length of second body member (1104). As with through bore (670) of handle (650) described above, through-bore (1120) is operable to receive and selectively retain endoscope (460). Second body member (1104) further includes a threaded bore (1106) formed in a sidewall of second body member (1104). Threaded bore (1106) extends from an exterior surface of second body member (1104) completely through the sidewall and into through-bore (1120). A screw/bolt (1124) is threadably engaged with threaded bore (1106) and extends completely therethrough such that a threaded portion of screw/bolt (1124) extends into through-bore (1120) and a head of screw/bolt (1124) is exposed relative to second body member (1104). Screw/bolt (1124) may be adjusted inwardly and/or outwardly relative to through-bore (1120) to thereby bear against an exterior surface of endoscope (460) so as to lock endoscope (460) within through-bore (1120). In particular, screw/bolt (1124) may be adjusted inwardly to thereby increase the amount by which screw/bolt (1124) bears against the exterior surface of endoscope (460) and/or outwardly to thereby decrease the amount by which screw/bolt (1124) bears against the exterior surface of endoscope (460). Screw/bolt (1124) may thus serve as a set screw.

It should be appreciated that handle (1100) may be grasped, oriented, and maneuvered, and actuator (1110) may be translated using a single hand. For instance, while grasping handle (1100), the user may use his or her index finger or thumb to orient first body member (1102) relative to second body member (1104) and/or to translate actuator (1110).

J. Exemplary Locking Friction Rings

Figure 53:
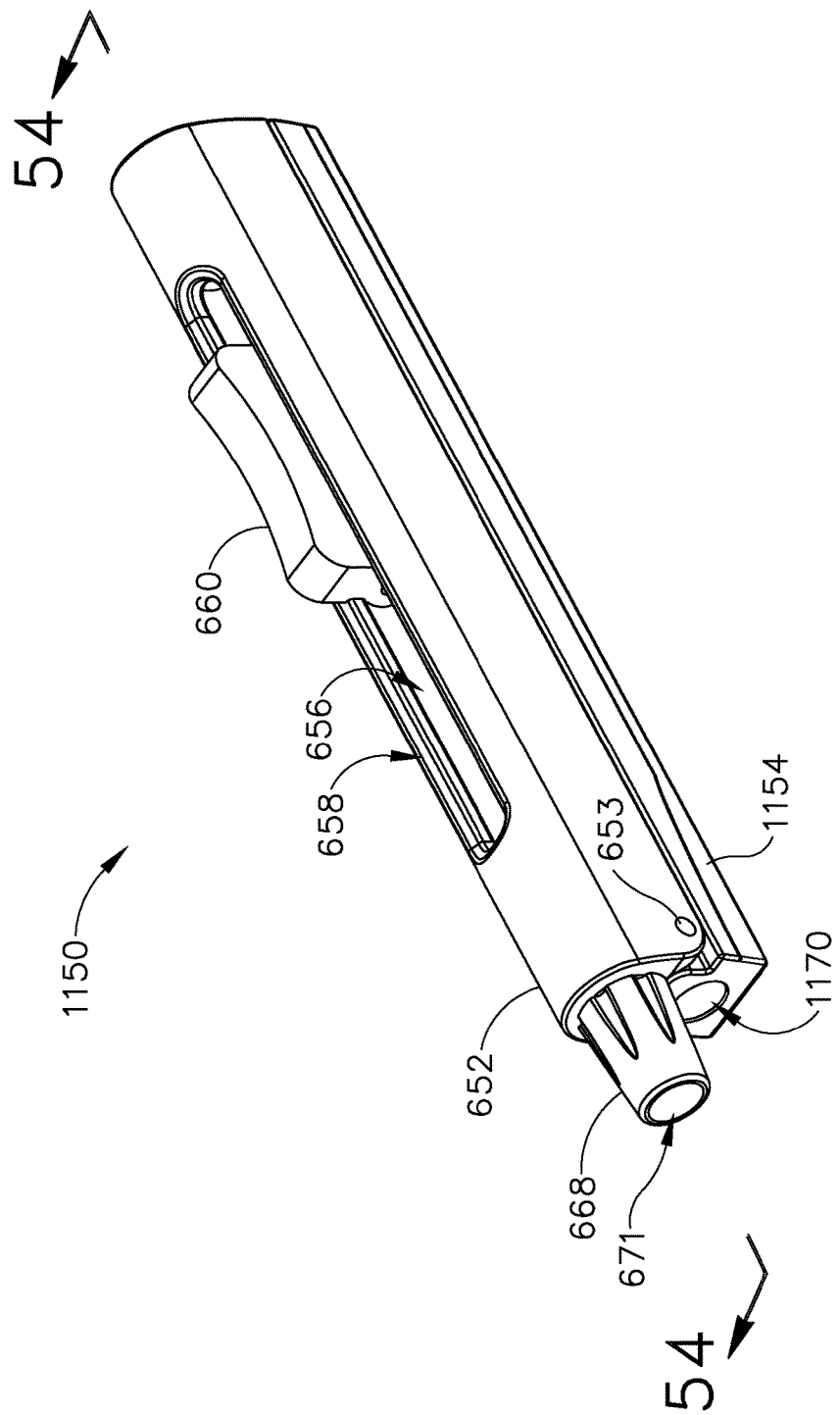
FIG. 53 depicts a perspective view of yet another exemplary handle suitable for use with the dilation catheter system of FIG. 12.
Figure 54:
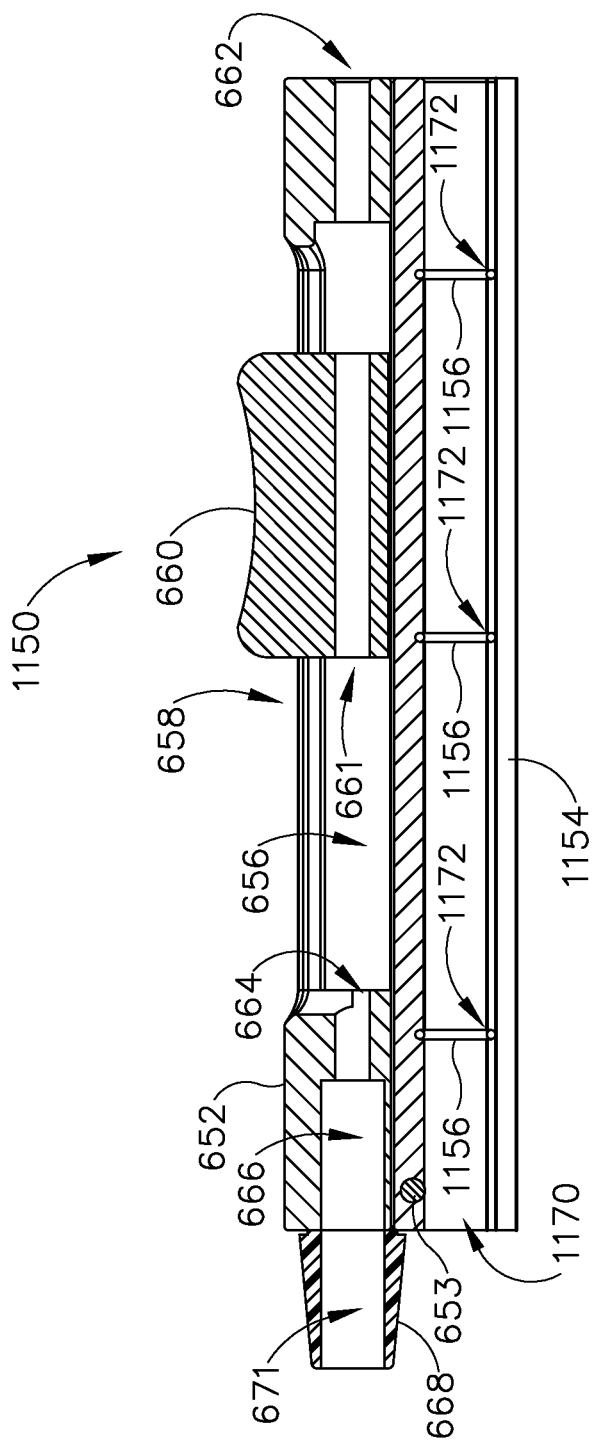
FIG. 54 depicts a cross-sectional side view of the handle of FIG. 53 taken along line 54-54 of FIG. 53.

FIGS. 53 and 54 show yet another exemplary handle (1150) having first body member (652) and its components as described above with reference to handle (650). Handle (1150) further includes an exemplary alternative second body member (1154). As with handle (650) described above, the distal end of first body member (652) is pivotably coupled with a distal end of second body member (1154) via pin (653) such that first body member (652) and second body member (1154) are pivotable toward and away from one another about pin (653).

As best seen in FIG. 54, second body member (1154) includes a through-bore (1170) formed therein. Through-bore (1170) extends the complete length of second body member (1154). As with through bore (670) of handle (650) described above, through-bore (1170) is operable to receive and selectively retain endoscope (460). Through-bore (1170) includes a plurality of annular recesses (1172) formed at spaced apart intervals in an interior surface of through-bore (1170). Second body member (1154) further includes a plurality of friction rings (1156) positioned within circular recesses (1172) of through-bore (1170). By way of example only, friction rings (1156) may comprise conventional o-rings, wiper seals, or other elastomeric members. With endoscope (460) positioned within through-bore (1170), friction rings (1156) are configured to bear against an exterior surface of endoscope (460) so as to selectively lock endoscope (460) within through-bore (1170).

It should be appreciated that handle (1150) may be grasped, oriented, and maneuvered, and actuator (1160) may be translated using a single hand. For instance, while grasping handle (1150), the user may use his or her index finger or thumb to orient first body member (1152) relative to second body member (1154) and/or to translate actuator (1160).

K. Exemplary Endoscope with Resilient Compression Members

Figure 55:
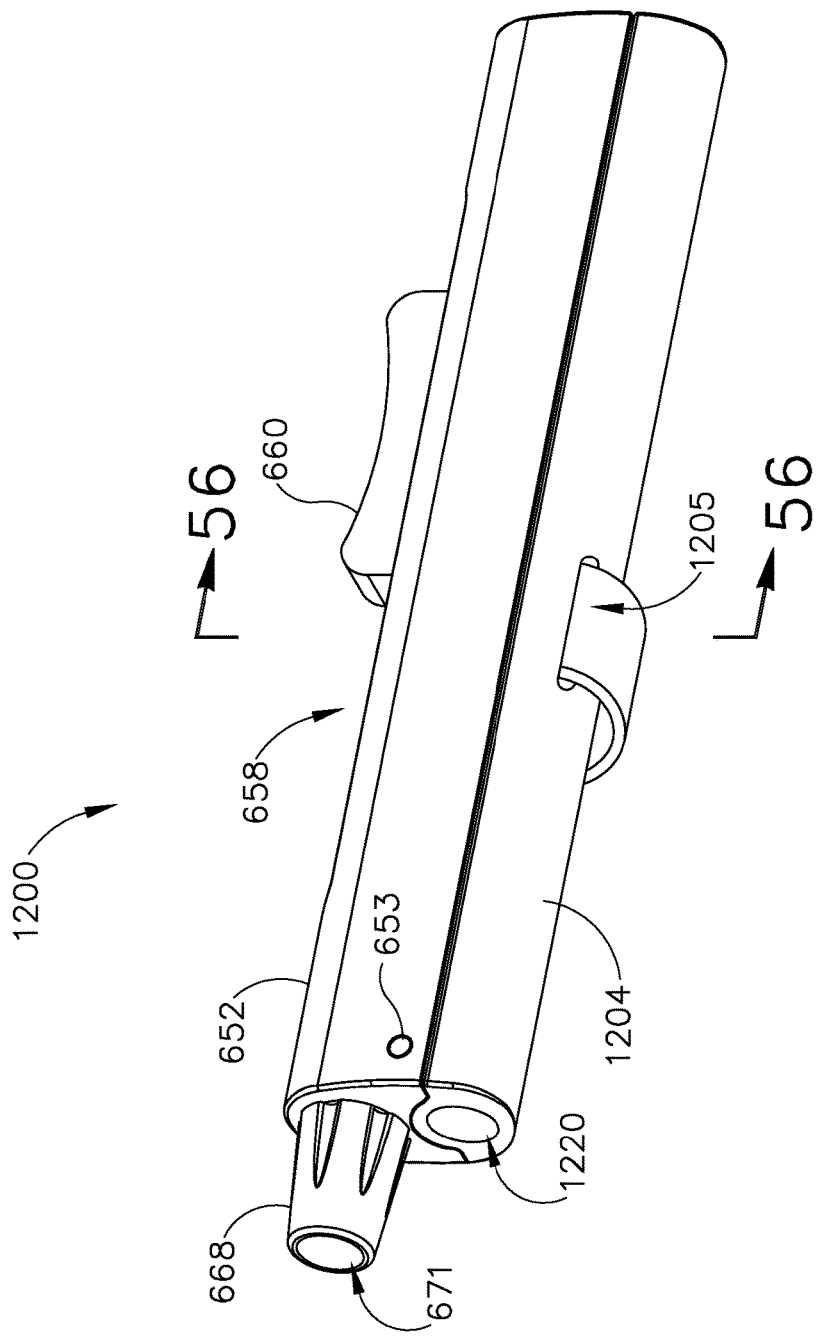
FIG. 55 depicts a perspective view of yet another exemplary handle suitable for use with the dilation catheter system of FIG. 12.
Figure 56A:
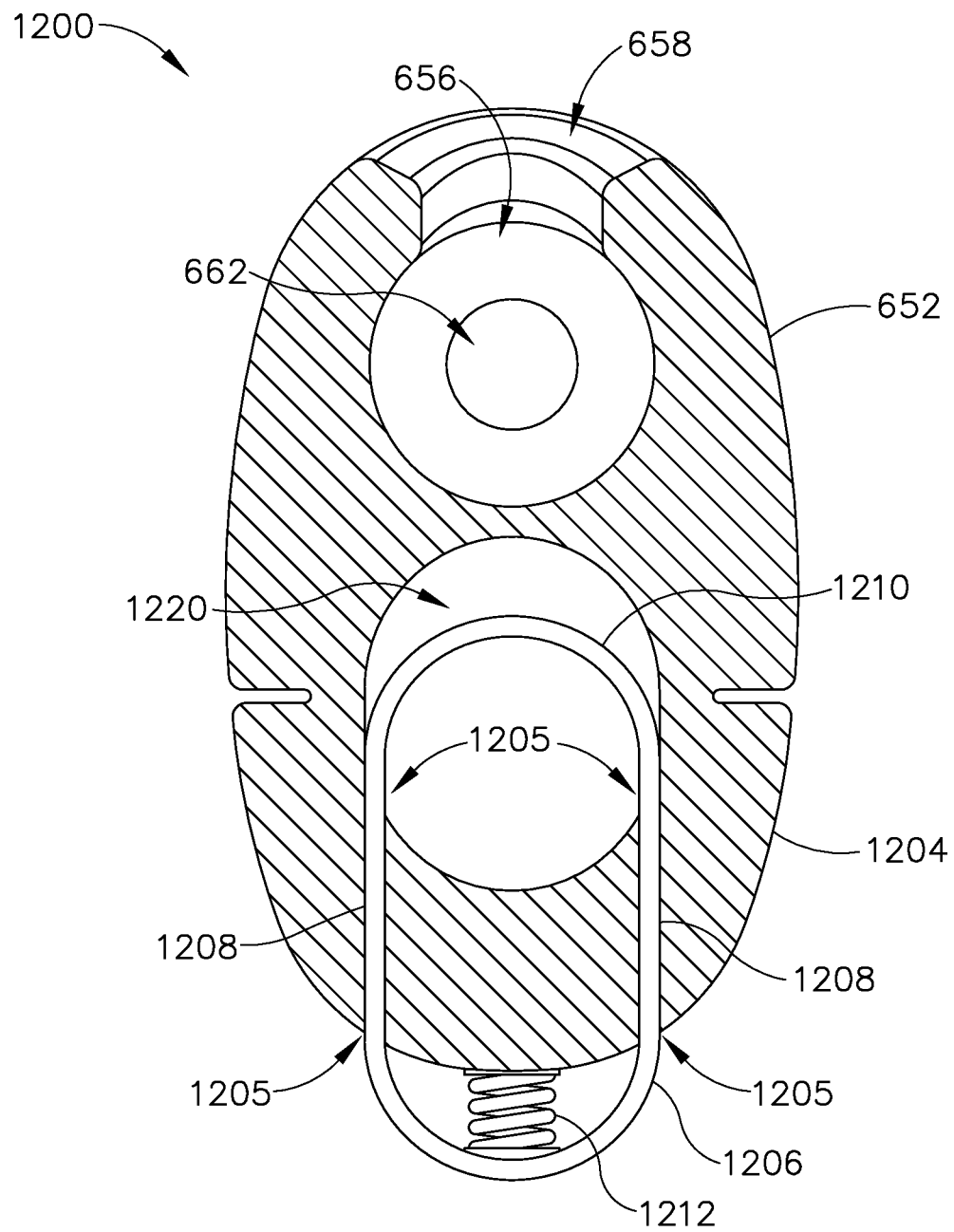
FIG. 56A depicts a cross-sectional front view of the handle of FIG. 55 taken along line 56-56 of FIG. 55, with a locking member of the handle in a first translational position.
Figure 56B:
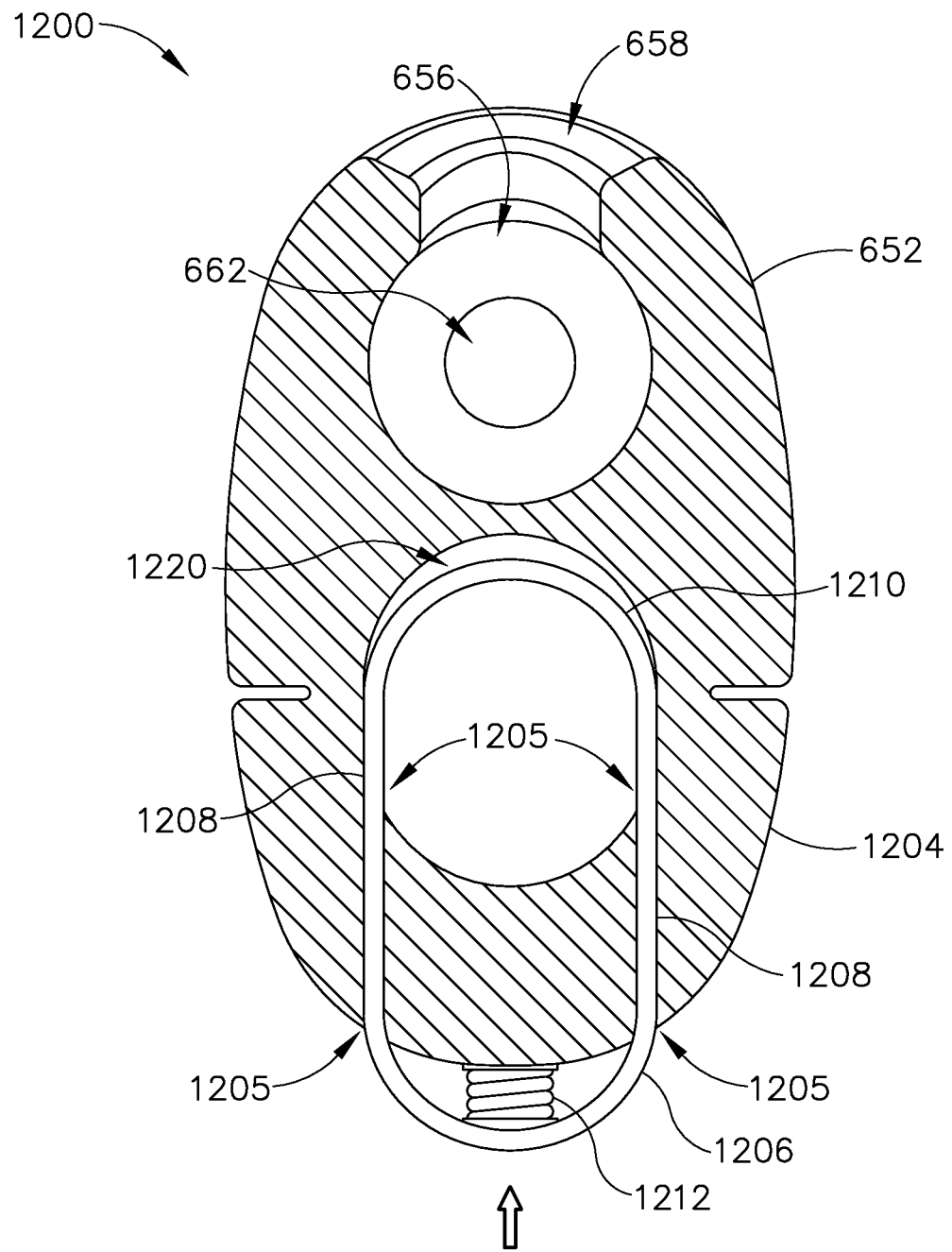
FIG. 56B depicts a cross-sectional front view of the handle of FIG. 55 taken along line 56-56 of FIG. 55, with the locking member of FIG. 56A translated into a second translational position.

FIGS. 55-56B show yet another exemplary handle (1200) having first body member (652) and its components as described above with reference to handle (650). Handle (1200) further includes an exemplary alternative second body member (1204). As with handle (650) described above, the distal end of first body member (652) is pivotably coupled with a distal end of second body member (1204) via pin (653) such that first body member (652) and second body member (1204) are pivotable toward and away from one another about pin (653).

As best seen in FIGS. 56A and 56B, second body member (1204) includes a through-bore (1220) formed therein. Through-bore (1220) extends the complete length of second body member (1204). As with through bore (670) of handle (650) described above, through-bore (1220) is operable to receive and selectively retain endoscope (460). Second body member (1204) further includes a loop-shaped button (1206). Sidewalls (1208) of button (1206) are slidably disposed within a pair of slots (1205) formed in a bottom surface of second body member (1204) below through-bore (1220) such that button (1206) is operable to slide between a locked position (FIG. 56A) and an unlocked position (FIG. 56B). A first portion (1210) of button (1206) is positioned within through-bore (1220) and a second portion (1212) of button (1206) is exposed relative to second body member (1204). A resilient member (1214) (e.g., a spring) is positioned between a bottom surface of second body member (1204) and an interior surface of button (1206) to thereby bias button (1206) toward the locked position (FIG. 56A). With endoscope (460) positioned within through-bore (1220), button (1206) is configured to bear against an exterior surface of endoscope (460) when in the locked position so as to selectively lock endoscope (460) within through-bore (1220). Button (1206) may be pressed toward the unlocked position in order to enable reorientation or maneuvering of endoscope (460).

It should be appreciated that handle (1200) may be grasped, oriented, and maneuvered, and actuator (1210) may be translated using a single hand. For instance, while grasping handle (1200), the user may use his or her index finger or thumb to orient first body member (1202) relative to second body member (1204) and/or to translate actuator (1210).

L. Exemplary Locking Lever/Door

FIGS. 29-31B show yet another exemplary handle (1250) having first body member (652) and its components as described above with reference to handle (650). Handle (750) further includes an exemplary alternative second body member (1254). As with handle (650) described above, the distal end of first body member (652) is pivotably coupled with a distal end of second body member (1254) via pin (653) such that first body member (652) and second body member (1254) are pivotable toward and away from one another about pin (653).

Figure 57:
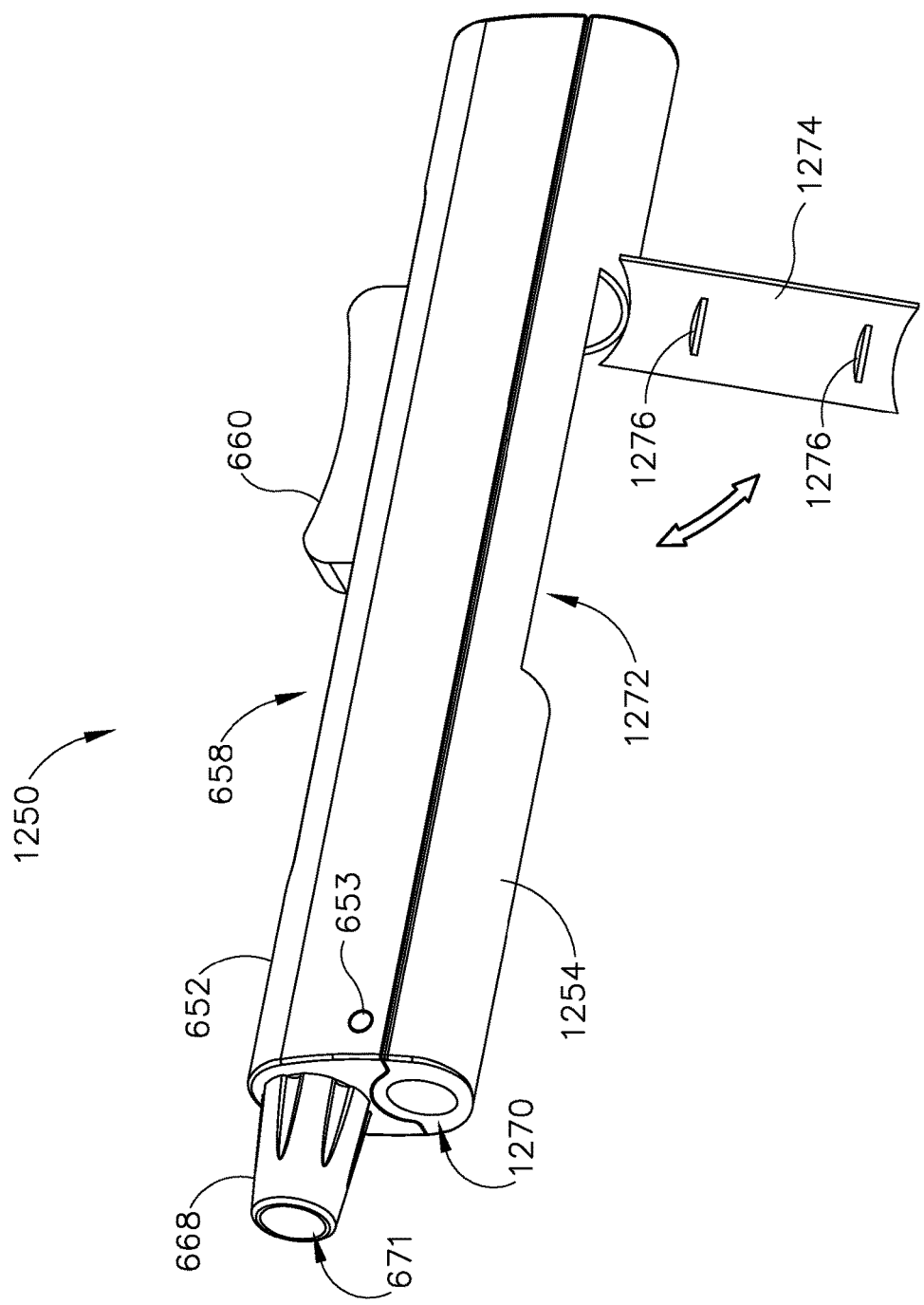
FIG. 57 depicts a perspective view of yet another exemplary handle suitable for use with the dilation catheter system of FIG. 12.

Second body member (1254) includes a through-bore (1270) formed therein. Through-bore (1270) extends the complete length of second body member (1254). As with through bore (670) of handle (650) described above, through-bore (1270) is operable to receive and selectively retain endoscope (460). Second body member (1254) further includes an opening (1272) formed in a bottom surface of second body member (1254). Opening (1272) provides external access to through-bore (1270). A lever/door (1274) is pivotably coupled with second body member (1254) below through-bore (1270) such that lever (1274) is pivotable toward and away from second body member (1254) between an unlocked position (FIG. 57) and a locked position. With lever (1274) in the locked position, a pair of lateral members (1276) of lever (1274) are configured to bear against an exterior surface of endoscope (460) via opening (1272) so as to lock endoscope (460) within through-bore (1270). It should be appreciated that lever (1274) may be rotated from the locked position into the unlocked position in order to enable reorientation or maneuvering of endoscope (460). Various suitable features that may be provided to selectively hold lever (1274) in the locked position will be apparent to those of ordinary skill in the art in view of the teachings herein.

It should be appreciated that handle (1250) may be grasped, oriented, and maneuvered, and actuator (1260) may be translated using a single hand. For instance, while grasping handle (1250), the user may use his or her index finger or thumb to orient first body member (1252) relative to second body member (1254) and/or to translate actuator (1260).

M. Exemplary Locking Endoscope

Figure 58A:
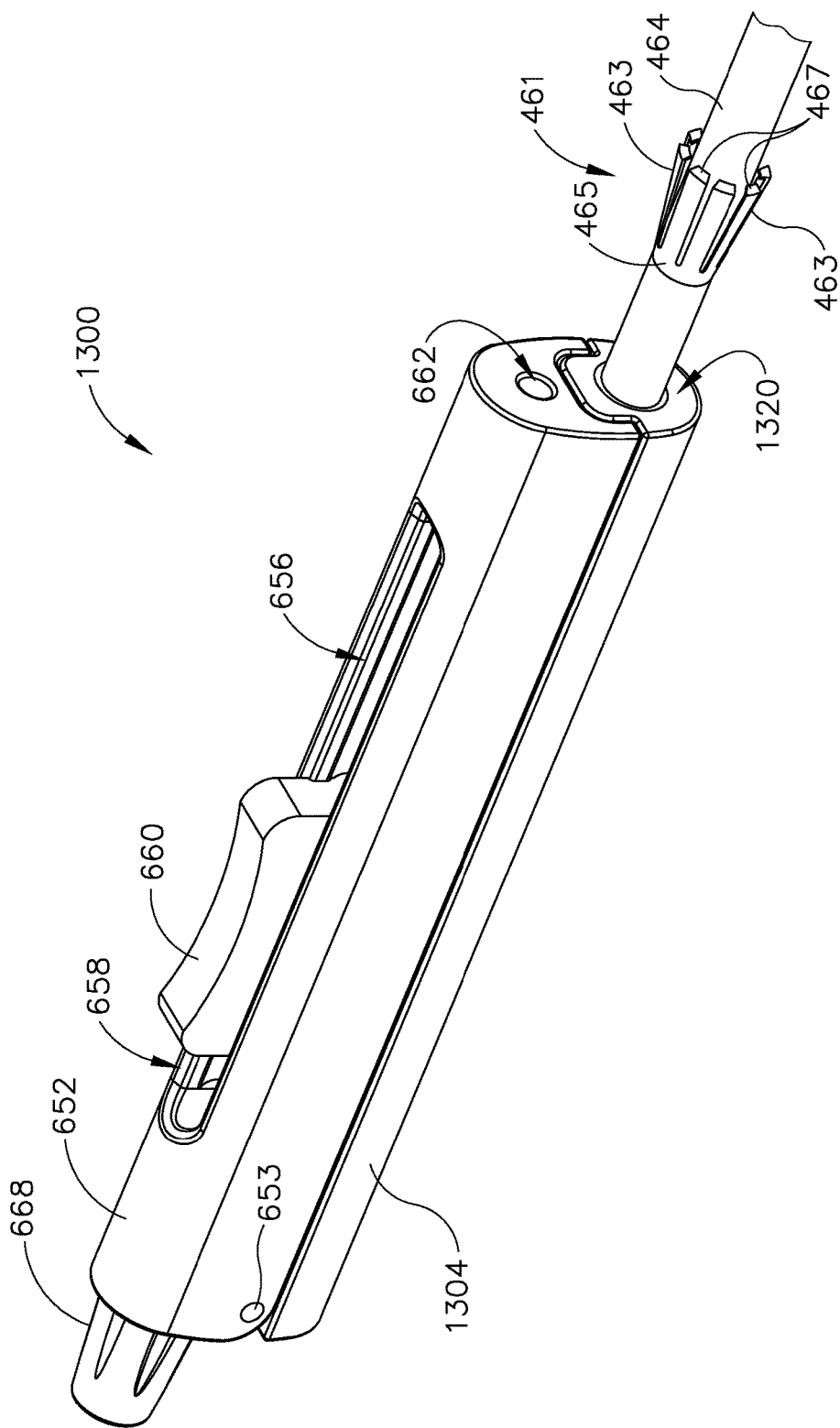
FIG. 58A depicts a perspective view of yet another exemplary handle suitable for use with the dilation catheter system of FIG. 12, with the endoscope of FIG. 15 having a locking member positioned thereon.
Figure 58B:
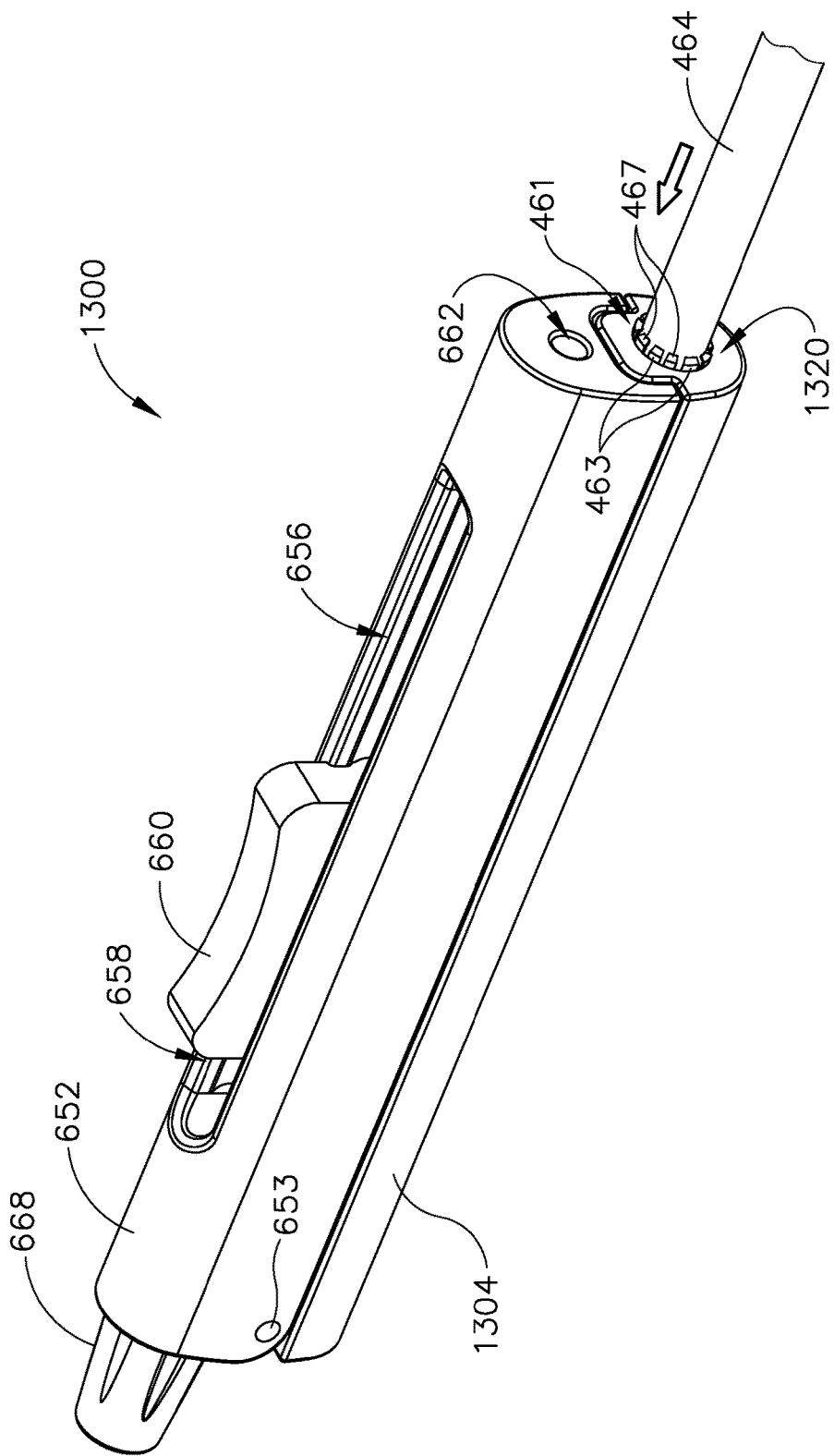
FIG. 58B depicts a perspective view of the handle of FIG. 58A with the endoscope translated distally such that the locking member is positioned within the handle.

FIGS. 58A and 58B show yet another exemplary handle (1300) having first body member (652) and its components as described above with reference to handle (650). Handle (750) further includes an exemplary alternative second body member (1304). As with handle (650) described above, the distal end of first body member (652) is pivotably coupled with a distal end of second body member (1304) via pin (653) such that first body member (652) and second body member (1304) are pivotable toward and away from one another about pin (653).

Second body member (1304) includes a through-bore (1320) formed therein. Through-bore (1320) extends the complete length of second body member (1304). As with through bore (670) of handle (650) described above, through-bore (1320) is operable to receive and selectively retain endoscope (460). Endoscope (460) of the present example comprises a locking member (461). Locking member (461) is secured about a portion of shaft (464) of endoscope (460). Locking member (461) comprises a plurality of cantilevered, resilient members (463) extending proximally and angularly-outwardly from an annular base (465) of locking member (461) about an exterior surface of endoscope (460). Each resilient member (463) includes a tab (467) extending inwardly from an unsupported end of each resilient member (463). Resilient members (463) are biased outwardly from the exterior surface of shaft (464) of endoscope (460) to the position shown in FIG. 58A. Endoscope (460) is translatable between a proximal (unlocked) position (FIG. 58A) and a distal (locked) position (FIG. 58B). As shown in FIG. 58B, with endoscope (460) translated distally relative to second body member (1304) into the distal (locked) position, an interior surface of through-bore (1320) bears against exterior surfaces of resilient members (463) so as to drive resilient members (463) inwardly toward an exterior surface of shaft (464) of endoscope (460) such that tabs (467) of resilient members (463) may bear against an exterior surface of endoscope (460). Friction between resilient member (463) and the interior surface of through-bore (1320) causes endoscope (460) to be selectively locked within through-bore (1320). It should be appreciated that endoscope (460) may be translated from the distal (locked) position into the proximal (unlocked) position so as to return resilient members (463) to their original position (FIG. 58A) in order to enable reorientation or maneuvering of endoscope (460).

It should be appreciated that handle (1300) may be grasped, oriented, and maneuvered, and actuator (1310) may be translated using a single hand. For instance, while grasping handle (1300), the user may use his or her index finger or thumb to orient first body member (1302) relative to second body member (1304) and/or to translate actuator (1310).

VII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A dilation system, wherein the dilation system comprises: (a) a body, wherein the body comprises a distal end and a proximal end; (b) a guide member, wherein the guide member is coupled to the distal end of the body and extends distally therefrom; (c) a dilation member, wherein the dilation member comprises an expandable dilator, wherein the dilation member is configured to translate relative to the guide member; (d) an endoscope, wherein endoscope is disposed within the body and extends distally therefrom; and (e) a locking feature, wherein the locking feature is configured to selectively lock the endoscope in position relative to the body; wherein the body, the guide member, the dilation member, the endoscope, and the locking feature are sized, arranged, and configured to be grasped and manipulated together by a single hand.

Example 2

The dilation system of Example 1, wherein the locking feature comprises a roller slidably disposed within a pair of slots formed in the body.

Example 3

The dilation system of Example 2, wherein the roller is configured to slide between an unlocked position and a locked position within the pair of slots, wherein the roller is configured to bear against the endoscope when in the locked position.

Example 4

The dilation system of any one or more of Examples 1 through 3, wherein the locking feature comprises a lever arm pivotably coupled with the body, wherein the lever arm is configured to pivot between an unlocked position and a locked position, wherein the lever arm is configured to bear against the endoscope when in the locked position.

Example 5

The dilation system of any one or more of Examples 1 through 4, wherein the locking feature comprises a sled slidably coupled with the body.

Example 6

The dilation system of Example 5, wherein the sled is configured to slide between an unlocked position and a locked position, wherein the sled is configured to bear against the endoscope when in the locked position.

Example 7

The dilation system of any one or more of Examples 5 through 6, wherein the locking feature further comprises at least one cantilevered resilient member, wherein the sled is configured to slide between an unlocked position and a locked position, wherein the sled is configured to bear against the at least one cantilevered resilient member when in the locked position so as to cause the at least one cantilevered resilient member to bear against the endoscope.

Example 8

The dilation system of any one or more of Examples 1 through 7, wherein the locking feature comprises a pair of resilient flanges.

Example 9

The dilation system of Example 8, wherein the locking feature further comprises a cover hingedly coupled with the body, wherein the cover is configured to rotate between an unlocked position and a locked position, wherein the cover is configured to bear against the resilient flanges when in the locked position so as to cause the resilient flanges to bear against the endoscope.

Example 10

The dilation system of any one or more of Examples 8 through 9, wherein the locking feature further comprises a lever pivotably coupled with the body, wherein the lever is configured to rotate between an unlocked position and a locked position, wherein the lever is configured to bear against the resilient flanges when in the locked position so as to cause the resilient flanges to bear against the endoscope.

Example 11

The dilation system of any one or more of Examples 1 through 10, wherein the locking feature comprises a threaded member threadably engaged with the body.

Example 12

The dilation system of any one or more of Examples 1 through 11, wherein the locking feature comprises at least one friction ring.

Example 13

The dilation system of any one or more of Examples 1 through 12, wherein the locking feature comprises a resilient cover coupled with the body via a living hinge.

Example 14

The dilation system of Example 13, wherein the locking feature further comprises a camming lever pivotably coupled with the body, wherein the camming lever is configured to rotate between an unlocked position and a locked position, wherein the camming lever is configured to bear against the resilient cover when in the locked position so as to cause the resilient cover to bear against the endoscope.

Example 15

The dilation system of any one or more of Examples 1 through 14, wherein the locking feature comprises a slidable button, wherein the slidable button is configured to slide between an unlocked position and a locked position, wherein the slidable button is configured to bear against bear against the endoscope when in the locked position.

Example 16

The dilation system of any one or more of Examples 1 through 15, wherein the guide member comprises a guide catheter, wherein the dilation member comprises a catheter, wherein the dilator comprises a balloon.

Example 17

A dilation catheter system, wherein the dilation catheter system comprises: (a) a body, wherein the body comprises a distal end and a proximal end; (b) a guide member, wherein the guide member is coupled to the distal end of the body and extends distally therefrom; (c) a balloon dilation catheter, wherein the dilation catheter comprises an expandable balloon dilator; (d) an endoscope, wherein endoscope is disposed within the body and extends distally therefrom; and (e) an actuator, wherein the actuator is slidably coupled with the body, wherein the actuator is translatable between a proximal position and a distal position, wherein the actuator is coupled with the balloon dilation catheter such that translation of the actuator is communicated to the balloon dilation catheter.

Example 18

The dilation system of Example 17, wherein one or both of the balloon and/or the guide member comprise a plurality of measurement markings.

Example 19

A dilation system, wherein the dilation system comprises: (a) a body, wherein the body comprises: (i) a first body member, wherein the first body member comprises a distal end and a proximal end, and (ii) a second body member, wherein the second body member comprises a distal end and a proximal end, wherein the first body member is pivotably coupled with the first body member such that the first body member and the second body member are configured to pivot toward and away from one another; (b) a guide member, wherein the guide member is coupled to the distal end of the first body member and extends distally therefrom; (c) a balloon dilation catheter, wherein the dilation catheter comprises an expandable balloon dilator, wherein the dilation catheter is configured to translate relative to the guide member; and (d) an endoscope, wherein endoscope is disposed within the second body member and extends distally therefrom.

Example 20

The dilation system of Example 19, wherein the body further comprises a rotation limiting feature configured to limit the amount by which first body member and second body member toward or away from one another.

VIII. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A dilation system, wherein the dilation system comprises:
   (a) a body, wherein the body comprises a distal end and a proximal end;
   (b) a guide member, wherein the guide member is coupled to the distal end of the body and extends distally therefrom;
   (c) a dilation member, wherein the dilation member comprises an expandable dilator, wherein the dilation member is configured to translate relative to the guide member;
   (d) an endoscope, wherein the endoscope is disposed within the body and extends distally therefrom alongside the guide member and exterior to the guide member;
   (e) a locking feature, wherein the locking feature is configured to selectively lock the endoscope in position relative to the body; and
   (f) an actuator, wherein the actuator surrounds an exterior surface of the body, wherein a portion of the actuator protrudes radially inwardly into an inner, channel of the body to slidably couple the actuator and the dilation member to the body;
   wherein the body, the guide member, the dilation member, the endoscope, and the locking feature are sized, arranged, and configured to be grasped and manipulated together by a single hand.

2. The dilation system of claim 1, wherein the guide member comprises a guide catheter, wherein the dilation member comprises a catheter, wherein the dilator comprises a balloon.

3. A dilation catheter system, wherein the dilation catheter system comprises:
   (a) a body, wherein the body comprises an inner slot located between a distal end and a proximal end;

(b) a guide member, wherein the guide member is coupled to the distal end of the body and extends distally therefrom;

(c) a balloon dilation catheter, wherein the dilation catheter comprises an expandable balloon dilator;

(d) an endoscope, wherein endoscope is disposed within the body and extends distally therefrom, wherein the endoscope extends alongside the guide member and exterior to the guide member; and (e) an actuator, wherein the actuator is slidably coupled with and surrounds an exterior surface of the body and a portion of the actuator protrudes radially inwardly within the inner slot, wherein the actuator is translatable along the inner slot of the body between a proximal position and a distal position, wherein the actuator is coupled with the balloon dilation catheter within the inner slot such that translation of the actuator is communicated to the balloon dilation catheter.

4. The dilation system of claim 3, wherein one or both of the balloon dilation catheter and/or the guide member comprise a plurality of measurement markings.

5. A dilation system, wherein the dilation system comprises:

(a) a body, wherein the body includes an internal channel and an external surface;

(b) a guide member, wherein the guide member is coupled to the distal end of the body and extends distally therefrom;

(c) a dilation catheter, wherein the dilation catheter comprises an expandable balloon dilator, wherein the dilation catheter is configured to translate relative to the guide member;

(d) an endoscope, wherein endoscope is disposed within the body and extends distally therefrom, wherein the endoscope extends alongside the guide member and exterior to the guide member;

(e) an actuator, wherein the actuator surrounds the external surface of the body, wherein a portion of the actuator protrudes radially inwardly into the internal channel of the body to couple the actuator to the dilation catheter, wherein the actuator is configured to translate along the external surface and within the internal channel of the body from a proximal position to a distal position;

wherein the balloon dilation catheter is coupled to the actuator within the internal channel such that the actuator is translatable to thereby advance the expandable balloon dilator; and wherein the expandable balloon dilator is configured to be disposed within the guide member when the actuator is in the proximal position, wherein the expandable balloon dilator is configured to extend beyond the guide member when the actuator is in the distal position.

6. The dilation system of claim 5, wherein the actuator includes a bore configured to receive the balloon dilation catheter within the internal channel of the body.

* * * * *